US006766183B2

United States Patent
Walsh et al.

(10) Patent No.: US 6,766,183 B2
(45) Date of Patent: Jul. 20, 2004

(54) LONG WAVE FLUOROPHORE SENSOR COMPOUNDS AND OTHER FLUORESCENT SENSOR COMPOUNDS IN POLYMERS

(75) Inventors: Joseph C. Walsh, Los Angeles, CA (US); Aaron M. Heiss, Orange, OH (US); Glenn Noronha, Oceanside, CA (US); David J. Vachon, Granada Hills, CA (US); Stephen M. Lane, Oakland, CA (US); Joe H. Satcher, Jr., Patterson, CA (US); Thomas A. Peyser, Menlo Park, CA (US); William Peter Van Antwerp, Valencia, CA (US); John Joseph Mastrototaro, Los Angeles, CA (US)

(73) Assignees: Medtronic MiniMed, Inc., Northridge, CA (US); The Regents of the University of California, Oakland, CA (US)

( * ) Notice: Subject to any disclaimer, the term of this patent is extended or adjusted under 35 U.S.C. 154(b) by 373 days.

(21) Appl. No.: 10/033,240

(22) Filed: Dec. 28, 2001

(65) Prior Publication Data

US 2002/0193672 A1 Dec. 19, 2002

Related U.S. Application Data

(63) Continuation-in-part of application No. 09/461,627, filed on Dec. 14, 1999, which is a continuation of application No. 08/749,366, filed on Nov. 21, 1996, now Pat. No. 6,002,954.
(60) Provisional application No. 60/336,317, filed on Nov. 1, 2001, and provisional application No. 60/007,575, filed on Nov. 22, 1995.

(51) Int. Cl.$^7$ .............................. A61B 5/00; G01N 33/00
(52) U.S. Cl. ..................... 600/317; 600/341; 436/94; 436/95; 436/172; 422/82.07; 568/1; 546/13
(58) Field of Search ............................. 600/310, 312, 600/317, 322, 341, 342; 436/94, 95, 172; 422/82.07; 568/1; 546/13

(56) References Cited

U.S. PATENT DOCUMENTS

| 4,236,071 | A | 11/1980 | Chimenti |
|---|---|---|---|
| 4,401,122 | A | 8/1983 | Clark, Jr. |
| 4,428,366 | A | 1/1984 | Findl et al. |
| 4,455,741 | A | 6/1984 | Kolodner |

(List continued on next page.)

FOREIGN PATENT DOCUMENTS

| EP | 0 673 622 A3 | 9/1995 |
|---|---|---|
| EP | 0 693 271 A1 | 1/1996 |
| EP | 0 729 962 A1 | 9/1996 |
| FR | 2 253 794 | 7/1975 |

(List continued on next page.)

OTHER PUBLICATIONS

Appleton et al., "Detection of Total Sugar Concentration Using Photoinduced Electron Transfer Materials: Development of Operationally Stable, Reusable Optical Sensors." Sensors and Actuators B, Elsevier Sequoia, 2000, 65(1–3): 302–304.

(List continued on next page.)

*Primary Examiner*—Eric F. Winakur
(74) *Attorney, Agent, or Firm*—Gates & Cooper LLP

(57) ABSTRACT

Fluorescent biosensor molecules, fluorescent biosensors and systems, as well as methods of making and using these biosensor molecules and systems are described. Embodiments of these biosensor molecules exhibit fluorescence emission at wavelengths greater than about 650 nm. Typical biosensor molecules include a fluorophore that includes an iminium ion, a linker moiety that includes a group that is an anilinic type of relationship to the fluorophore and a boronate substrate recognition/binding moiety, which binds glucose. The fluorescence molecules modulated by the presence or absence of polyhydroxylated analytes such as glucose. This property of these molecules of the invention, as well as their ability to emit fluorescent light at greater than about 650 nm, renders these biosensor molecules particularly well-suited for detecting and measuring in-vivo glucose concentrations.

46 Claims, 42 Drawing Sheets

U.S. PATENT DOCUMENTS

| | | |
|---|---|---|
| 4,496,722 A | 1/1985 | Gallop et al. |
| 4,542,987 A | 9/1985 | Hirschfeld |
| 4,600,306 A | 7/1986 | Hara et al. |
| 4,655,225 A | 4/1987 | Dahne et al. |
| 4,680,268 A | 7/1987 | Clark, Jr. |
| 4,805,623 A | 2/1989 | Jobsis |
| 4,861,728 A | 8/1989 | Wagner |
| 4,875,486 A | 10/1989 | Rapoport et al. |
| 4,882,492 A | 11/1989 | Schlager |
| 4,923,819 A | 5/1990 | Fernandez et al. |
| 4,924,009 A | 5/1990 | Neckers et al. |
| 4,929,387 A | 5/1990 | Hayden et al. |
| 4,974,929 A | 12/1990 | Curry |
| 5,028,787 A | 7/1991 | Rosenthal et al. |
| 5,032,315 A | 7/1991 | Hayden et al. |
| 5,049,738 A | 9/1991 | Gergely et al. |
| 5,054,487 A | 10/1991 | Clarke |
| 5,070,874 A | 12/1991 | Barnes et al. |
| 5,077,476 A | 12/1991 | Rosenthal |
| 5,086,229 A | 2/1992 | Rosenthal et al. |
| 5,101,814 A | 4/1992 | Palti |
| 5,112,124 A | 5/1992 | Harjunmaa et al. |
| 5,137,833 A | 8/1992 | Russell |
| 5,173,456 A | 12/1992 | Hayden et al. |
| 5,182,214 A | 1/1993 | Kessler et al. |
| 5,196,709 A | 3/1993 | Berndt et al. |
| 5,198,670 A | 3/1993 | VanCauter et al. |
| 5,203,328 A | 4/1993 | Samuels et al. |
| 5,235,045 A | 8/1993 | Lewis et al. |
| 5,235,606 A | 8/1993 | Mourou et al. |
| 5,246,867 A | 9/1993 | Lakowicz et al. |
| 5,262,526 A | 11/1993 | Sasamoto et al. |
| 5,270,548 A | 12/1993 | Steinkamp |
| 5,279,543 A | 1/1994 | Glikfeld et al. |
| 5,281,825 A | 1/1994 | Berndt et al. |
| 5,308,773 A | 5/1994 | Lewis et al. |
| 5,313,485 A | 5/1994 | Hamil et al. |
| 5,322,796 A | 6/1994 | Ishikawa |
| 5,342,789 A | 8/1994 | Chick et al. |
| 5,353,790 A | 10/1994 | Jacques et al. |
| 5,362,307 A | 11/1994 | Guy et al. |
| 5,409,835 A | 4/1995 | Lakowicz et al. |
| 5,439,797 A | 8/1995 | Tsien et al. |
| 5,445,611 A | 8/1995 | Eppstein et al. |
| 5,458,140 A | 10/1995 | Eppstein et al. |
| 5,476,094 A | 12/1995 | Allen et al. |
| 5,485,530 A | 1/1996 | Lakowicz et al. |
| 5,495,850 A | 3/1996 | Zuckerman |
| 5,503,770 A | 4/1996 | James et al. |
| 5,504,337 A | 4/1996 | Lakowicz et al. |
| 5,512,246 A | 4/1996 | Russell et al. |
| 5,515,864 A | 5/1996 | Zuckerman |
| 5,528,046 A | 6/1996 | Ishikawa |
| 5,528,611 A | 6/1996 | Scheps |
| 5,590,141 A | 12/1996 | Baird et al. |
| 5,599,504 A | 2/1997 | Hosoi et al. |
| 5,626,134 A | 5/1997 | Zuckerman |
| 5,628,310 A | 5/1997 | Rao et al. |
| 5,648,270 A | 7/1997 | Kuhn et al. |
| 5,666,373 A | 9/1997 | Sharp et al. |
| 5,674,743 A | 10/1997 | Ulmer |
| 5,763,238 A | 6/1998 | James et al. |
| 5,776,782 A | 7/1998 | Tsuji |
| 5,784,157 A | 7/1998 | Gorfinkel et al. |
| 5,798,306 A | 8/1998 | Dickinson, Jr. |
| 5,814,820 A | 9/1998 | Dong et al. |
| 5,818,582 A | 10/1998 | Fernandez et al. |
| 5,825,798 A | 10/1998 | Momiuchi et al. |
| 5,846,726 A | 12/1998 | Nadeau et al. |
| 5,865,754 A | 2/1999 | Sevick-Muraca et al. |
| 5,888,739 A | 3/1999 | Pitner et al. |
| 5,909,278 A | 6/1999 | Deka et al. |
| 5,911,952 A | 6/1999 | Tsuji |
| 5,919,630 A | 7/1999 | Nadeau et al. |
| 5,928,869 A | 7/1999 | Nadeau et al. |
| 5,935,791 A | 8/1999 | Nadeau et al. |
| 5,952,236 A | 9/1999 | Thompson et al. |
| 5,955,737 A | 9/1999 | Hallidy et al. |
| 5,981,957 A | 11/1999 | Cruce et al. |
| 5,987,049 A | 11/1999 | Weingarten et al. |
| 5,990,484 A | 11/1999 | Ohsuka |
| 5,994,707 A | 11/1999 | Mendoza et al. |
| 6,002,954 A | 12/1999 | Van Antwerp et al. |
| 6,011,984 A | 1/2000 | Van Antwerp et al. |
| 6,040,194 A | 3/2000 | Chick et al. |
| 6,157,037 A | 12/2000 | Danielson |
| 6,184,535 B1 | 2/2001 | Kashima et al. |
| 6,200,818 B1 | 3/2001 | Eigen et al. |
| 6,214,628 B1 | 4/2001 | Lakowicz et al. |
| 6,225,127 B1 | 5/2001 | Thompson et al. |
| 6,344,360 B1 | 2/2002 | Colvin et al. |
| 6,387,672 B1 * | 5/2002 | Arimori et al. ............. 436/172 |
| 6,627,177 B2 * | 9/2003 | Singaram et al. ............ 424/9.6 |

FOREIGN PATENT DOCUMENTS

| | | |
|---|---|---|
| GB | 2 284 809 | 6/1995 |
| WO | WO 82/01804 | 5/1982 |
| WO | WO 91/04488 | 4/1991 |
| WO | WO 91/18912 | 12/1991 |
| WO | WO 96/03074 | 2/1996 |
| WO | WO 97/19188 | 5/1997 |
| WO | WO 97/29154 | 8/1997 |
| WO | WO 98/22820 | 5/1998 |
| WO | WO 99/46600 | 9/1999 |
| WO | WO 01/18543 | 3/2001 |
| WO | WO 01/20334 | 3/2001 |
| WO | WO 02/054067 | 7/2002 |

OTHER PUBLICATIONS

Burnett et al., "Synthesis of a Fluorescent Boronic Acid . . . Erythrocytes," Biochemical and Biophysical Research Communications, 1980, 96(1): 157–162.

Czarnik, "Chemical Communication in . . . Chemosensors," Acc. Chem. Res., 1994, 27:302–308.

Joon et al., "Fluorescent chemosensors . . . found," SPIE, 1992, vol. 1796, pp. 87–91.

Kemp et al., "Synthesis of Cyclophanes . . . methylnaphrhalenes," The Journal of Organic Chemistry, 1979, 44(25):4700–4703.

Mohler et al., "α–Amino Acid Chelative . . . Acid," J. Am. Chem. Soc., 1993, 115:7037–7038.

Okafor, "Synthesis, Properties and Uses of Angular Phenoxazines," Dyes and Pigments, Elsevier Applied Science Publishers Ltd., England, vol. 7, No. 2, 1986, pp. 103–131, XP–002122264.

Patterson et al., "Tuning the Affinity of a Synthetic Sialic Acid Receptor Using Combinatorial Chemistry," Tetrahedron Lett., 1998, 39(20): 3111–3114.

Xuhong, Qian et al., "The Synthesis, Application and Prediction of Stokes Shift in Fluorescent Dyes Derived from 1,8–Naphthalic Anhydride," Dyes and Pigments, Elsevier Applied Science Publishers Ltd., England, vol. 11, No. 1, 1989, pp. 13–20, XP–000026521.

Yoon et al., "Fluorescent chemosensors . . . found," SPIE, 1992, 1796:87–91.

Arnold et al., "Determination of Physiological Levels . . . Spectra," Anal. Chem., 1990, 62:1457–1464.

Bostick et al., "Quantitative Determination of Blood . . . Luminol," Anal. Chemistry, 1975, 47(3):447–452.

DCCT Research Group, "The Effect of Intensive Treatment . . . Mellitus," The New England Journal of Medicine, 1993, 329(14):977–986.

Falasca et al., "Purification and Partial . . . Sativa," Biochimica or Biophysica Acta, 1979, 577:71–81.

Gough et al., "Development of the Implantable Glucose Sensor," Diabetes, 1995, 44:1005–1009.

Guilbaulr et al., "Homovanillie Acid as a . . . Enzymes." Analytic Chemistry, 1968, 40(1):190–196.

Indelli et al., "Salt Effects in the Reaction . . . Ions," Journal of the American Chemical Society, 1960, 82(13):3233, 3863–3866.

James et al., "Novel Photoinduced . . . Amine," J. Chem. Soc., Chem. Commun., 1994, pp. 477–478.

James et al., "Novel Saccharide–Photoinduced . . . Amine," J. Am. Chem. Soc., 1995, 117:8982–8987.

James et al., "Chiral discrimination of . . . sensor," Nature, 1995, 374:345–347.

Lakowicz, et al., "Emerging Biomedical and Advanced Applications . . . Spectroscopy," Journal of Fluorescence, 1994, 4(1):117–136.

Lakowicz et al., "Fluorescence lifetime–based sensing . . . glucose," Sensors and Actuators B, 1993, 11:133–143.

Lin et al., J. Org. Chem., 1979, 44(25):4701–4703.

Marquardt et al., "Near–Infrared Spectroscopic . . . Matrix," Anal. Chem., 1993, 65:3271–3278.

Monroe, "Novel implantable glucose sensors," ACL, 1989, pp. 8–16.

Nakashima et al., "Sugar–Assisted Chirality . . . Complexes," Chemistry Letters, 1994, pp. 1267–1270.

Pilosof et al., "Microporous Membrane Flow . . . Glucose," Anal. Chem., 1982, 54:1698–1701.

Reach et al., Anal. Chem., 1992, 64(6):381–386.

Sandanavake et al., "Molecular Fluorescence Sensor . . . Coumarin," Chemistry Letters, 1995, pp. 139–140.

Uziel et al., "Direct Labeling of DNA . . . Group," Biochemical and Biophysical Research Communications, 1991, 180(3):1233–1240.

Yoon et al., "Fluorescent Chemosensors of . . . Quenching$_f$," J. Am. Chem. Soc. 1992, 114:5874–5875.

* cited by examiner

Mitotracker Red boronate

COB

LONG WAVE FLUOROPHORE SENSOR COMPOUNDS AND OTHER FLUORESCENT SENSOR COMPOUNDS IN POLYMERS

This application is a Continuation-in-Part application of U.S. patent application Ser. No. 09/461,627, filed Dec. 14, 1999, which is a Continuation Application of U.S. patent application Ser. No. 08/749,366 filed Nov. 21, 1996, now U.S. Pat. No. 6,002,954, which claims priority to U.S. Provisional Application Serial No. 60/007,515, filed Nov. 22, 1995; and this application claims priority from U.S. Provisional Application Serial No. 60/336,317, filed Nov. 1, 2001; and this application is related to U.S. patent application Ser. No. 08/721,262, filed Sep. 26, 1996, now U.S. Pat. No. 5,777,060 which is a Continuation-in-Part of U.S. patent application Ser. No. 08/410,775, filed Mar. 27, 1995, now abandoned, the disclosures of each being incorporated herein by reference.

This invention was made with United States Government support under CRADA number 70NANB8H4065 awarded by the National Institute of Standards and Technology (NIST). The United States Government has certain rights in the invention.

Portions of this work have been performed under the auspices of the U.S. Department of Energy by the University of California, Lawrence Livermore National Laboratory under Contract No. W-7405-ENG-48. The government may have certain rights to this invention.

FIELD OF THE INVENTION

This invention relates to optical biosensor systems that utilize fluorescent molecules in the determination of the concentration of polyhydroxylate analytes, particularly glucose. These fluorescent molecules typically include a boronate moiety and a fluorophore that includes an iminium ion. The invention further relates to implantable, optical biosensor systems that utilize these molecules for the determination of in-vivo glucose concentrations.

BACKGROUND OF THE INVENTION

The accurate monitoring of biological analytes allows for the efficient management and treatment of a number of disease states. Notably, for approximately 16 million people in the United States afflicted with diabetes, detection and quantification of blood glucose levels substantially lessens the disease's symptomatic complications (see, e.g. Kahn, C. R. "Conquering Diabetes, A Strategic Plan for the $21^{st}$ Century"; A report of the Congressionally-Established Diabetes Research Working Group, NIH Publication No. 99-4398; 1999). Current technology generally requires that a blood sample be obtained from a patient for the measurement of blood glucose levels. In order to accurately reflect the body's ever-changing response to meals, activities and even stress, measurement of blood glucose should be on a frequent basis. Due to the discomfort and sterility issues, the frequent sampling of a patient's blood to determine glucose levels is impractical, at best. Thus, devices and methods to frequently monitor blood glucose levels without taking numerous blood samples from a patient are desirable.

Over the years, researchers in the medical devise industry sought new technologies incorporating optochemical methods for detecting and quantifying subcutaneous glucose. Research on optochemical methods for detecting glucose focuses on the development of a long-term, minimally invasive optochemical glucose monitoring devise that, once implanted, is painless to interrogate, amenable to continuous monitoring, and ultimately useful as a component of a closed-loop artificial pancreas.

Fluorescent reporter molecules are useful in optochemical methods for monitoring changing glucose levels in-vivo. However, in order to use fluorescent reporter molecules to detect and measure the concentration of glucose in-vivo, numerous problems need to be surmounted. One particular problem is that fluorescence transmitted through skin is generally poor at visible wavelengths less than about 500 nm. To improve transmission of the signal through the skin, the fluorescent compound should operate at longer wavelengths greater than about 450 nanometers. The transmission through a few millimeters of skin increases logarithmically with wavelength—from 0.1% at about 400 nm to almost 100% at 850 nm. Thus, the longer the wavelength, the greater the transmission through skin. Excitation and emission wavelengths greater than about 600–700 nm are an enormous improvement over those of about 400–450 nm. Because of the significant increase in optical skin transmission at longer wavelengths, a practical glucose sensor can operate more efficiently, more accurately, and with a greater signal-to-noise ratio. In addition, it is advantageous to match the peak excitation wavelength with an existing light source (such as an LED or diode laser). Furthermore, by operating at longer wavelengths, there is a reduction in the tissue autofluorescence background.

Embodiments of this invention address the problem of obtaining adequate optical transmission of fluorescence using fluorescent reporter molecules in-vivo to report on the body's fluctuating glucose concentrations.

SUMMARY OF THE DISCLOSURE

Embodiments of the fluorescent biosensor molecules of the present invention include an oxazine-based fluorophore, a boronate binding moiety which specifically binds polyhydroxlate analyte, and a linker moiety which provides a linkage between the fluorophore and the boronate binding moiety. These biosensor molecules typically emit light in the visible region of the spectrum, preferably above about 600 nm and more preferably above about 650 nm.

Specific embodiments of the biosensor molecules of the invention typically have an excitation spectra that is greater than about 550 nm, preferably above about 600 nm. Further, these biosensor molecules have at least one wavelength in their emission spectra that is greater than about 550 nm, preferably above about 600 nm and more preferably above about 650 nm and exhibits an intensity that is at least about 25 percent of the intensity of a wavelength of maximum intensity in the visible region of the spectrum, more preferably these biosensor molecules have at least one wavelength in their emission spectrum that is greater than about 550 nm, preferably above about 600 nm and more preferably above about 650 nm and exhibits an intensity that is at least 25 percent of the intensity of a wavelength of maximum intensity in the visible region.

An exemplary oxazine-based biosensor molecule of the present invention utilizes Nile blue as the fluorophore as shown in FIG. 2. The Nile blue-based biosensor molecule has an excitation wavelength of about 625 nm and a maximum emission wavelength of about 675 nm (see, e.g. FIGS. 8). Similar oxazine-based fluorophores suitable for use in embodiments of the present invention may include one or more functional groups selected from the following: aliphatic, aromatic, haloalkane, alcohol, ether, amine, cyano, nitro group, aldehyde, ketone, ester, carboxylic acid, sulfonic acid and phosphoric acid functional groups.

Other embodiments of the oxazine-based biosensor molecules of the invention can include ditopic molecules, which generally include two boronate substrate recognition sites. These ditopic embodiments of the invention are designed to bind to one or more polyhydroxylate analyte molecules, such as glucose, per ditopic biosensor molecule, and thus, increase the sensitivity of the sensing ability of these biosensor molecules.

Typical embodiments of the invention include oxazine-based biosensor molecules that are either contained within, or attached to, a polymer matrix to form embodiments of the fluorescent biosensor of the invention. Preferably, the polymer matrix materials selected for use with the biosensors of the invention are biocompatible. The use of biocompatible polymeric materials is preferred in contexts where the biosensors are in contact with body fluids and tissue. Thus, embodiments of the biosensors of the invention are especially suitable for implantation beneath the skin where they serve as in-vivo reporters of analyte concentrations, particularly glucose concentrations.

In particular embodiments of the invention disclosed herein, the functional group on the oxazine-based fluorophore that is capable of forming a covalent linkage to the linker moiety is an aldehyde, an amine or a halogen. Also in embodiments of the synthetic method, the linker moiety includes an amino functional group. Still other embodiments of this invention include reacting a linker moiety that further includes a hydroxyl, an amino or a carboxy functional group capable of forming a covalent attachment to a polymer matrix. In an exemplary embodiment, the phenyl group on the polyhydroxylate analyte binding moiety includes a reactive halogen.

Other aspects of the invention include an oxazine-based boronate fluorescent biosensor systems for measuring in-vivo levels of a polyhydroxylate analyte, particularly glucose. Embodiments of these biosensor systems include an oxazine-based fluorescent biosensor molecule attached to, or contained within, a polymer matrix to yield an oxazine-based biosensor of the biosensor system. These biosensor systems also include an optical light source and a detector that detects a fluorescent signal that can be correlated with in-vivo levels of the polyhydroxylate analyte.

Embodiments of the biosensor system of the invention include a biosensor that is implanted subcutaneously beneath a person's skin. These biosensors may also include various agents that increase the overall biocompatibility and functioning of the biosensors when these agents are admixed into the polymer matrix, or coated atop of the polymer matrix that is in contact with the body, or the like. Particular embodiments of the biosensor system include an implanted biosensor that emits light through the skin of the person with this light being detected by a detector. Other embodiments include biosensor systems where the biosensor is transdermally, or percutaneously, implanted and includes a fiber optic for light passage through to, or from, the implanted biosensor. Biosensor systems in accordance with embodiments of the invention may be injected or otherwise introduced subcutaneously beneath a person's skin.

Other aspects of the invention include an implantable biosensor which includes an oxazine-based fluorophore; a boronate binding moiety which specifically and reversibly binds polyhydroxylate analyte; a linker moiety which links the fluorophore to the boronate binding moiety to form a biosensor molecule, where the biosensor molecule emits a signal in the visible to near infrared region of the spectrum that can be correlated to polyhydroxylate analyte concentration; and a polymer matrix that is attached to the biosensor molecules. Typically the polymer matrix may be water-soluble and selected from at least polyethylene glycol (amino-terminated), Jeffamine polymers (2-propyl amino-terminated block-polypropylene oxide block-polyethylene oxide block-polypropylene oxide), poly(vinyl alcohol), poly (acrylic acid) and mixtures of these polymers. Using a water-soluble polymer matrix to immobilize the oxazine-based biosensor molecules in accordance with embodiments of the invention may require that the biosensor is further contained in a biocompatible, water-insoluble material that is permeable to the polyhydroxylate analyte, where the water-insoluble material is selected from at least polyesters of carbonic acid, poly(vinylchloride), polyamides, polychloroethers, poly(urethanes), poly(imides) and mixtures of these materials. Moreover, the implantable biosensor may be immobilized in a polymer matrix that has multiple attachment-points, such as cross-linked poly(vinyl alcohol), cross-linked poly(acrylic acid), star dendrimers and mixtures of these polymers. When using these polymers no further encapsulation may be required. A particular embodiment of an implantable biosensor in accordance with embodiments of the invention utilizes a polycarboxystyrene polymer matrix. In this example, as well as examples of other polymer matrices, the polymer matrix can be made to be water-soluble or water-insoluble by adjusting the overall length as well as the level of crosslinking of the polymer.

Another aspect of the invention are methods of quantifying the amount of polyhydroxylate analyte in-vivo, particularly glucose. These methods include interrogating an implanted oxazine-based biosensor, which includes oxazine-based biosensor molecules contained within or attached to a polymer matrix, with a light source to produce excited state biosensor molecules that yield an emission signal. This emission signal, which correlates to the amount of polyhydroxylate analyte in the body fluids surrounding the biosensor implant, is then detected by a detector. The amount of polyhydroxylate analyte surrounding the in-vivo implanted biosensor is then quantified from the emission signal. These methods preferably utilize biosensor molecules that have a maximal emission signal at about 600 nm or greater, more preferably at about 675 nm.

BRIEF DESCRIPTION OF THE DRAWINGS

The file of this patent contains at least one drawing executed in color. Copies of this patent with color drawing(s) will be provided by the patent and Trademark Office upon request and payment of the necessary fee.

FIGS. 20B and 20C provide an illustrative sensor embodiment.

DETAILED DESCRIPTION OF THE PREFERRED EMBODIMENTS

Figure 1:
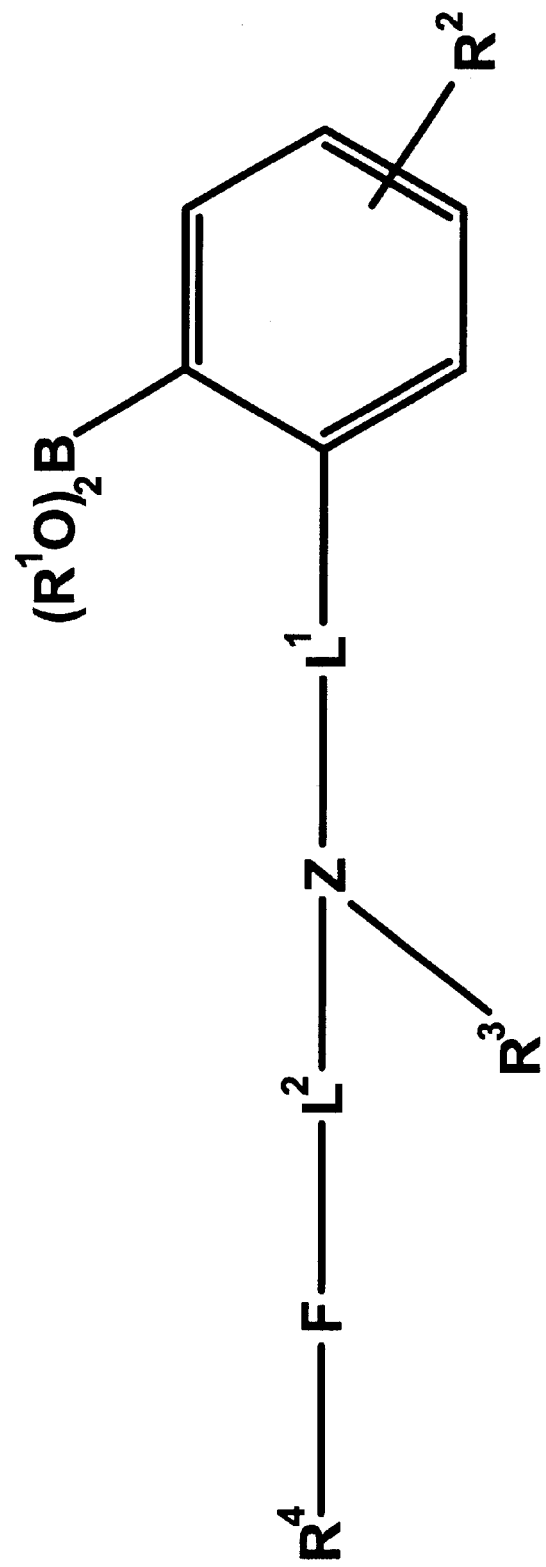
FIG. 1 shows general chemical formula of the biosensor molecules used in various embodiments of the invention described herein. In typical embodiments F is a fluorophore, $L^1$ and $L^2$ are optional linking groups, Z is a heteroatom, preferably a nitrogen. In such embodiments, the linkages $L^1$ and $L^2$ are each generally 0–4 contiguous atoms selected from carbon, oxygen, nitrogen, sulfur, and phosphorous, and preferably are simple alkyl chains.

Embodiments of the present invention are directed to fluorescent compounds whose fluorescent properties are modulated by interactions with polyhydroxylate analytes. These compounds contain boronate moieties such as arylboronic acid functional groups, moieties which are used in the art as molecular recognition motifs to bind various polyhydroxylate analytes including glucose, galactose, fructose, mannose, maltose, cellobiose and lactose (see, e.g., Nakashima, et al., Chem. Lett. 1267 (1994); James, et al., J. Chem. Soc. Chem. Commun, 477 (1994); James, et al., Nature, 374:345 (1995); and Yoon, et al., J. Am. Chem. Soc., 114:5874 (1992) which are incorporated by reference herein). Typical fluorescent compounds of the invention can include an anilinic structure and a fluorophore that includes an iminium ion.

Embodiments of the invention include optical biosensor systems that include these fluorescent compounds encompassed within a polymer matrix and methods of using these compounds to report on in-vivo levels of glucose. These compounds and systems are particularly useful in methods for the detection and measurement of in-vivo glucose concentrations via fluorescence. Related compounds and systems are described in U.S. Pat. No. 6,002,954, filed on Nov. 21, 1996, U.S. Ser. No. 09/663,567, filed on Sep. 15, 2000, U.S. Ser. No. 09/823,522, filed on Mar. 30, 2001, 09/826,745, filed on Apr. 4, 2001, U.S. Provisional application Serial No. 60/269,226, filed on Feb. 15, 2001 and U.S. Ser. No. 09/952,563, filed on Sep. 12, 2001, which are herein incorporated by reference in their entireties.

Optical biosensors make possible the detection of polyhydroxylate analytes, such as glucose, in various media. These sensors emit fluorescent signals when bound to glucose that differ in intensity to those signals emitted when not bound to glucose. This phenomenon, referred to as glucose transduction, is the basis for quantifying glucose levels in various media. For example, anthracene boronate-based glucose-sensing molecules exhibit a 50% increase in fluorescence intensity at 420 nm upon addition of a specific amount of glucose (Chem. Commun. 1997, 71–72). This anthracene-based boronate system and other optical-based glucose-sensing systems are useful for detection of glucose in vitro. These glucose-sensing systems, however, can have a somewhat limited potential in vivo. Limitations can include the inability to transduce glucose in substantially aqueous or biologically relevant media and the inability to fluoresce at wavelengths above 500 nm. Indeed, the transmission of shorter wavelength light through tissue is problematic for reasons including, but not limited to, scattering of the incoming and outgoing signals and harmful effects of tissue exposure due to lower wavelength radiation. Embodiments of the invention utilize water-soluble and long wavelength-based oxazine fluorophores to overcome these obstacles. Water solubility of the fluorophore can increase the glucose sensing potential of the optical sensor in vivo. There are other salient features required to make an optimized fluorophore system for subcutaneous glucose detection. The fluorophore should have appropriate sites for chemical modification and polymer incorporation and the fluorophore should respond to changes in glucose in substantially aqueous systems when incorporated into a glucose sensor. The long wavelength fluorophore portion of the glucose-sensing molecule should posses an excitation above 550 nm and an emission above 600 nm in order to circumvent the aforementioned problems. In this context, oxazine fluorophores are water soluble, highly fluorescent, long wavelength molecules possessing a characteristic fused aromatic, heterocyclic ring system.

Figure 7:
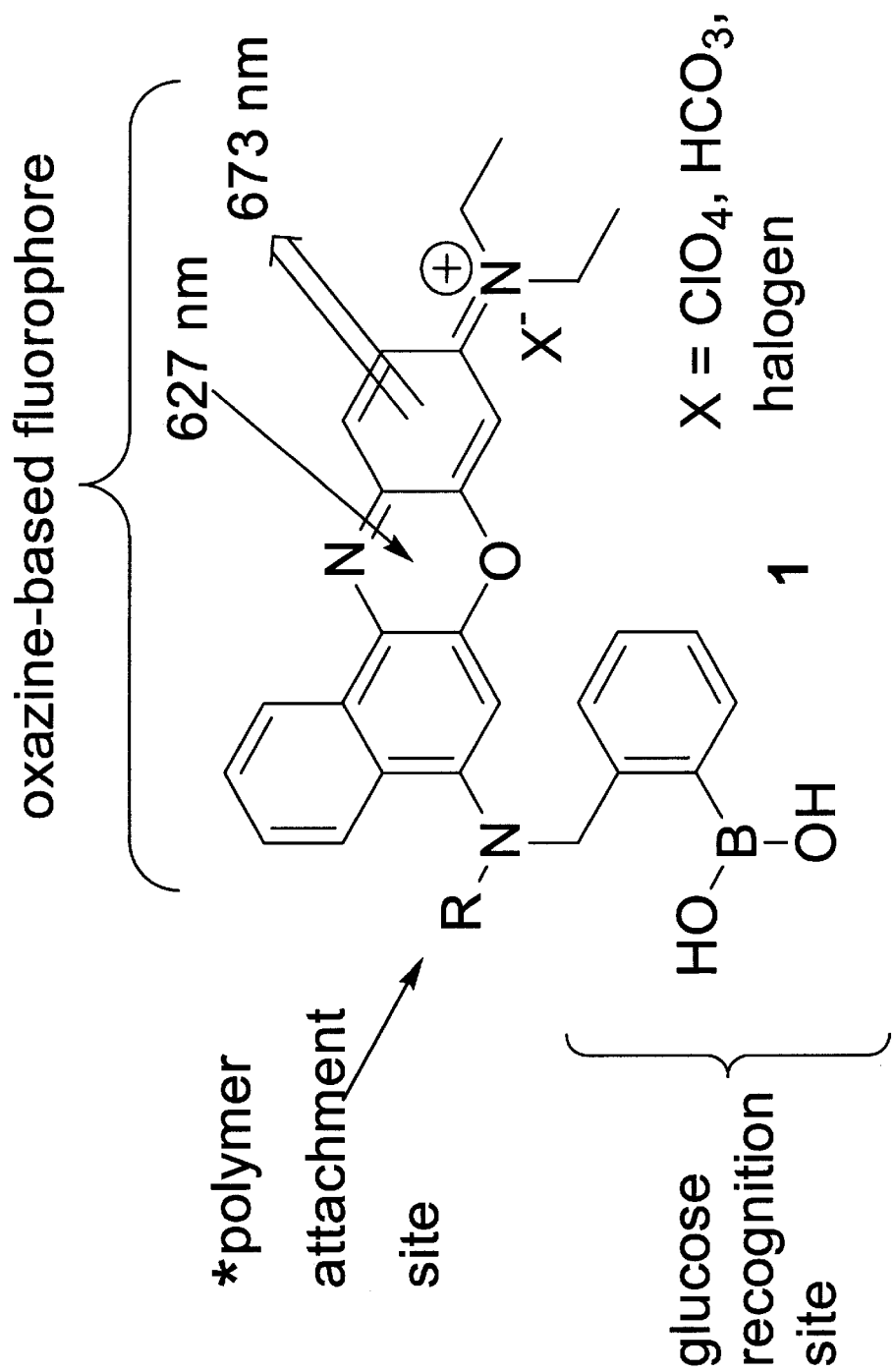
FIG. 7 provides an illustration of a typical oxazine-based boronate fluorophore (Nile blue) for glucose sensing.

Among oxazine containing optical biosensor molecules, the presence of a conjugated iminium ion, as well as an anilinic group in relation to the fluorophore (e.g. where some portion of this compound has an atomic arrangement that is analogous to aniline, for example as shown in the compound of FIG. 7 where a nitrogen atom is bound to a phenyl ring) may facilitate the overall transducing ability of the biosensor molecule. Without being held to any particular theory, it is postulated that embodiments of the biosensor molecules of the invention owe their transducing ability, at least in part, to a Twisted Intramolecular Charge Transfer Mechanism, or the like, where fill or partial like-charged groups on the fluorophore, or elsewhere in the biosensor molecule, favor the maximization of the separation of the charged groups. Thus, when glucose binds to the boronate binding site of embodiments of the biosensor molecules of the invention the boron atom's electronic properties change, allowing this group to modulate electrons density through bonds which may somewhat neutralize the effects at or near the fluorophore where multiple positively charged species have developed.

Figure 4:
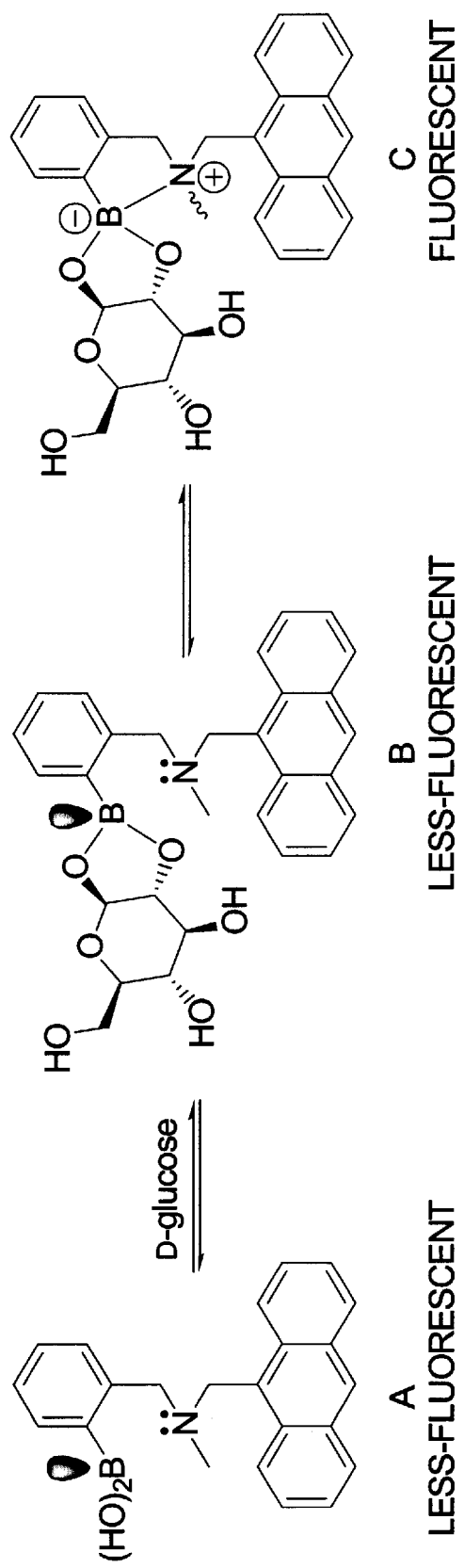
FIG. 4 provides a scheme showing the binding of glucose to AB and the proposed B-N interaction.

Current in vitro optochemical sensors detect and determine polyol concentration in different manners (see, e.g. James, T. D.; Sandanayake, K. R. A. S.; Shinkai, S. *Angew. Chem. Int. Ed. Engl.* 1996, 35, 1910–1922 and references therein). For example, displacement of bound dyes by analyte binding (see, e.g. Hamachi et al., *J. Am. Chem. Soc.* 2000, 122, 12065–12066; Ballerstadt et al., *Anal. Chem.* 2000, 72, 4185–4192; McSharie et al., *IEEE Engineering in Medicine and Biology* 2000, 36–45; Ueno, A. *Supramolecular Science* 1996, 3, 31–36), binding of analytes to cryptands (see, e.g., Král, V.; Rusin, O.; Schmidtchen, F. P. Organic Letters), fluorescence quenching upon analyte binding (see, e.g. Torimura et al. *Analytical Sciences* 2001, 17, 155–160.) and fluorescence enhancement upon analyte binding (see, e.g. James et al., *J. Am. Chem. Soc.* 1995, 117, 8982–8987; James et al., *Chem. Commun.* 1997, 71–72; Ward et al., *Chem. Commun.* 2000, 229–230; 1, Kijima et al., *Chem. Commun.* 1999, 2011–2012; Czarnik, A. W. *Acc. Chem. Res.* 1994, 27, 302–308; Yoon, J et al al., W. *SPIE* 1992, 1796, 87–91; Tong et al., *Anal. Chem.* 2001, 73, 1530–1536; Eggert et al., *J. Org. Chem.* 1999, 64, 3846–3852; Wang et al., *Org. Letters* 1999, 1, 1209–1212; Luis et al., *Analyst* 1998, 123, 155–158; Ilukrer et al., *Tetrahedron Letters* 1999, 40, 9125–9128; Appleton et al., *Sensors and Actmators B* 2000, 65, 302–304; Adhikiti et al., *Tetrahedron Letters* 1999, 40, 7893–7896; Patterson et al., *Tetrahedron Letters* 1997, 38, 6323–6326). Several optochemical systems measure analyte concentration resulting from fluorescent changes mediated by transient boronate ester formation (see, e.g. James et al., *Angew. Chem. Int. Ed. Engl.* 1996, 35, 1910–1922 and references therein). More specifically, formation of such boronate species in anthracene boronate (AB) systems causes suppression of photoinduced electron transfer (PET), the mechanism by which analyte concentration attenuates fluorescence intensity (see, e.g. James et al. *Angew. Chem. Int. Ed. Engl.* 1996, 35, 1910–1922 and references therein). For example, as illustrated in FIG. 4, free boronate A fluoresces less intensely than C because the amine lessens anthracene's fluorescence intensity by virtue of partial quenching by the lone pair on nitrogen. When an analyte, such as glucose, binds the boronic acid to yield B, the amine still quenches anthracene's fluorescence. When the amine interacts with the boronate, as seen in compound C, anthracene's fluorescence intensity increases because of suppression of PET according to current mechanistic theory. While FIG. 4 outlines a likely mechanism for most boronate-based optochemical saccharide sensing systems, the literature contains many examples of molecules that presumably operate via mechanisms outside of traditional PET mechanisms.

Figure 5:
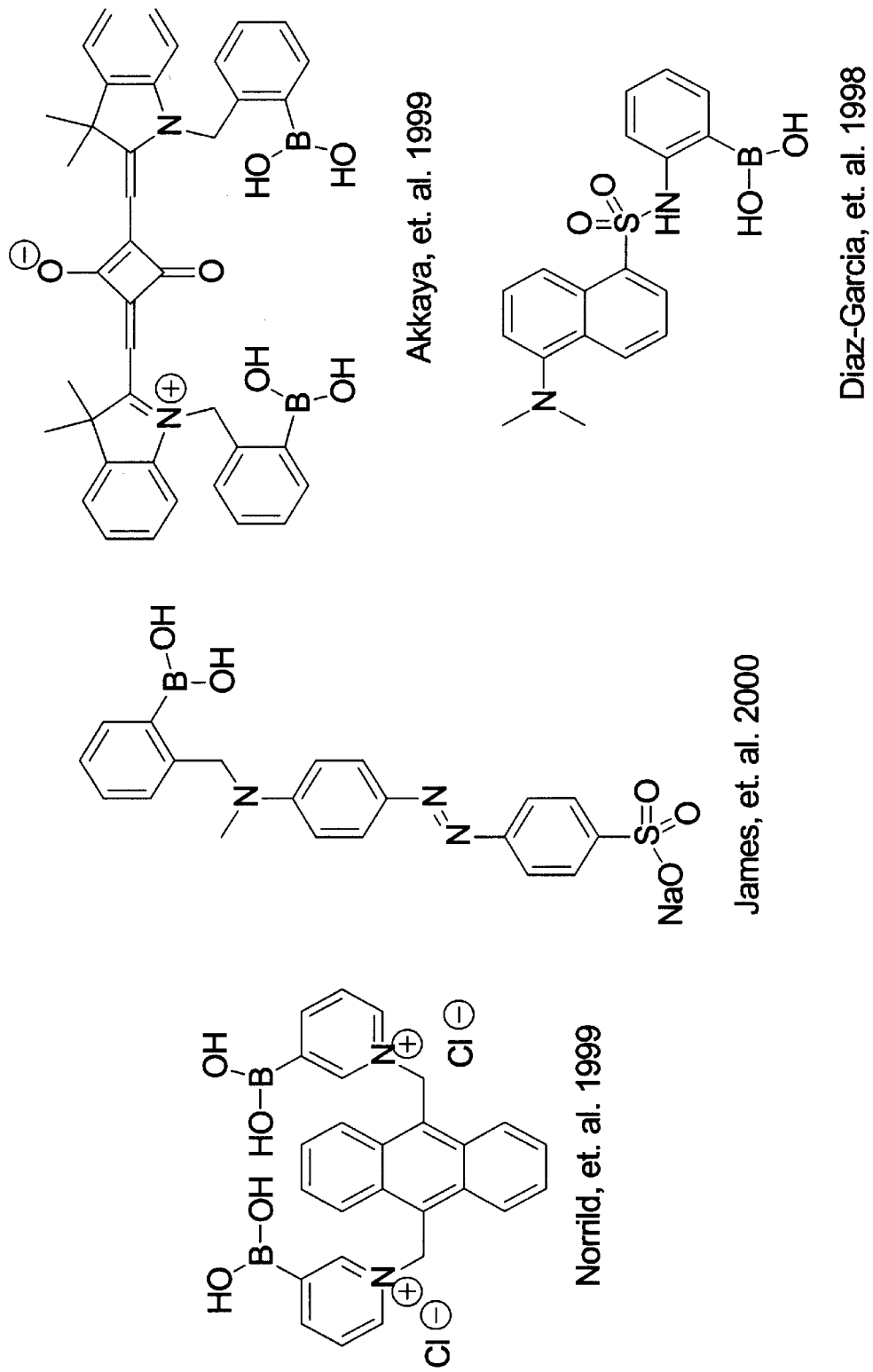
FIG. 5 provides examples of glucose sensing molecules.

In addition to Shinkai's anthracene boronate systems, the art describes several saccharide-sensing molecules that display other architectures (see, e.g. FIG. 5). The ditopic receptor synthesized by Eggert, et. al. contains a pyridium boronic acid moieties capable of binding glucose. This ditopic system contains no benzylic amine within its framework. James and coworkers demonstrated that their diazo-based colorometric system, which contains an anilinic nitrogen rather than a benzylic amine, also successfully transduces glucose perhaps via a different mechanism. Akkaya et al's near IR optochemical glucose sensor employs amines contained in an indolenine framework containing one benzyl amine and one benzyl imine. Diaz-Gracia et al's molecule contains a sulfonamide-boronic acid moiety for detecting saccharides. Clearly, these glucose-sensing molecules operate under mechanisms that do not necessarily employ PET. In fact, Norrild, James and Akkaya make no claim to PET as the mechanistic means for fluorescence modulation with increasing saccharide concentration in their molecules. These examples illustrate the function of saccharide sensing without the PET paradigm. The glucose transducing ability of molecules described by James, for instance, derive presumably from a twisted intramolecular charge transfer (ICT) mechanism. This mechanism differs from the PET mechanism and typically results in systems with poorer changes in fluorescent intensity.

The molecules known in the art have several significant drawbacks. While Norrild's system preferentially binds glucose over fructose with excellent changes in fluorescent intensity, the potential instability of the pyridinium moiety in aqueous solutions prevents this molecule from potential biological applications. Additionally, the low emission wavelength ($\lambda$=430 nm) supplants using this molecule for transdermal glucose interrogation. James' system operates best at pH 11 and not at physiological pH of 7.4. Also, the emission wavelength of James' molecules shifts to lower nanometers upon analyte binding, again making transdermal glucose interrogation even more difficult. Akkaya's system wonderfully transduces glucose at 645 nm in water thus obviating transdermal interrogation concerns, however, poor Stokes shifts between the excitation and emission wavelengths complicate accurate fluorescence measurements. The sulfonamide-based saccharide system built by Diaz-Garcia and others is highly selective for fructose, not glucose, and the fluorescence intensity decreased with increasing saccharide concentration thereby eliminating this system as a potential method for determining glucose concentrations in vivo.

In efforts to develop an optimized implantable long wavelength optochemical glucose sensor, several criteria are considered. These criteria include the use of a stable, biocompatible, water-soluble, long wavelength-based fluorophore matrix that increases in fluorescent intensity with increasing glucose concentrations. The issues of biocompatibility as well as some issues of water-solubility rely on choosing the appropriate polymer matrix. Other issues relate to the characteristics of the chosen fluorophore. Fluorophores that satisfied stability, long wavelength and fluorescence intensity concerns are highly preferable. Oxazine dyes can exhibit these properties.

Figure 2:
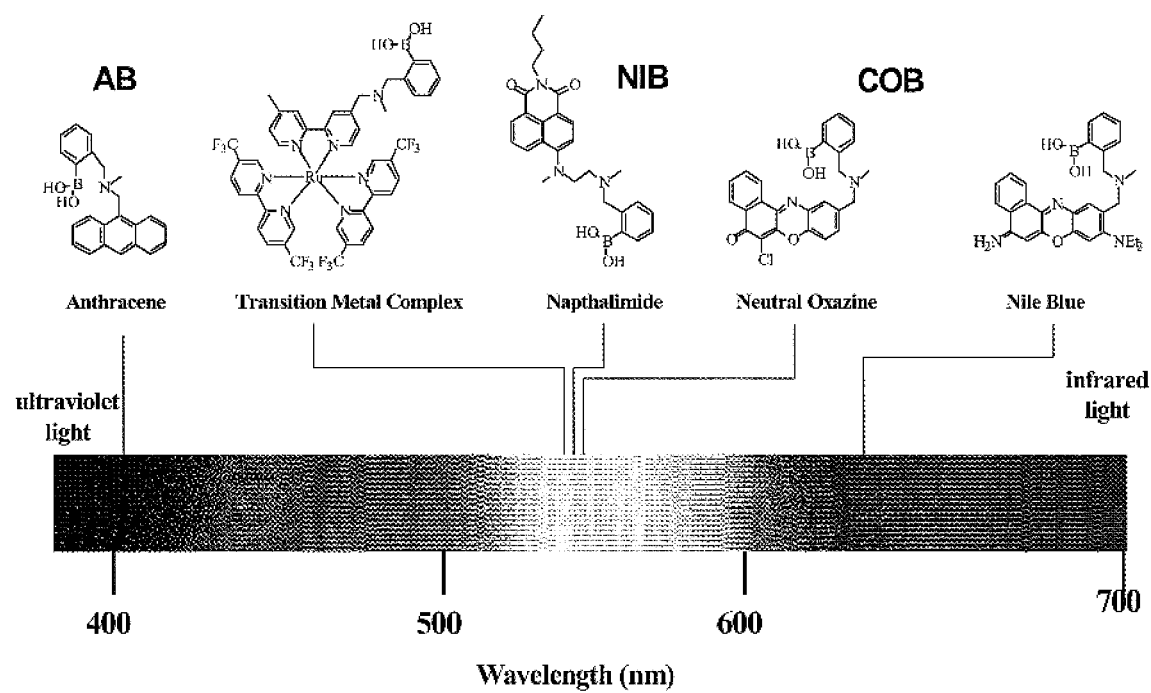
FIG. 2 provides a comparison of fluorescent excitations of representative fluorophores including the oxazine Nile Blue and illustrates the modular aspects of a number of switchable fluorescent polyhydroxylate sensors.
Figure 3:
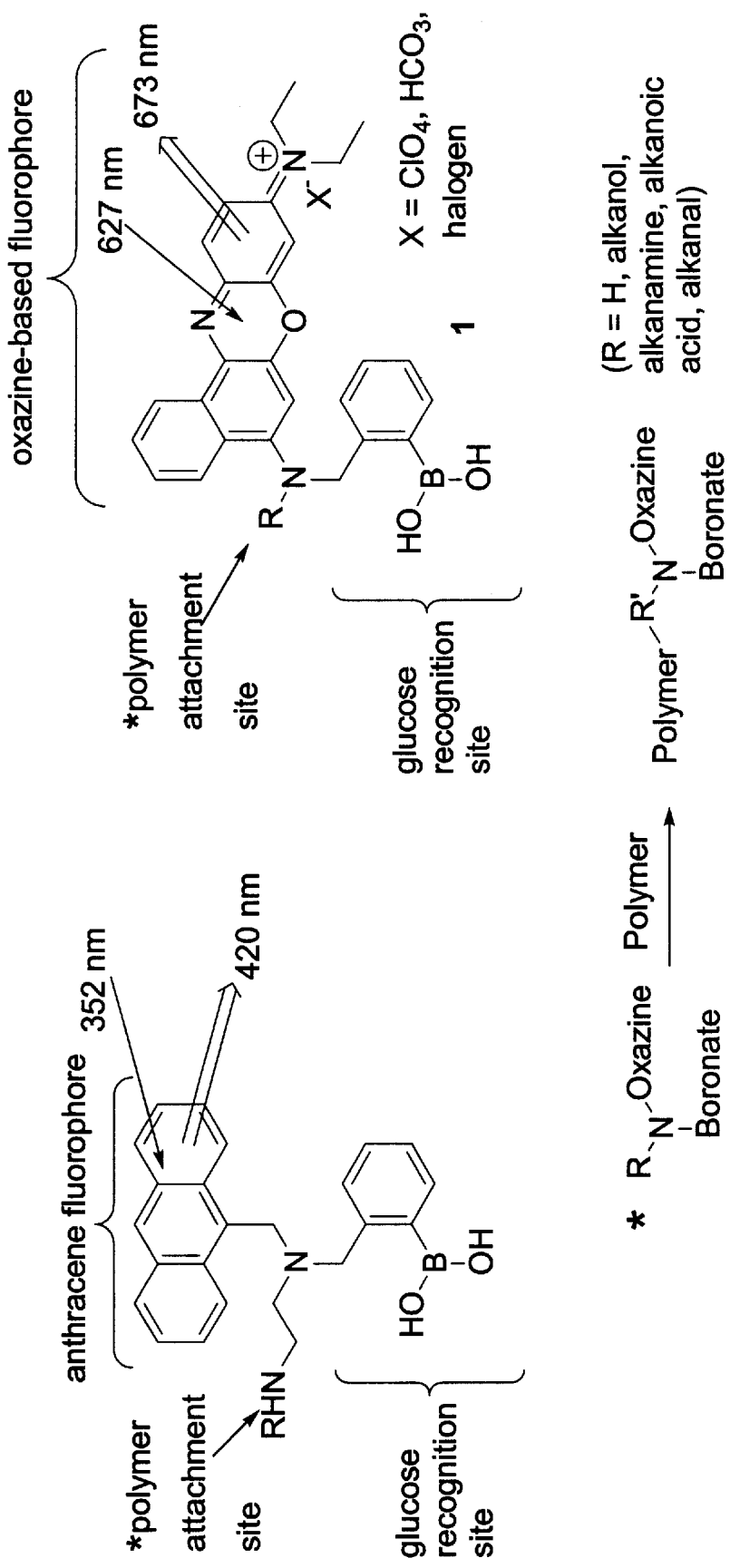
FIG. 3 provides a comparison of anthracene boronate-based glucose sensor with the Nile Blue boronate-based long-wavelength glucose sensor.

Exemplary long wavelength glucose-sensing molecule containing an oxazine (Nile Blue) coupled with a phenyl boronate suitable for detection of glucose, following polymer incorporation, in vivo is shown in FIGS. 2 and 3. FIG. 2 provides a comparison of fluorescent excitations of representative fluorophores including the oxazine Nile Blue. The excitation and emission profile of anthracene based compounds are well below that of Nile Blue's fluorescent profile (see, e.g., FIG. 3). Additionally, anthracene compounds can exhibit a limited solubility in water making its derivatives somewhat hydrophobic. In contrast, Nile Blue is highly soluble in water, due at least in part to its charged iminium ion, making its derivative more hydrophilic and possibly more compatible with in vivo conditions. From these standpoints, Nile Blue is a superior fluorophore for use in glucose sensing molecules. It is feasible to substitute other oxazines of similar structure for Nile Blue.

Figure 6:
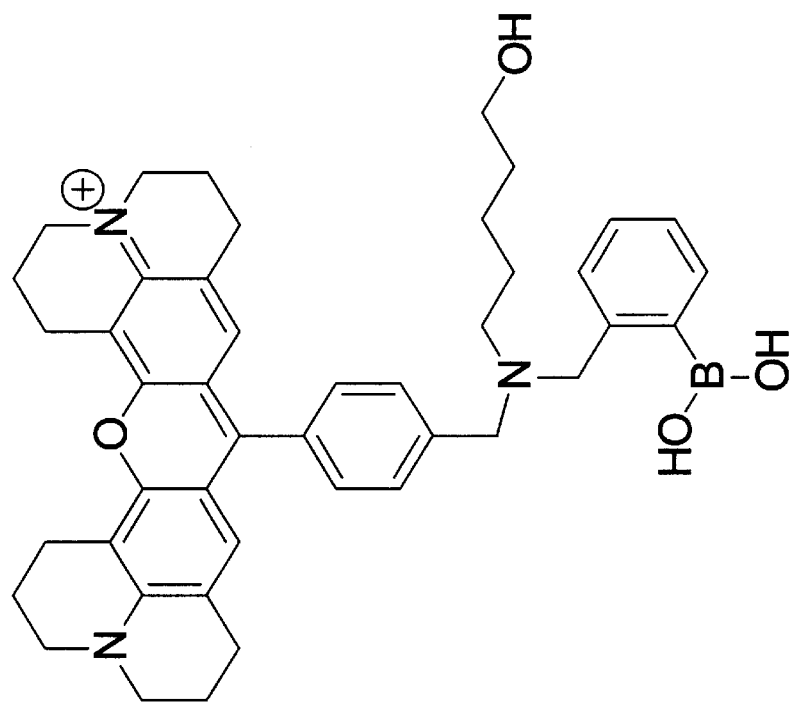
FIG. 6 shows COB and MitoTracker Red based boronates for glucose sensing.
Figure 6:
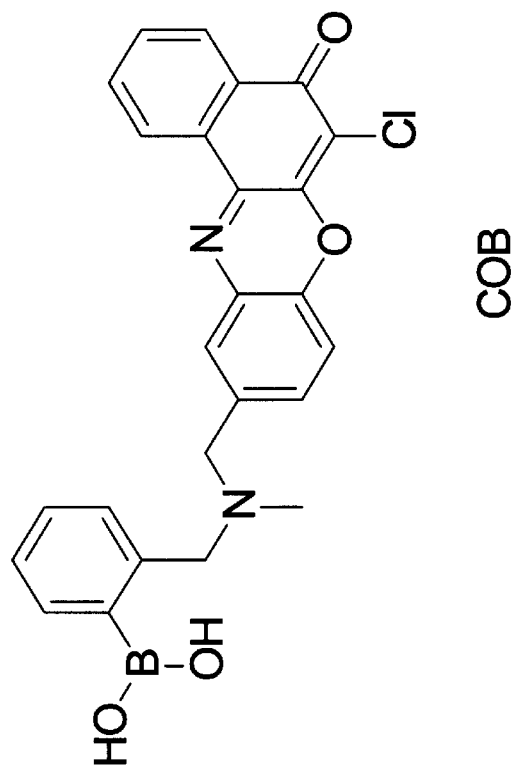

Oxazine dyes are water soluble, highly fluorescent, long wavelength molecules possessing a characteristic fused aromatic, heterocyclic ring system. Based on these requirements, oxazine-based chlorooxazine boronate (COB) became a focus of initial synthetic efforts (FIG. 6). The synthesis of COB took 5 steps with an overall yield of 11.5%. While COB beautifully transduced glucose in MeOH, this was not the case in significantly aqueous systems. COB may be made more hydrophilic via the methods disclosed herein (e.g. by tethering COB to hydrophilic polymers such as PEG).

Despite changing the structural diversity of target compounds, preferred systems include a water-soluble and long wavelength-based fluorophore that increases in fluorescent intensity with increasing glucose concentrations. In the context of the fluorophores described herein, an oxazine-based fluorophore was employed which used an anilinic amine as the boronate attachment point rather than incorporating a benzylic amine as was the case with the COB based polyhydroxylate sensor (FIG. 7). This scaffold's new design differs from all other reported scaffolds. The highly conjugated polyene iminium framework remains unique to the design of the molecules disclosed herein. This design also incorporates a boronate for glucose recognition and a polymer attachment site on the amine. While this molecule relies on an anilinic amine, the conjugation of the oxazine molecule drastically differs from James' diazo molecule. The system disclosed herein does not compare to Akkaya's system because the disclosed systems lack two boronates and an indolenine framework. No examples existed before the conception of this design which would help to assure that favorable transduction results would be obtained. The long wavelength emission generated from the desired fluorophore however, overcomes drawbacks related to poor transduction.

Figure 8:
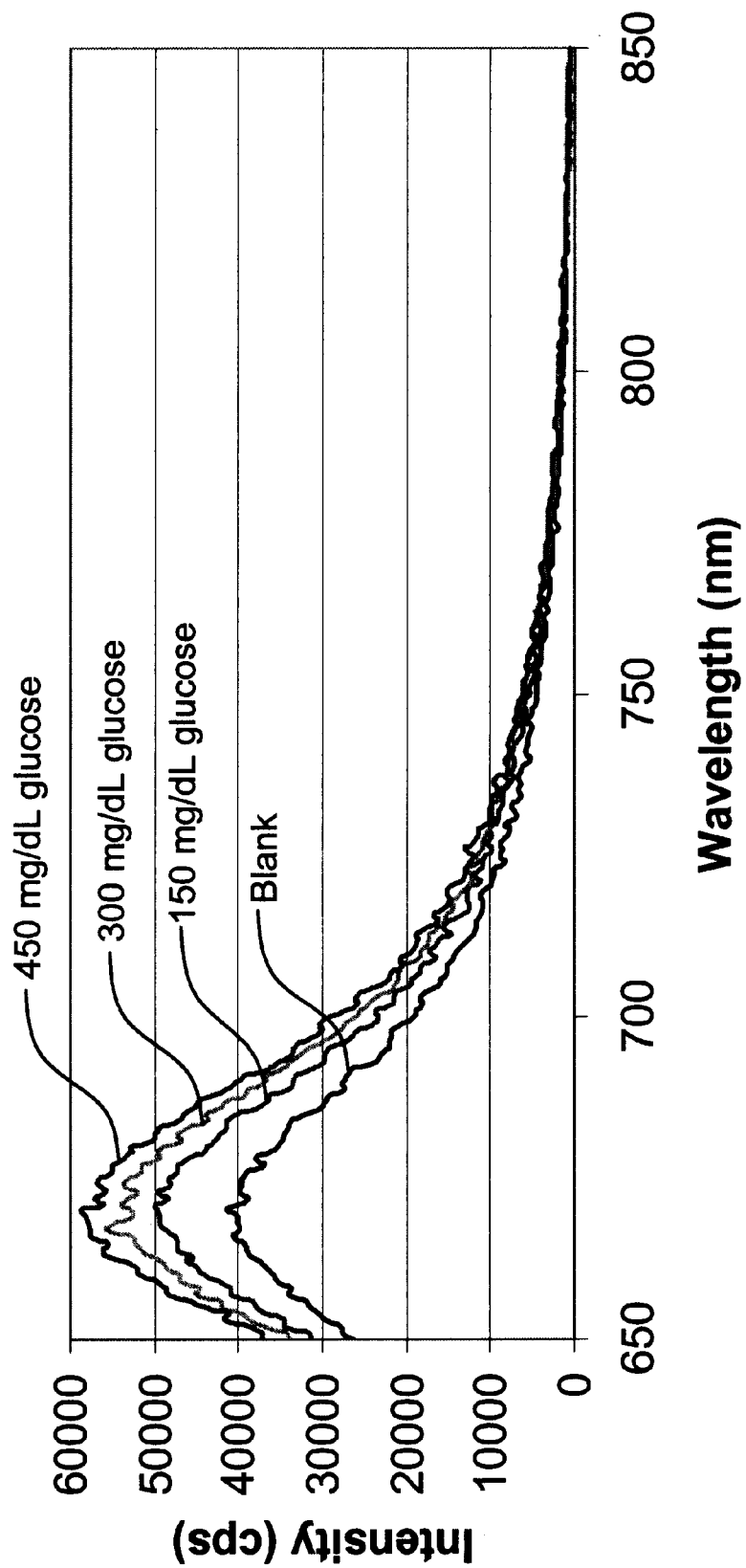
FIG. 8 provides illustrative fluorescent data from a Nile Blue (NBB) glucose transduction experiment.

A typical embodiment of the invention uses Nile Blue as an illustrative oxazine-based fluorophore. In typical experiments with this molecule, at various glucose concentrations (0 mg/dL, 150 mg/dL, 300 mg/dL and 450 mg/dL), the fluorescent intensity of Nile Blue Boronate (NBB) increased 25%, 35% and 40% at 150 mg/dL, 300 mg/dL and 450 mg/dL at 671 nm (see, e.g., FIG. 8). These percent increases in fluorescent intensity rival those seen with AB under the same conditions. Moreover, unlike COB, NBB transduces glucose exceptionally well in water. Additionally, no blue shift in fluorescence intensity occurred as was seen in James' glucose sensors, which operate by TICT. The large Stokes shift in NB allows for irradiation at 621 nm and detection at 671 nm thereby cleanly separating excitation and emission wavelengths, a concern raised in Akkaya's system. Because there is no shifting of fluorescence intensity of NBB when bound to glucose and the concentration of NBB is less than 10 $\mu$M, there are no FRET-based contributions to changes in fluorescent intensity. This is the first known example of an oxazine-based optochemical sensor that transduces glucose in substantially aqueous systems at a wavelength greater than 650 nm whose change in fluorescence intensity appears to operate independent of traditional PET mechanisms.

Figure 9:
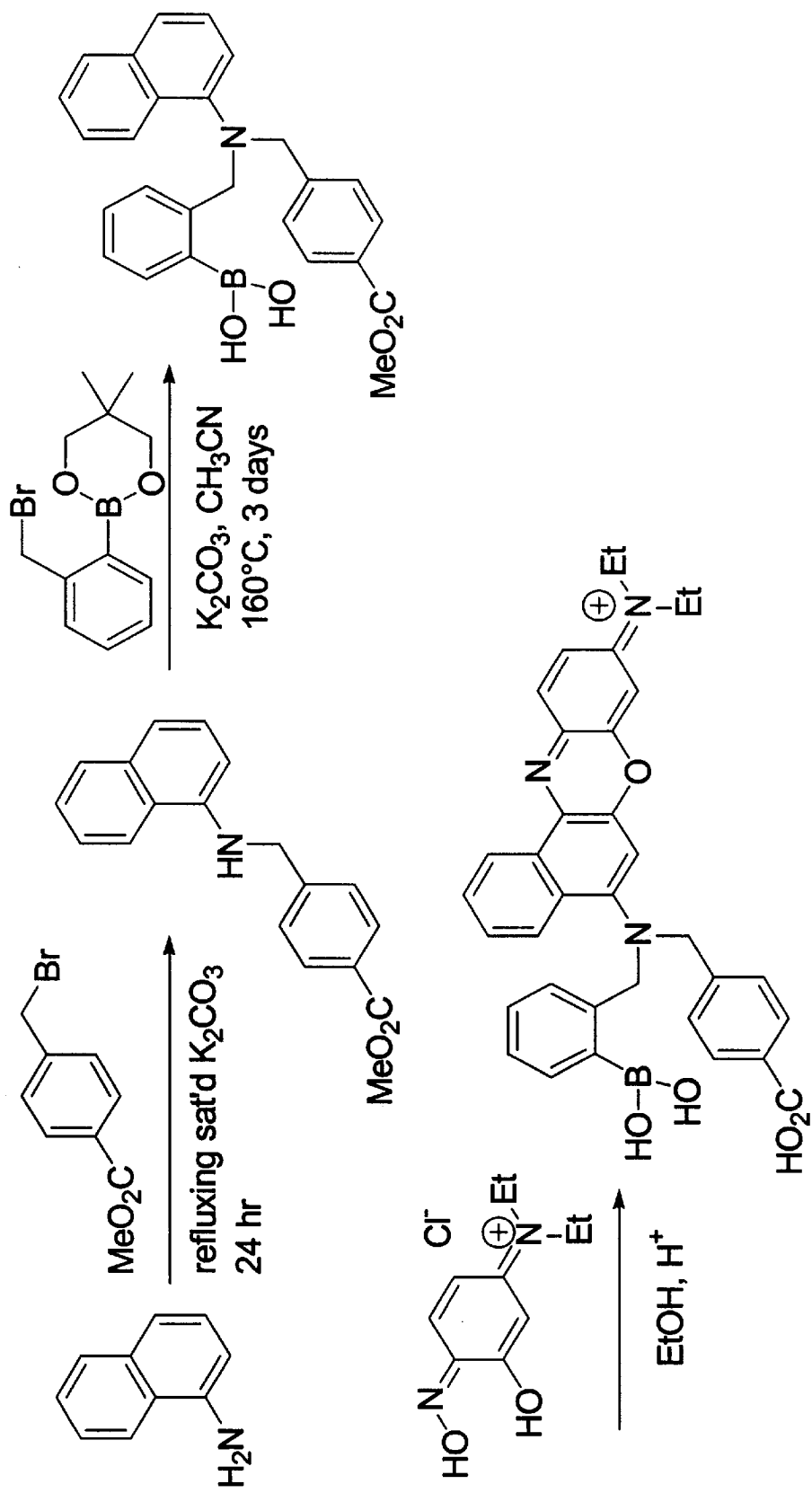
FIG. 9 outlines a scheme for building NBB with a benzoic acid linker suitable for attachment to polymers such as poly(vinyl alcohol).
Figure 10:
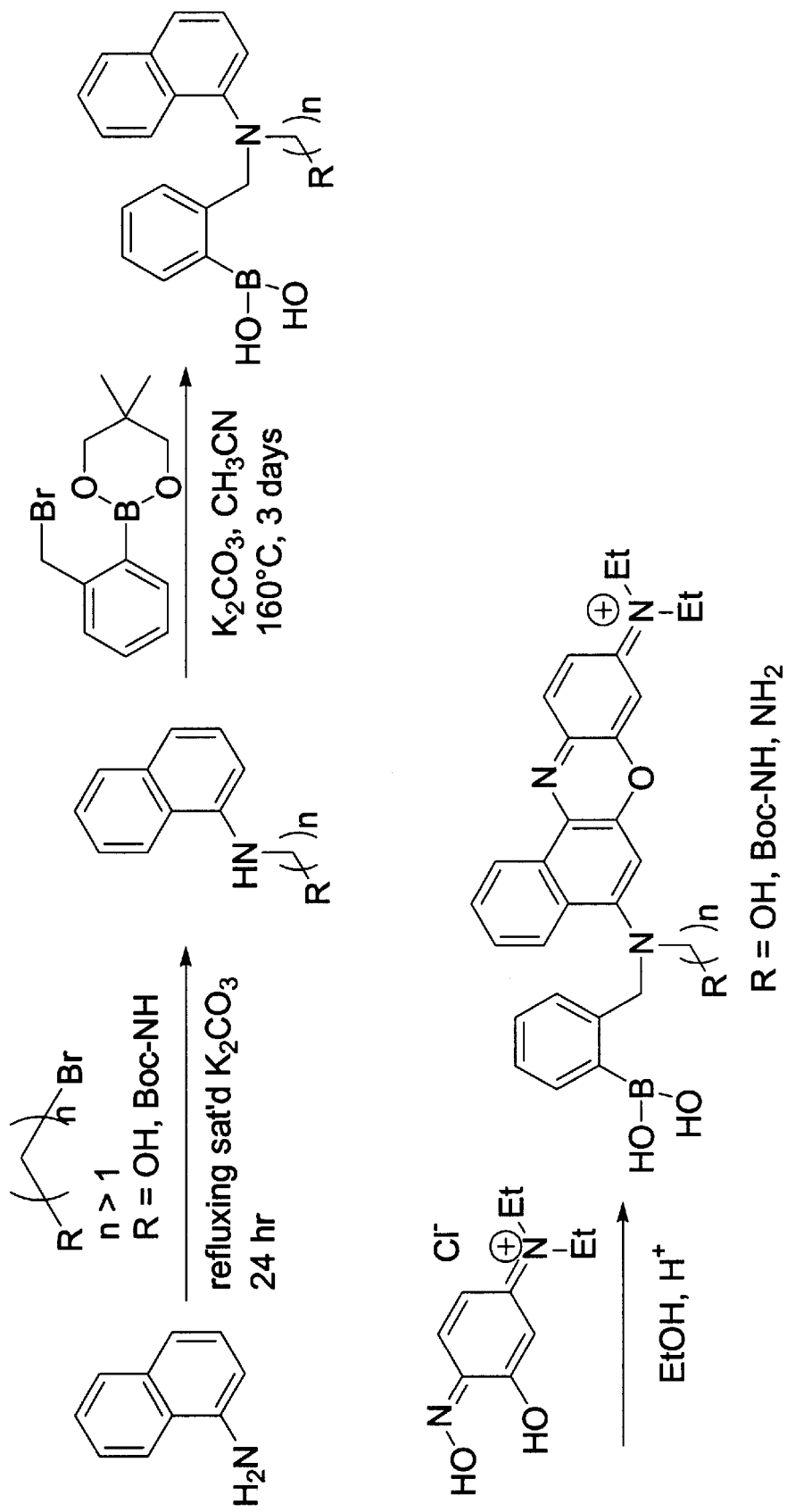
FIG. 10 provides a scheme showing the synthesis of hydroxyl- and amino-terminated linkers in NBB.
Figure 11:
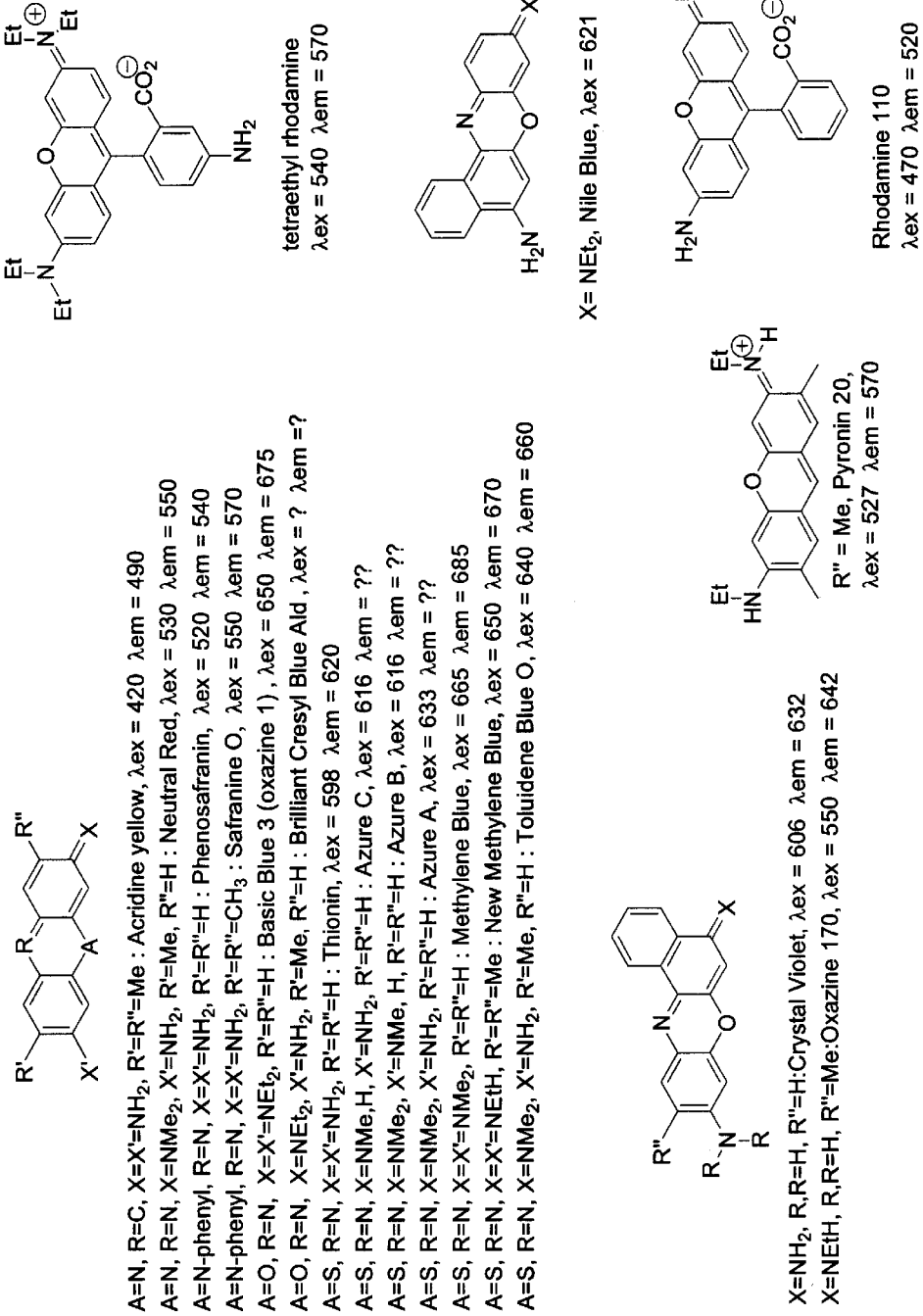
FIG. 11 provides common fluorophores containing salient features of glucose transducing boronates.
Figure 12:
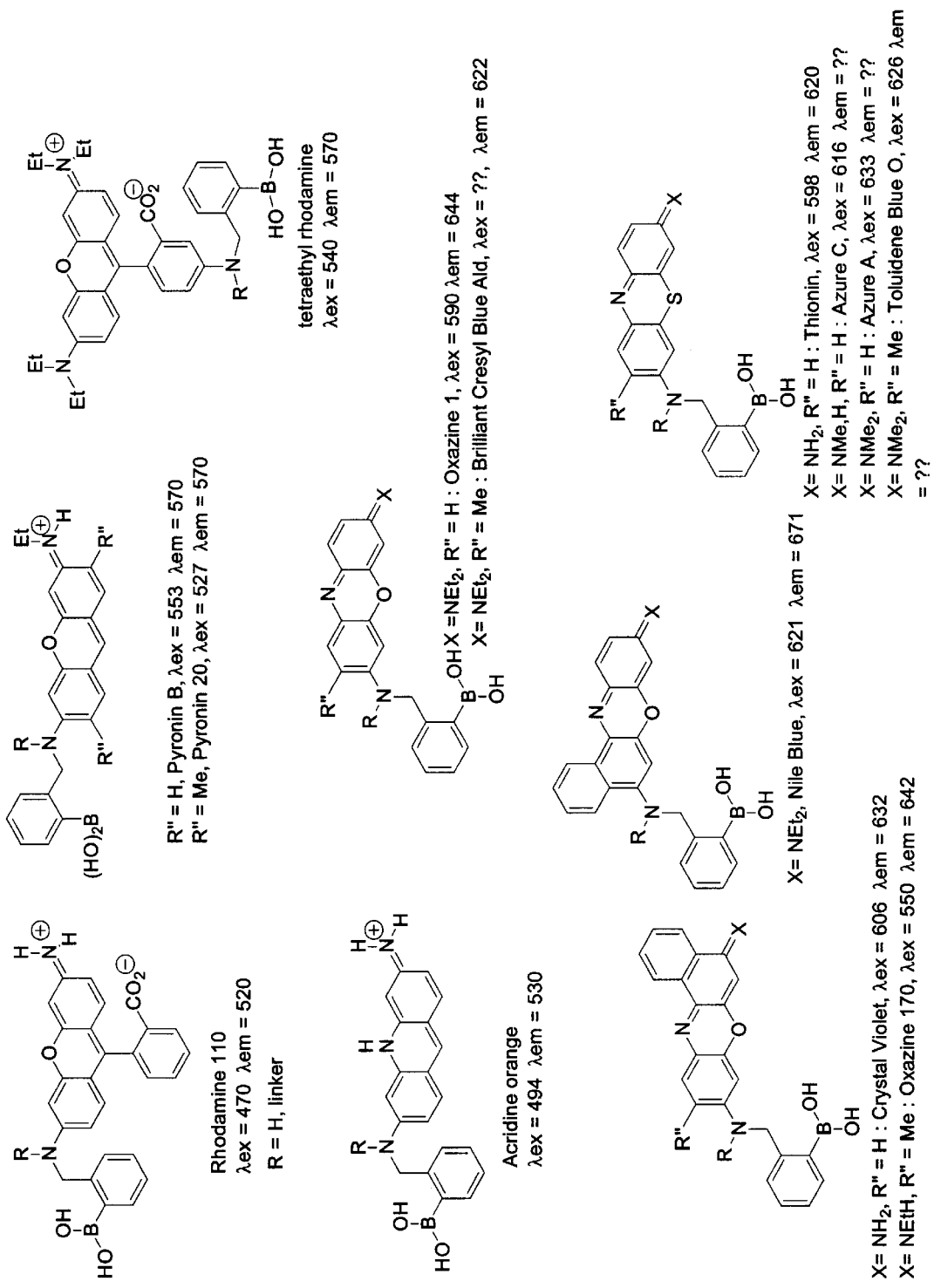
FIG. 12 provides examples of boronate derivatized fluorophores.
Figure 13:
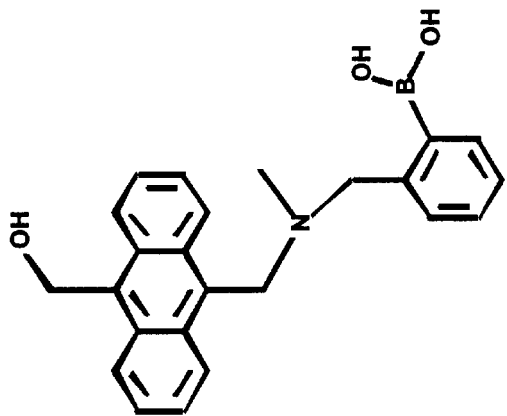
FIG. 13 illustrates approaches developed for tethering an anthracene-boronate sensing molecule (AB) to a polymer wherein a linker segment is attached at different sites on AB that preserve glucose transduction and fluorescence. Shown from left to right is AB, a first linker scheme and a second linker scheme.
Figure 13:
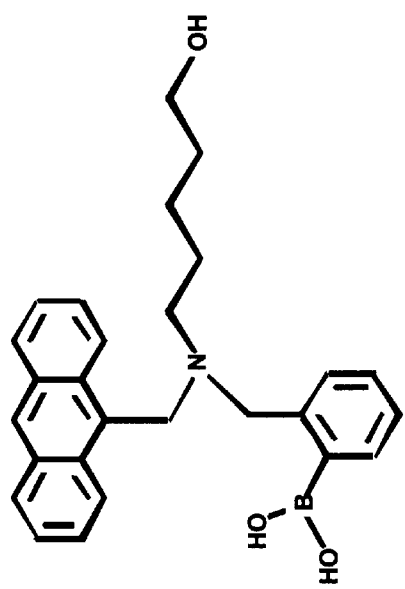
Figure 13:
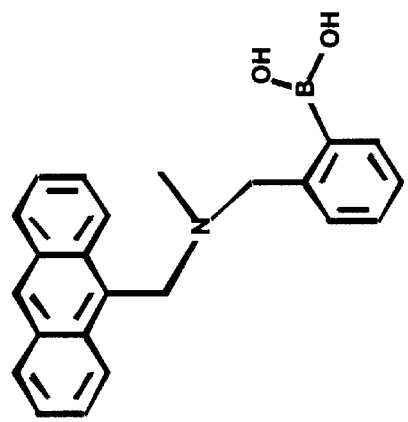

Embodiments of the invention can be made by a variety of traditional chemical synthesis techniques. Illustrative syntheses of Nile Blue Boronate containing various linkers for suitable polymer attachment are outlined in FIG. 9 and 10 and the Examples herein. FIG. 9 outlines a scheme for building NBB with a benzoic acid linker suitable for attachment to nucleophilic-based polymers such as poly(vinyl alcohol). FIG. 10 outlines a scheme for building NBB with a hydroxy- or amino-terminated linker suitable for attachment to an electrophilic-based polymer such as poly(acrylic acid). Several new fluorophores suitable for derivatization into optochemical glucose sensors are shown in FIGS. 11 and 12.

Figure 18:
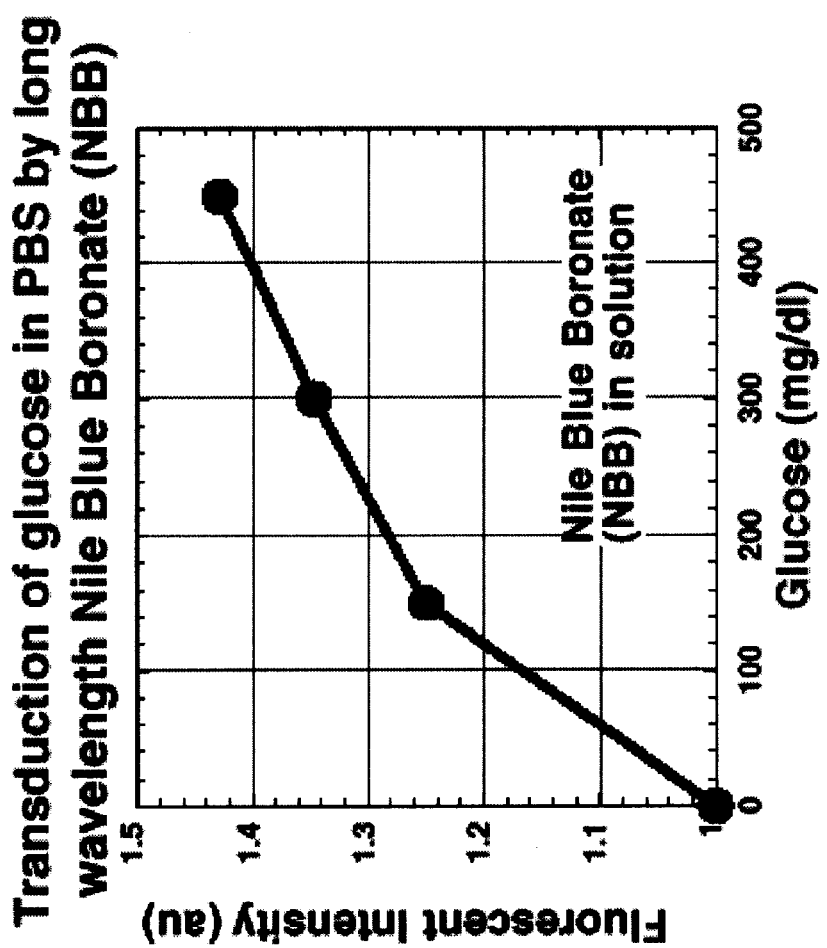
FIG. 18 is a graph showing Nile Blue boronate's transduction of glucose in PBS.

The figures provided herein further illustrate various embodiments of the invention and their properties in order to further facilitate artisans' making and using the invention. For example, using the graphic format provided in FIG. 18, experiments confirming properties of Nile Blue were performed with the following results:

| glucose (mg/dl) | relative fluorescent intensity |
|---|---|
| 0 | 1.0 |
| 150 | 1.085 |
| 300 | 1.239 |
| 450 | 1.398 |
| 1000 | 1.513 |

Artisans will understand that various embodiments of the invention may be analyzed in an analogous manner. In addition, those skilled in the art will be able to utilize a variety of protocols known in the art to generate various embodiments of the invention disclosed herein.

Generalized biosensor molecules in accordance with embodiments of the invention include three components: (1) an oxazine-based fluorophore that includes at least one conjugated charged moiety (e.g. an iminium ion), (2) a linker moiety, which typically includes an anilinic group in relation to the fluorophore, and (3) a boronate substrate recognition/binding moiety, which binds to polyhydroxylate analytes, such as glucose. These biosensor molecules further include a "switch" or "response" element that is drawn from electronic interactions that involve these components.

This switch element is an integral component of the polyhydroxylate analyte sensing mechanism, i.e., transduction ability, of the biosensor molecules in accordance with embodiments of the present invention that serves to effectively "switch off" the fluorescence of the oxazine-based fluorophore in the absence of bound polyhydroxylate analyte. Thus, in the absence of polyhydroxylate analyte binding, e.g., glucose binding, the oxazine-based biosensor molecules in accordance with embodiments of the invention exhibit excited states of the fluorophore that are essentially quenched by the switch element. On the other hand, in the presence of a polyhydroxylate analyte fluorescence is greatly enhanced from the low level background levels that can be observed in the absence of analyte. Consequently, the binding of a polyhydroxylate analyte, such as glucose, can be correlated with the ambient analyte concentrations via a change in fluorescence intensity (see, e.g. U.S. Pat. No. 6,002,954 which is incorporated herein by reference) and/or a change in fluorescence lifetimes (see, e.g. U.S. Pat. No. 5,246,867, and U.S. patent application Ser. No. 09/826,745 which are incorporated herein by reference).

For embodiments of the oxazine-based biosensor molecules of the invention, the fluorescent switch element generally includes the boron atom of the substrate recognition moiety and the heteroatom of the linker moiety, preferably a nitrogen atom, but also includes the fluorophore in its electron-accepting capacity. This fluorescent switch is generally "off" in the absence of bound polyhydroxylate analyte and is generally "on" in the presence of bound polyhydroxylate analyte. Thus, the reversible binding of a polyhydroxylate analyte essentially turns the fluorescent switch "on" and "off". Although in the case of particular oxazine-based biosensor molecules, this switching function is not an "all or none" phenomenon, as a certain level of background fluorescence may be observed in the absence of polyhydroxylate analyte.

As shown in FIG. 1, a generalized oxazine-based biosensor molecule in accordance with embodiments of the invention includes an oxazine-based fluorophore denoted as F. In embodiments of the biosensor molecules of the invention, this oxazine-based fluorophore is the core fluorophore upon which substituents can be added to achieve desired electronic and/or chemical properties of a particular biosensor molecule. For example, substituents can be added that effect the absorption and emission wavelengths, the quantum yield and/or the fluorescence lifetimes of particular embodiments of the oxazine-based biosensor molecules. Additionally, substituents may be added that affect the solubility of the biosensor molecule and/or provide functionality that can be coupled to other molecules, such as a polymer matrix.

The substrate recognition moiety of embodiments of the oxazine-based biosensor molecules is preferably provided by a phenylboronic acid moiety, namely, $(C_6H_5)B(OR^1)_2$, where $R^1$ is hydrogen, a lower aliphatic or aromatic functional group. Preferably, $R^1$ is hydrogen. However, other substituted boronic acids also may be used in embodiments of the biosensor molecules provided that upon polyhydroxylate binding the electronic effects at the boron atom are not adversely affected so as to alter the fluorescent properties of the resultant biosensor molecule, as noted above.

In preferred embodiments of the oxazine-based biosensor molecules include a phenylboronic acid that is covalently bonded to an optional linkage, $L^1$, which is part of the linker moiety. This configuration is illustrated schematically in FIG. 1. Besides the $L^1$ linkage, the linker moiety also includes a heteroatom, labeled as Z, preferably a nitrogen, however, the linker moiety may include a different electron-donating atom, such as oxygen, sulfur or phosphorous. The linker moiety further includes a second optional linkage, $L^2$, which provides a linkage to the oxazine-based fluorophore. The linkages $L^1$ and $L^2$ ate each generally 0–4 contiguous atoms selected from carbon, oxygen, nitrogen, sulfur, and phosphorous, and preferably are simple alkyl chains where n=0, 1, 2, 3, 4, 5, 6, 7, 8, or the like. Additionally, preferred linkers may contain polyethylene oxide (PEO), hydroxy alkyl and amino alkyl groups. Optional groups $R^2$, $R^3$ and $R^4$ are attached respectively to the phenyl group, the heteroatom of the linker moiety, and the fluorophore. These optional groups may be functional groups that achieved desired electronic effects or that can form covalent linkages to a polymer matrix, or the like. In preferred embodiments, $R^3$ forms a covalent linkage to a polymer matrix. Alternatively, $R^2$, $R^3$ and $R^4$ may be hydrogen, an aliphatic, aromatic, acidic, $—NH_2$, $—OH$, SH, or NCO functional group.

In a highly preferred embodiment of the oxazine-based biosensor, the linkage $L^1$ consists of 1–2 (most preferably 1) carbon atoms and the linkage $L^2$ consists of 0 (most preferably) or 1 carbon atom. Additionally, preferred linkers may contain polyethylene oxide (PEO), hydroxy alkyl and amino alkyl groups. As noted above, in these molecules, optional groups $R^2$, $R^3$ and $R^4$ are attached respectively to the phenyl group, the heteroatom of the linker moiety, and the fluorophore. These optional groups may be functional groups that achieved desired electronic effects or that can form covalent linkages to a polymer matrix, or the like. Alternatively, $R^2$, $R^3$ and $R^4$ may be hydrogen, an aliphatic, aromatic, acidic, $—NH_2$, $—OH$, SH, or NCO functional group.

In preferred embodiments of the invention disclosed herein, F emits at a wavelength greater than about 500 nm, a wavelength greater than about 550 nm, a wavelength greater than about 600 nm or a wavelength greater than about 650 nm. In highly referred embodiments, the excitation wavelength for F is greater than about 550 nm, 600 nm or greater than about 625 nm. In this context, those skilled in the art understand that the excitation and emission wavelengths of such molecules are found over in a focused spectrum of wavelengths and do not occur at a single absolute point. Consequently, with molecules that, for example, have an emission maximum centered near 675 nm, it is therefore accurate to describe such molecules as typically emitting at a wavelength greater than about 675 nm. In addition, with molecules that, for example, have an excitation maximum centered near 625 nm, it is therefore accurate to describe such molecules in such terms as having an excitation wavelength that is greater than about 625 nm. For a general description of the properties of fluorescent molecules and fluorescent techniques, see "Introduction to Fluorescence Techniques" from the Handbook of Fluorescent Probes and Research Chemicals, portions of which can be found online at http://www.probes.com (specifically at http://www.probes.com/handbook/sections/0069.html).

Preferred embodiments of sensor molecules having a specific molecular formula as shown in FIG. 1 are those where the excitation wavelength for F is greater than about 600 nm. Such embodiments have a number of advantages over similar previously described molecules. For example, such molecules have the advantage of being excited at a wavelength outside of the ultraviolet spectra, and therefore are particularly suited for use in, for example, subdermally implanted optical glucose monitoring systems (See e.g. U.S. Pat. No. 6,011,984). In particular, ultraviolet light, which has a spectrum that extends up to, but not beyond 400 nm, is known to be able to induce cumulative damage to human skin (see e.g. Lavker et al., J. Invest. Dermatol., 108(1): 17–21 (1997) and Gasparro Environ. Health Perspect, 108 Sppl. 1: 71–78 (2000)). Consequently sensors designed to function with fluorophores having excitation wavelengths outside of this range can avoid potential problems associated with the use of fluorophores having excitation wavelengths which fall within a range that, in certain contexts, has been shown to induce cumulative damage to human skin. Moreover, because the matching of the peak excitation wavelength with an existing light source (such as an LED or diode laser) facilitates the generation and use of embodiments of the invention including their use in transdermally implanted glucose monitors, excitation wavelengths for F greater than about 400 nm have this additional advantage over similar previously described molecules.

Preferred embodiments of sensor molecules having a specific molecular formula as shown in FIG. 1 are those where the emission wavelength for F is greater than about 650 nm have a number of other advantages over similar previously described molecules, particularly in their ability to transmit a signal through a tissue such as skin. Specifically, the transmission through a few millimeters of skin increases logarithmically with wavelength—from 0.1% at 400 nm to almost 100% at 850 nm (see e.g. Optical-Thermal Response of Laser-Irradiated Tissue (A. J. Welch and M. J. C. van Gemert eds., Plenum Press) (1995); Francis A. Duck, Physical Properties of Tissue (Academic Press) (1990) and Abraham Katzir, Lasers and Optical fibers in medicine (Academic Press) (1993). Thus, the longer the wavelength, the greater the transmission through skin. Because of the significant increase in optical skin transmission at longer wavelengths, a practical glucose sensor using the fluorescent molecules described herein can operate more efficiently, more accurately, and with a greater signal-to-noise ratio.

The generation of various embodiments of the invention disclosed herein may be facilitated by an understanding of certain electrochemical aspects of any potential donor-acceptor pair. For example, the free energy of PET ($\Delta G_{el}$) can be calculated using the Rehm-Weller equation shown below:

$$\Delta G_{el}(\text{kcal mol}^{-1})=23.06[E^0(D^+/D)-E^0(A/A^-)]-w_p-w_r-\Delta G_{00}$$

where $E^0(D^+/D)$ is the oxidation potential of the donor, $E^0(A/A^-)$ is the reduction potential of the acceptor, and $\Delta G_{00}$ is the free energy corresponding to the equilibrium energy $E_{00}$ (see e.g. Kavarnos, G. J. In *Fundamentals of photoinduced electron transfer*, VCH Publishers: New York, N.Y., 1993; p Chapter 1 and Rehln and Weller, Isr. J. Chem. 1970, 8, 259). The quantities $w_p$ and $w_r$ are Coulombic terms for the products and reactants, and are found to be small in polar solvents. To simplify predictions, assume $w_p$ and $w_r$ to be zero, and estimate $E_{00}$ as the energy corresponding to $[\lambda_{max}(\text{ex})+\lambda_{max}(\text{em})]/2$ for each fluorophore. While accurate $E_{00}$ values can also be found for example, in the literature for anthracene and a number of other compounds, this method of calculation is useful for estimating equilibrium energies for new compounds that have not been previously reported.

Consequently, to generate various embodiments of the present invention, the thermodynamic requirement of the system that can be met is adherence to a simplified version of the Rehm-Weller equation as follows:

$$\Delta G_{PET}=23.06[E^0(Z^{oxidation})-E^0(F^{reduction})]-\Delta E_{00},$$

where $\Delta G_{PET}$ is the standard free-energy change for electron transfer, $E^0(Z^{oxidation})$ is the oxidation potential of the switch (typically an amine), $E^0(F^{reduction})$ is the reduction potential of the fluorophore, and $\Delta E_{00}$ is the energy of the excited state fluorophore. To design a compound with the desired fluorescent characteristics entails selecting a fluorophore F with the desired properties and simultaneously selecting a switch Z with an oxidation potential that results in a $\Delta G_{PET}$ that is less than about 3.0 kcal mol$^{-1}$. The electrochemical potentials can be measured using the individual molecular groups before assembling the complete molecule.

The above description of the oxazine-based biosensor molecules of the invention illustrate the modular nature of these biosensor molecules. This modular architecture provides building blocks for future design of other biosensor molecules. Moreover, as shown in the examples below, these oxazine-based biosensor molecules provide a reliable model for fluorescent biosensor molecule development, which represents an advantage toward creating polyhydroxylate reporter molecules that have at least one desired fluorescent property, for example, but not limited to, operating at longer wavelengths. The model, therefore, allows for systematic build-up (i.e., component by component) of new oxazine-based biosensor molecules in relatively simple steps.

The invention described herein has a number of embodiments. A preferred embodiment includes a fluorescent compound having a fluorophore including an iminium ion, an anilinic group in relation to the fluorophore, a boronate moiety capable of binding glucose and a linker moiety that links the fluorophore to the boronate binding moiety. In such embodiments, these fluorescent compounds exhibit an alteration in fluorescent properties when the boronate moiety is bound to glucose. These compounds typically emit a fluorescent signal in the visible to near infrared region of the spectrum that can be correlated to the presence of glucose in a substantially aqueous medium. In one embodiment, the excitation wavelength for the fluorophore is greater than about 600 nm. Preferably, the fluorophore of the compound has at least one maximum wavelength in an emission spectrum of the fluorophore that is between about 600 nm and about 800 nm. In highly preferred embodiments, the excitation wavelength for the fluorophore is greater than about 600 nm and wherein the compound is able to emit a fluorescent signal having a wavelength of greater than about 600 nm.

In a representative embodiment of the invention, the compound has the following general formula:

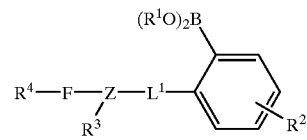

where F is a fluorophore including an iminium ion, B is a boron atom, $R^1$ is selected from the group consisting of hydrogen, aliphatic and aromatic functional groups, wherein the functional group $(R^1O)_2B$ is capable of binding glucose, $R^2$, $R^3$ and $R^4$ are optional and independent functional groups selected from the groups consisting of hydrogen, aliphatic and aromatic functional groups, further functionalized aliphatic and aromatic groups, functional groups that alter the electronic properties of the group to which they are attached and functional groups that are capable of forming covalent linkages to a polymer matrix, $L^1$ is an optional linking group having from zero to four atoms selected from the group consisting of nitrogen, carbon, oxygen, sulfur and phosphorous, and Z is a heteroatom selected from the group consisting of nitrogen (which is highly preferable), phosphorous, sulfur, and oxygen; wherein the heteroatom is in an anilinic-type relationship to the fluorophore. In such embodiments of the invention, the fluorescence of the compound increases in the presence of bound glucose.

In a related embodiment of the invention, the compound has the following general formula:

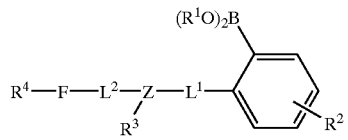

wherein F is a Nile Blue moiety, B is a boron atom, $R^1$ is selected from the group consisting of hydrogen, aliphatic and aromatic functional groups, wherein the functional group $(R^1O)_2B$ is capable of binding glucose, $R^2$, $R^3$ and $R^4$ are optional and independent functional groups selected from the groups consisting of hydrogen, aliphatic and aromatic functional groups, further functionalized aliphatic and aromatic groups, functional groups that alter the electronic properties of the group to which they are attached and functional groups that are capable of forming covalent linkages to a polymer matrix, $L^1$ and $L^2$ are optional linking groups having from zero to four atoms selected from the group consisting of nitrogen, carbon, oxygen, sulfur and phosphorous; and Z is a heteroatom selected from the group consisting of nitrogen, phosphorous, sulfur, and oxygen.

Another embodiment of the invention includes a ditopic biosensor molecule, the biosensor molecule including a first biosensor molecule (e.g. Nile Blue), a second biosensor molecule and a bridging linker element, wherein the bridging linker element forms a bridge between the first and the second biosensor molecules and wherein the first and second biosensor molecules are the same or different. In certain embodiments of the invention the bridging linker element includes 2–10 carbons. In preferred embodiments of the invention, the ditopic biosensor binds glucose below about 100 mg/dL of analyte and emits a detectable emission signal that correlates to the glucose binding below about 100 mg/dL. In other embodiments of the invention the ditopic sensor also binds glucose up to about 1000 mg/dL of analyte and emits a detectable emission signal that correlates with glucose binding up to about 1000 mg/dL of analyte.

In preferred embodiments of the invention, these compounds further include one or more functional groups selected from the group consisting of at least an aliphatic, an aromatic, a haloalkane, an alcohol, an ether, an amine, an imine, an aldehyde, a ketone, an ester, a carboxylic acid, a sulfonic acid a cyano group, a phosphoric acid, and salts. Typically, the hydroxyl, carbonyl, a carboxylic acid, carboxylate or amine functional group includes an aliphatic linker with 2 or more carbon atoms. In a representative embodiment, $R^3$ is a hydroxyl, carbonyl, a carboxylic acid, carboxylate or an amine functional group.

The disclosure provided herein allows the functional development and use of a novel oxazine-based long wavelength glucose-transducing sensor whose fluorescence and water solubility characteristics make it an ideal candidate for subcutaneous glucose quantification. This sensor has superior excitation and emission wavelengths, relative to anthracene, and is capable of penetrating human tissue for accurate and reliable fluorescence detection. Additionally, its ability to transduce glucose in substantially aqueous systems provides another key distinction between this glucose sensor and other known glucose sensors. Although this sensor is outside of conventional PET wisdom by means of its unique structure, transduction data compares favorably with AB suggesting fluorescence regulation outside of traditional PET mechanisms.

Embodiments of a typical comprehensive biosensor system that include oxazine-based biosensor molecules also are provided for in the present invention. These biosensor systems further include an optical system for interrogating the oxazine-based biosensor molecules in-vivo. As used herein, the term "interrogating" refers to illumination of the oxazine-based biosensor molecules contained within an implantable polymer matrix and subsequent detection of emitted light. A schematic which generally represents a transdermal optical system, in accordance with embodiments of the invention, is shown in FIG. 19, where the light source (S) shines light through the skin and a detector (D) detects the fluorescence transmitted through the skin.

Figure 19:
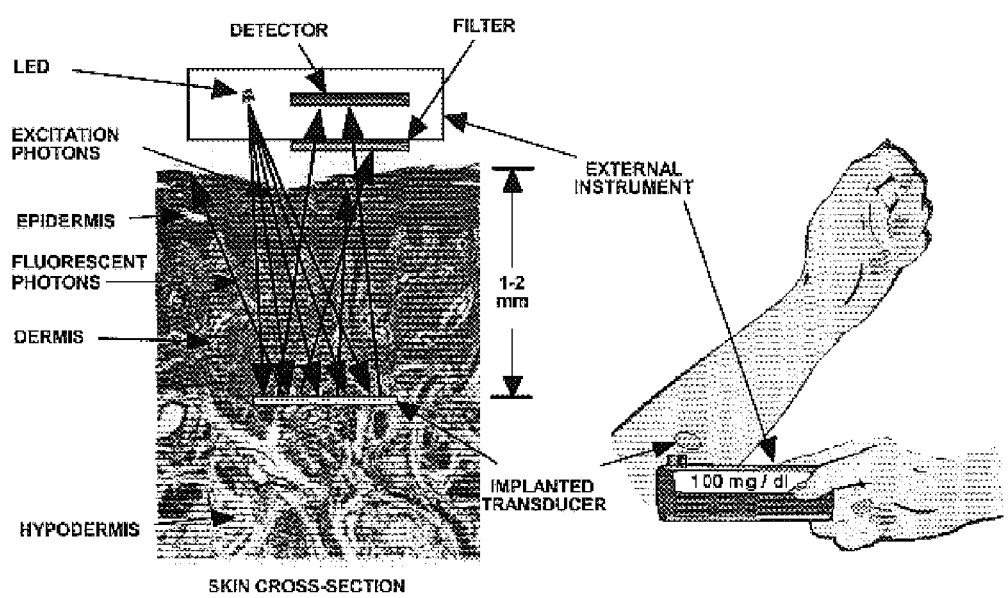
FIG. 19 provides a schematic of an illustrative sensor embodiment. In one embodiment of the sensor, it comprises a plastic matrix approximately the size of a dime and is implanted about 1–2 mm below the skin surface.
Figure 20A:
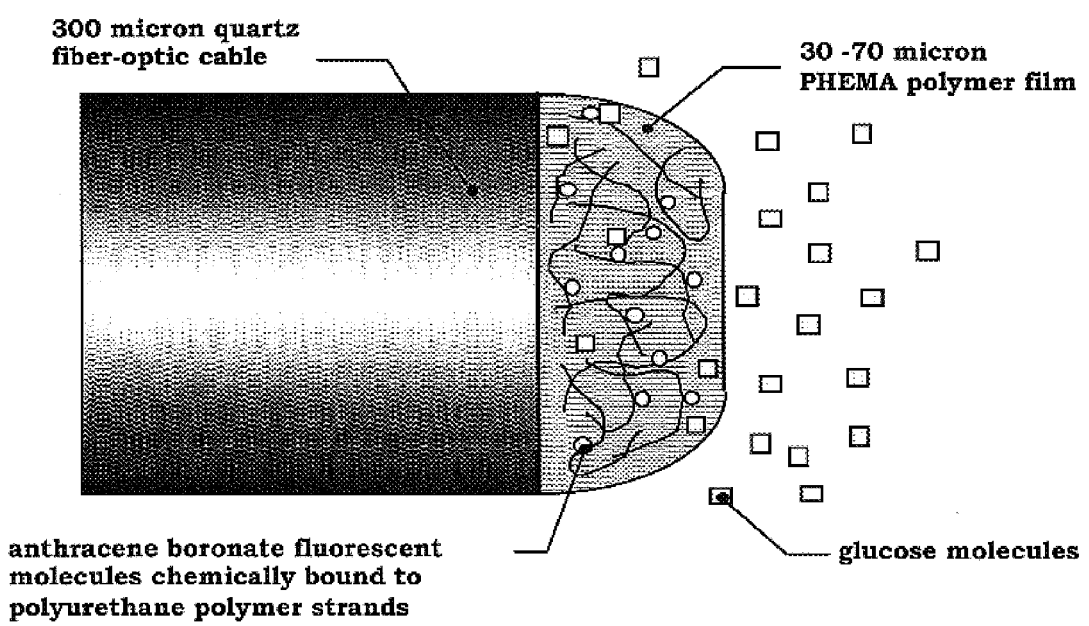
FIG. 20A provides a schematic of an illustrative sensor embodiment. In one embodiment of the sensor, it comprises a fiber optic cable.
Figure 20B:
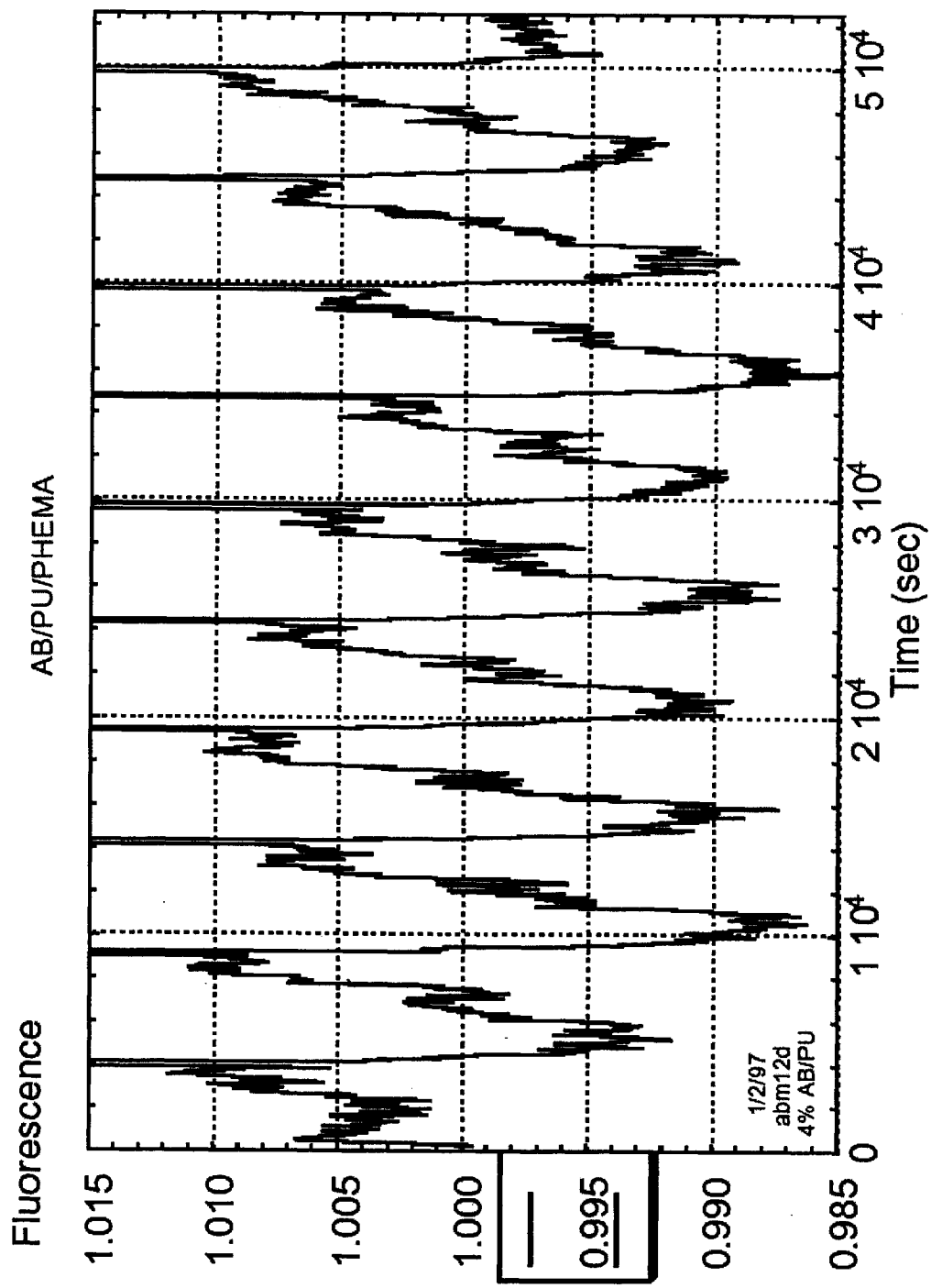
FIGS. 20B and 20C are graphs showing the fluorescence of AB bound to a pHEMA polymer film.
Figure 20C:
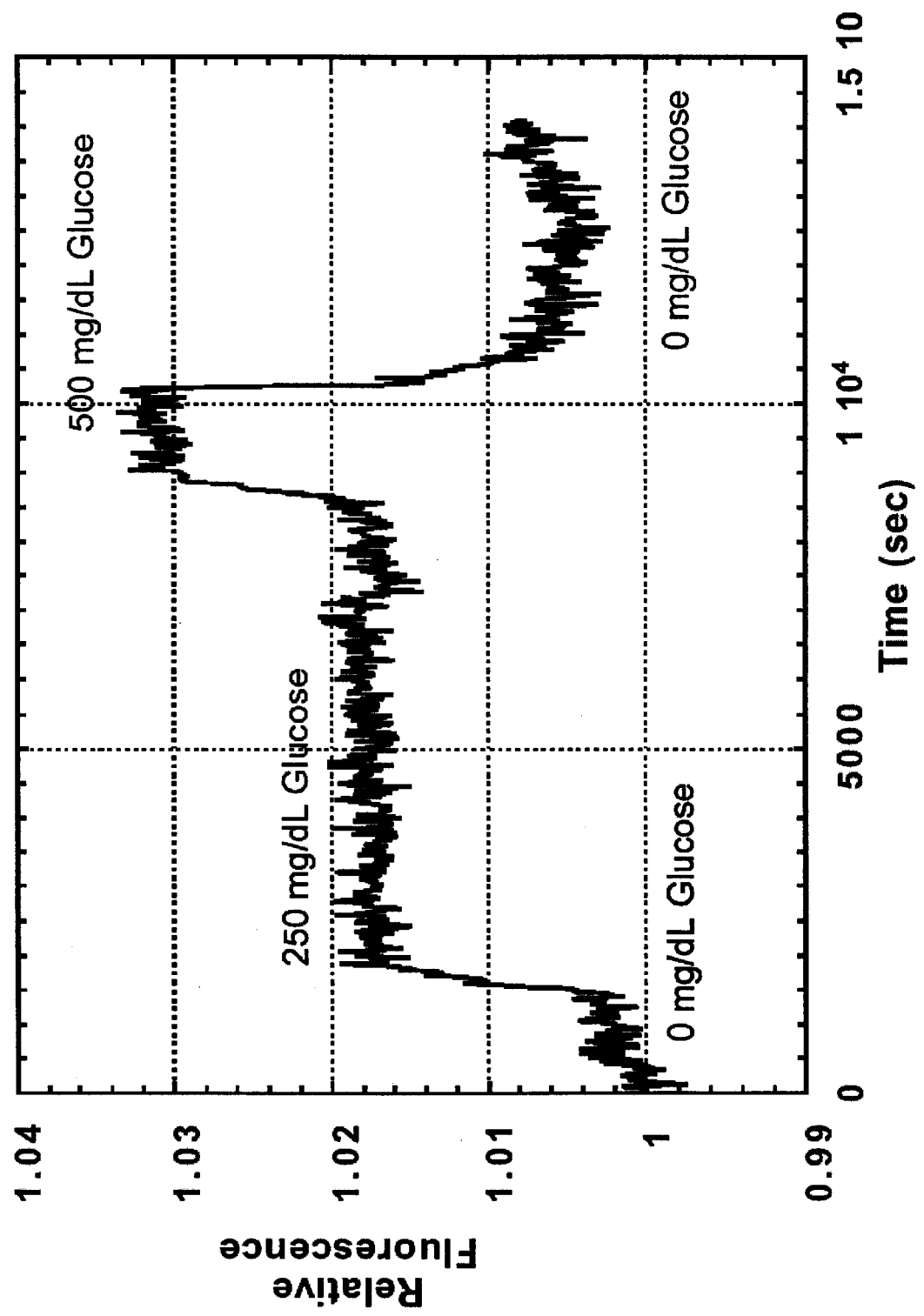
Figure 21A:
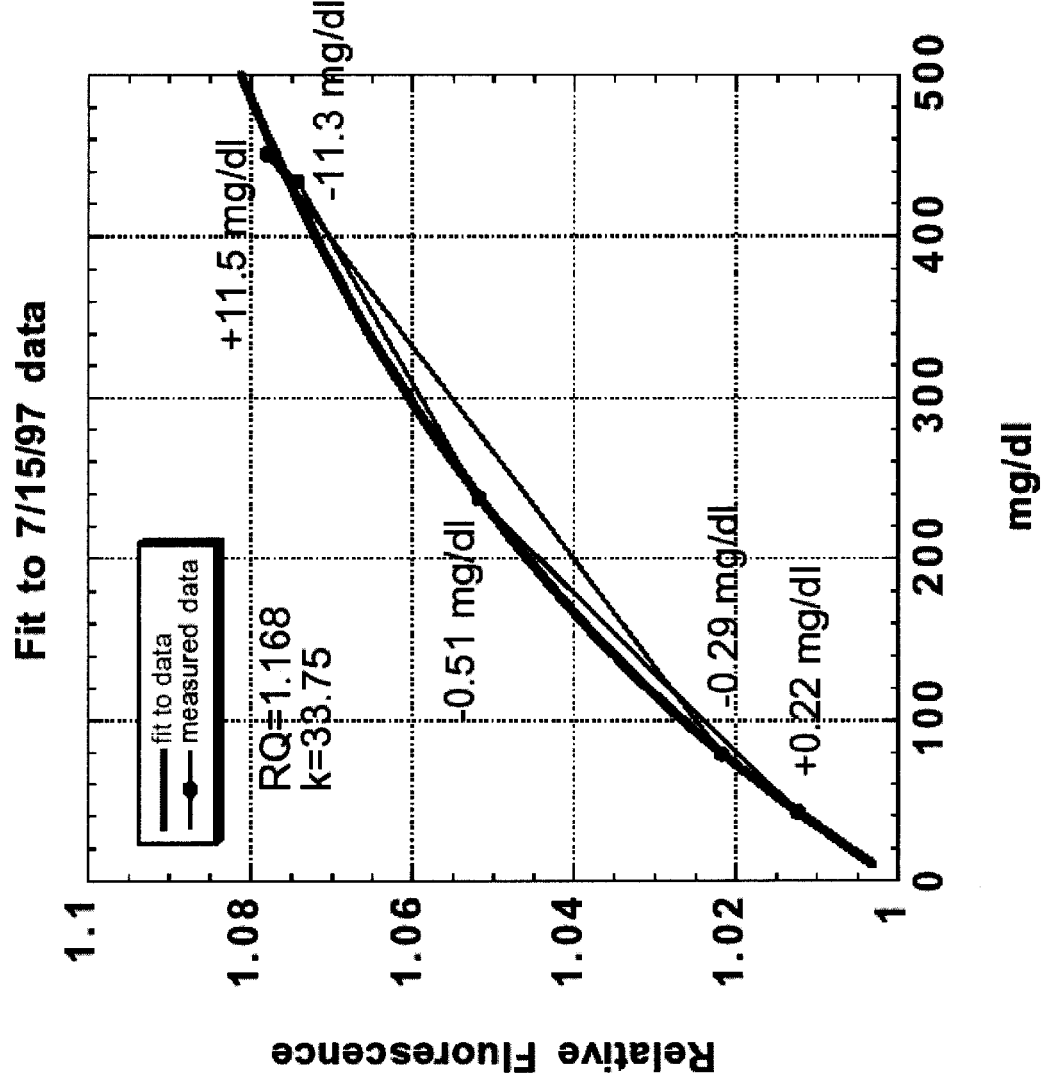
FIG. 21 is a graph showing AB's transduction of glucose while chemically bonded to a glucose permeable polymer (pHEMA) membrane.
Figure 21B:
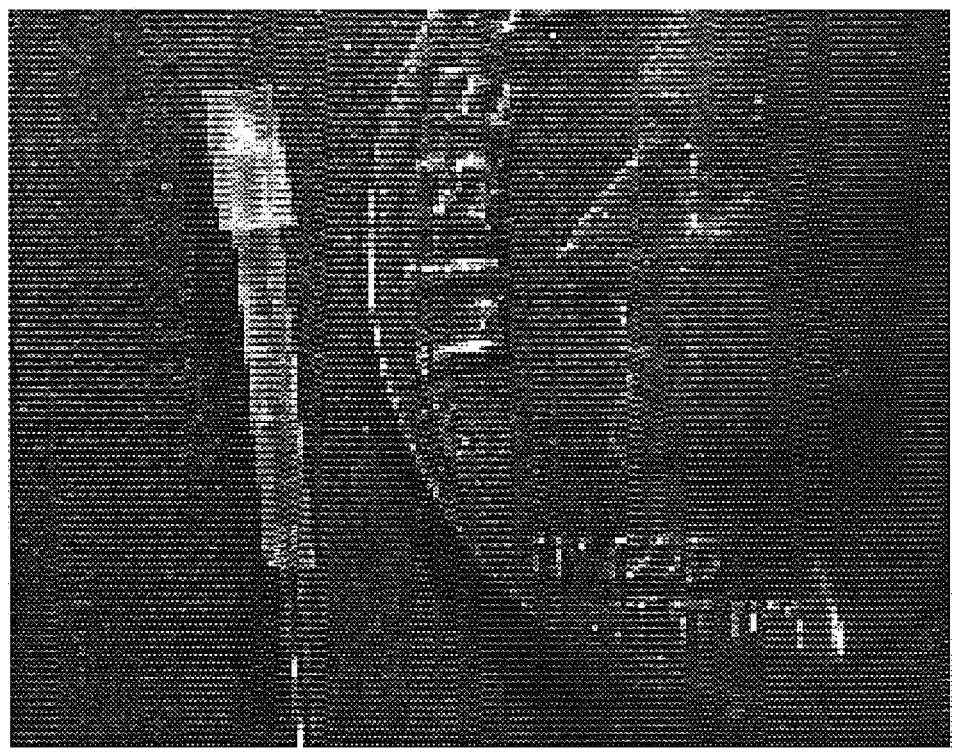
Figure 21C:
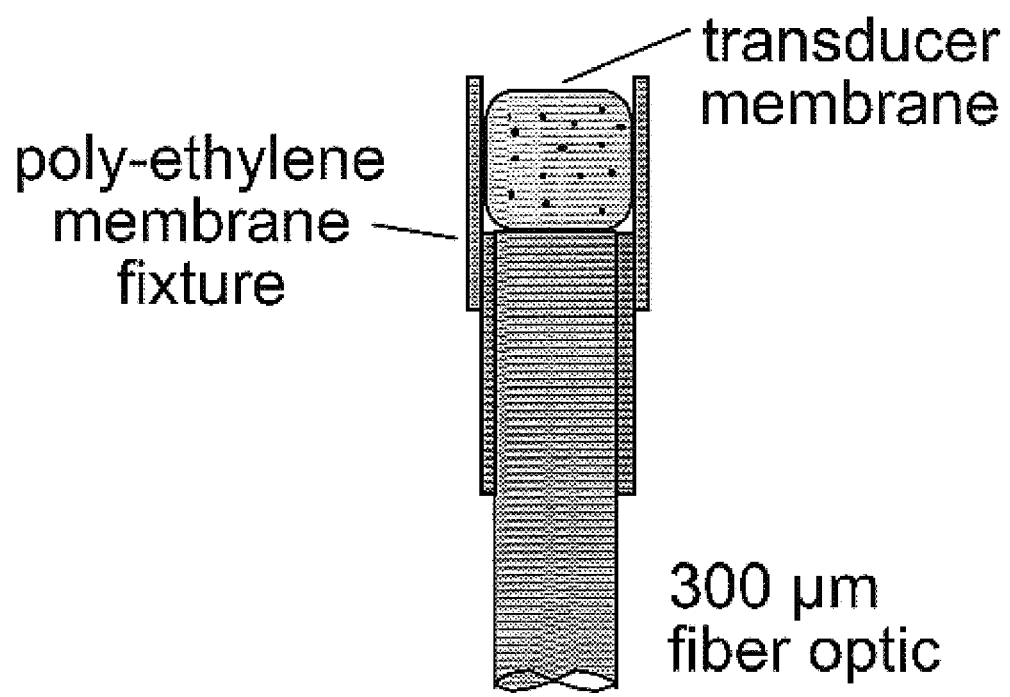
Figure 22A:
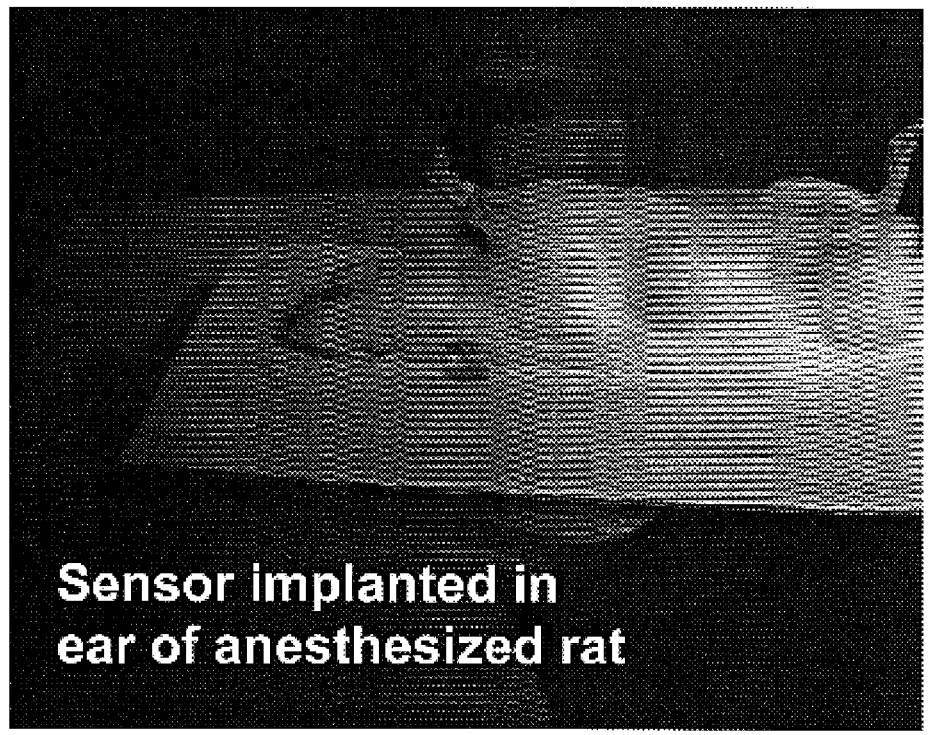
FIG. 22A shows a sensor implanted in vivo.
Figure 22B:
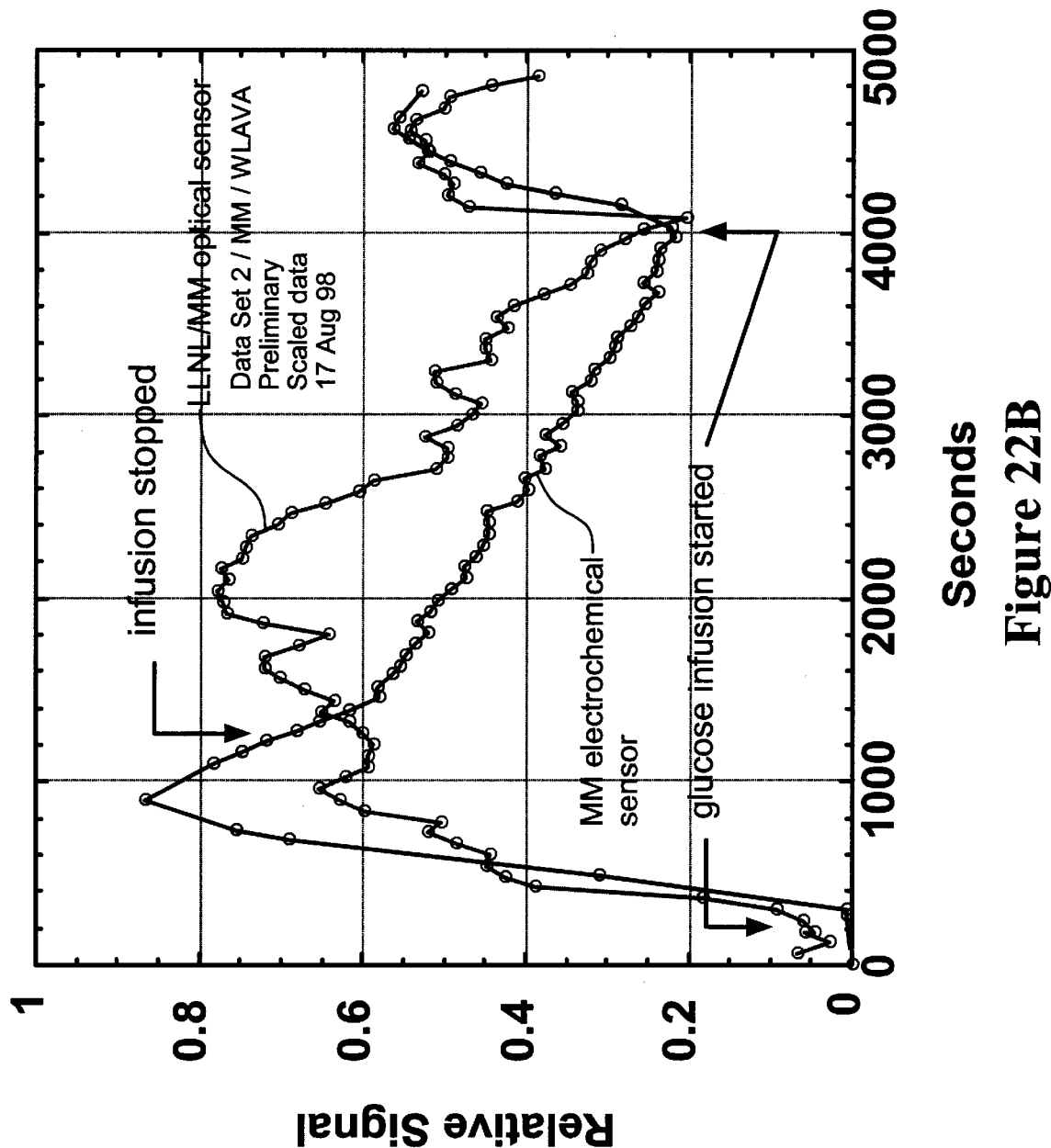
FIG. 22B shows information obtained from the sensor in response to various physiological states.
Figure 23:
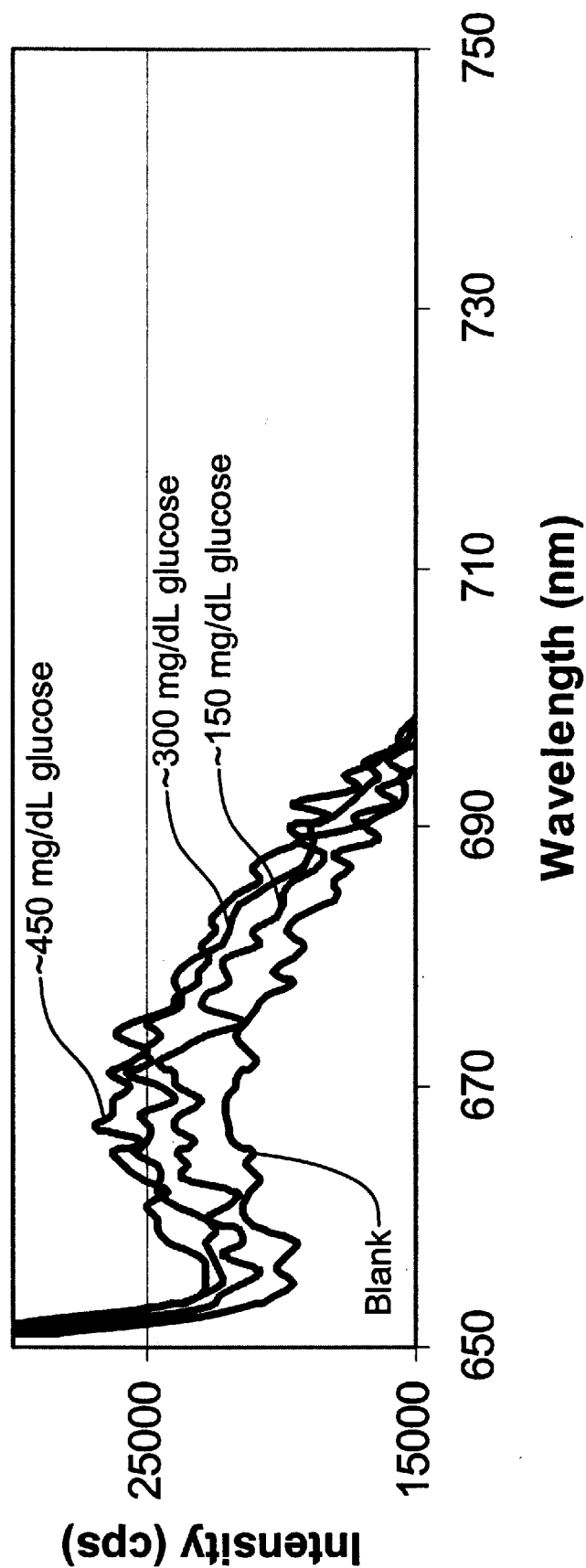
FIG. 23 provides a graph of experimental data from Example 1, specifically Nile blues' change in fluorescence intensity at 671 nm relative to glucose addition.
Figure 24:
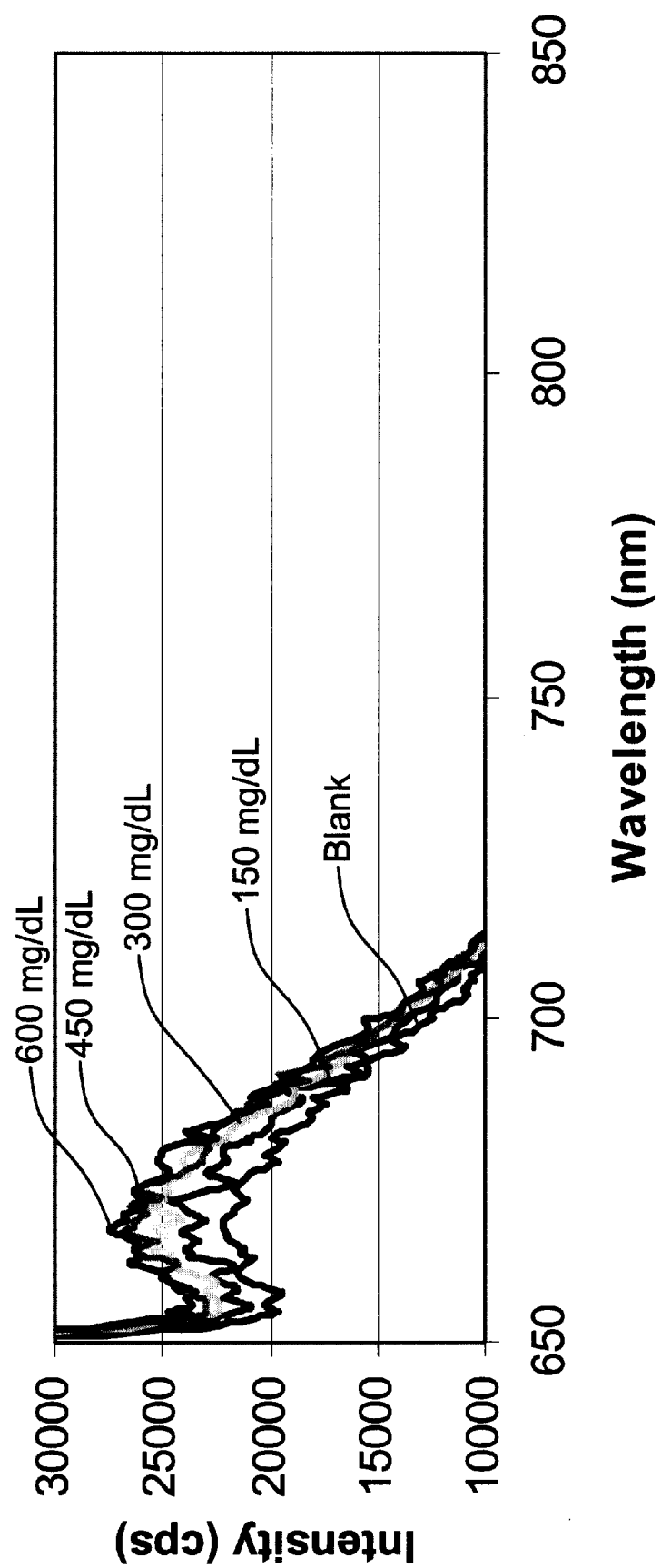
FIG. 24 provides a graph of experimental data from Example 2, specifically Nile blues' change in fluorescence intensity at 671 nm relative to glucose addition.
Figure 25:
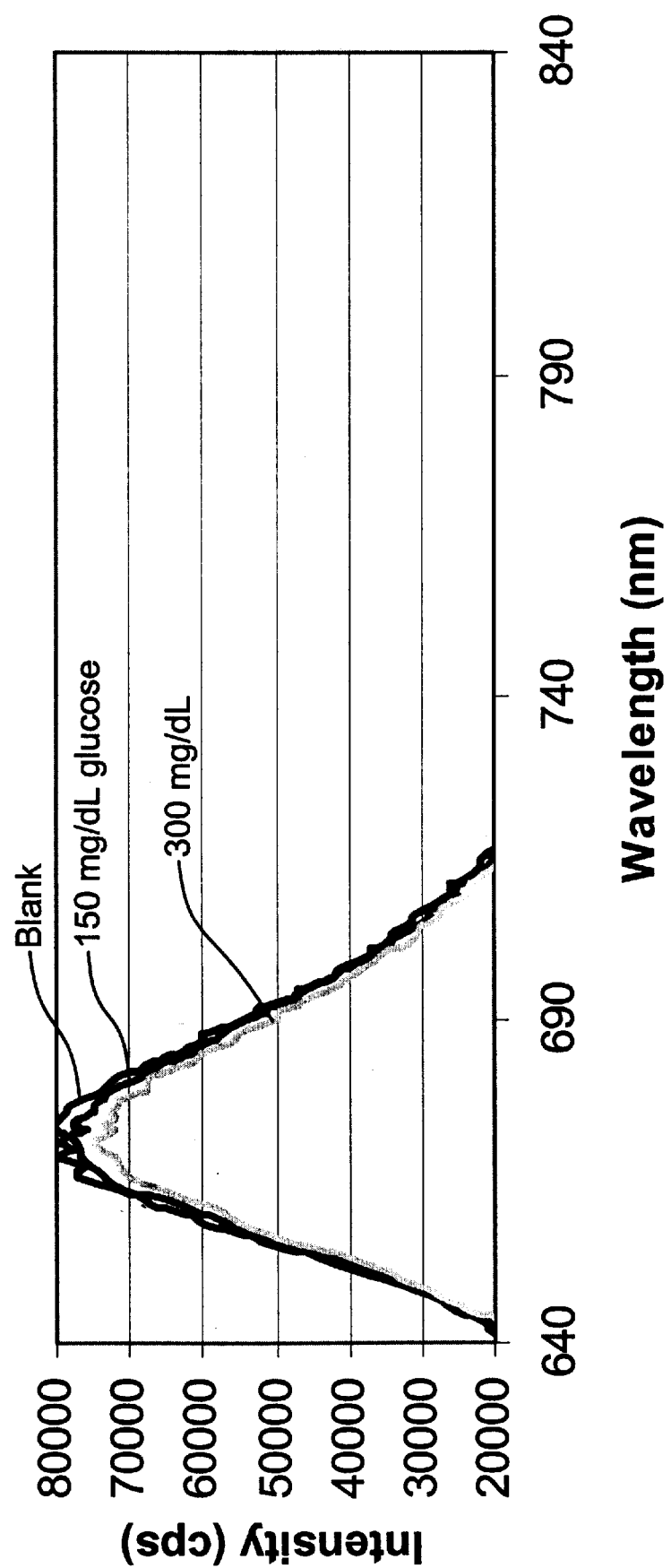
FIG. 25 provides a graph of experimental data from Example 3, specifically Nile blues' change in fluorescence intensity at 671 nm relative to glucose addition.
Figure 26:
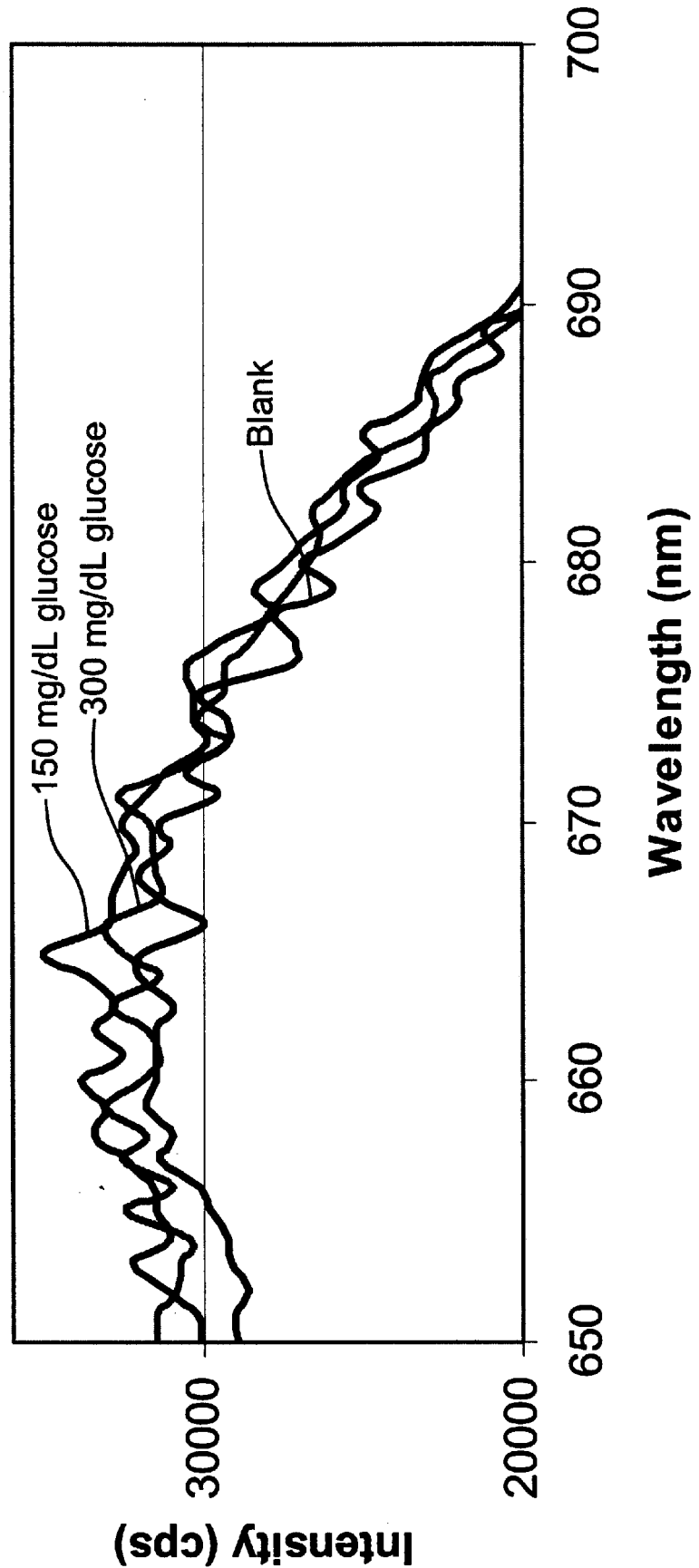
FIG. 26 provides a graph of experimental data from Example 4, specifically Nile blues' change in fluorescence intensity at 671 nm relative to glucose addition.
Figure 27:
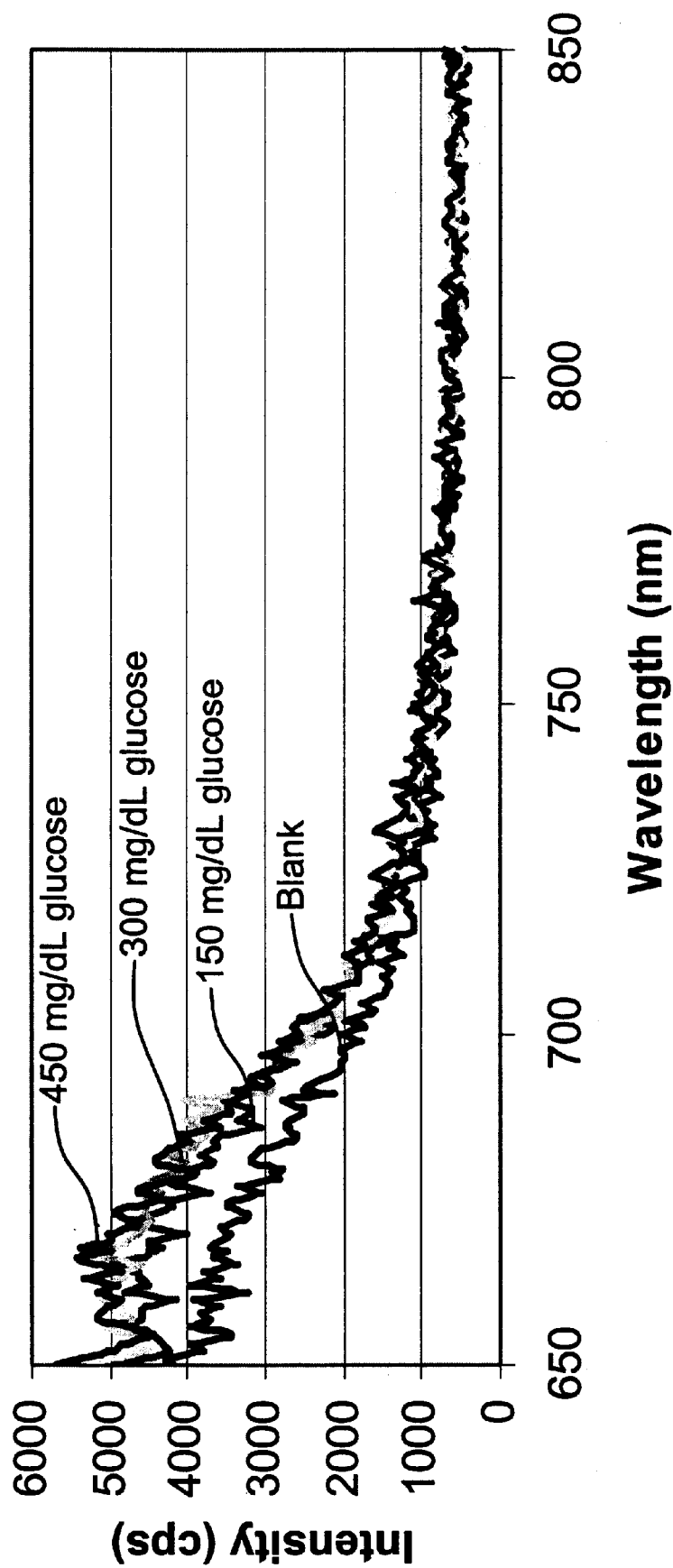
FIG. 27 provides a graph of experimental data from Example 5, specifically Nile blues' change in fluorescence intensity at 671 nm relative to glucose addition.
Figure 28:
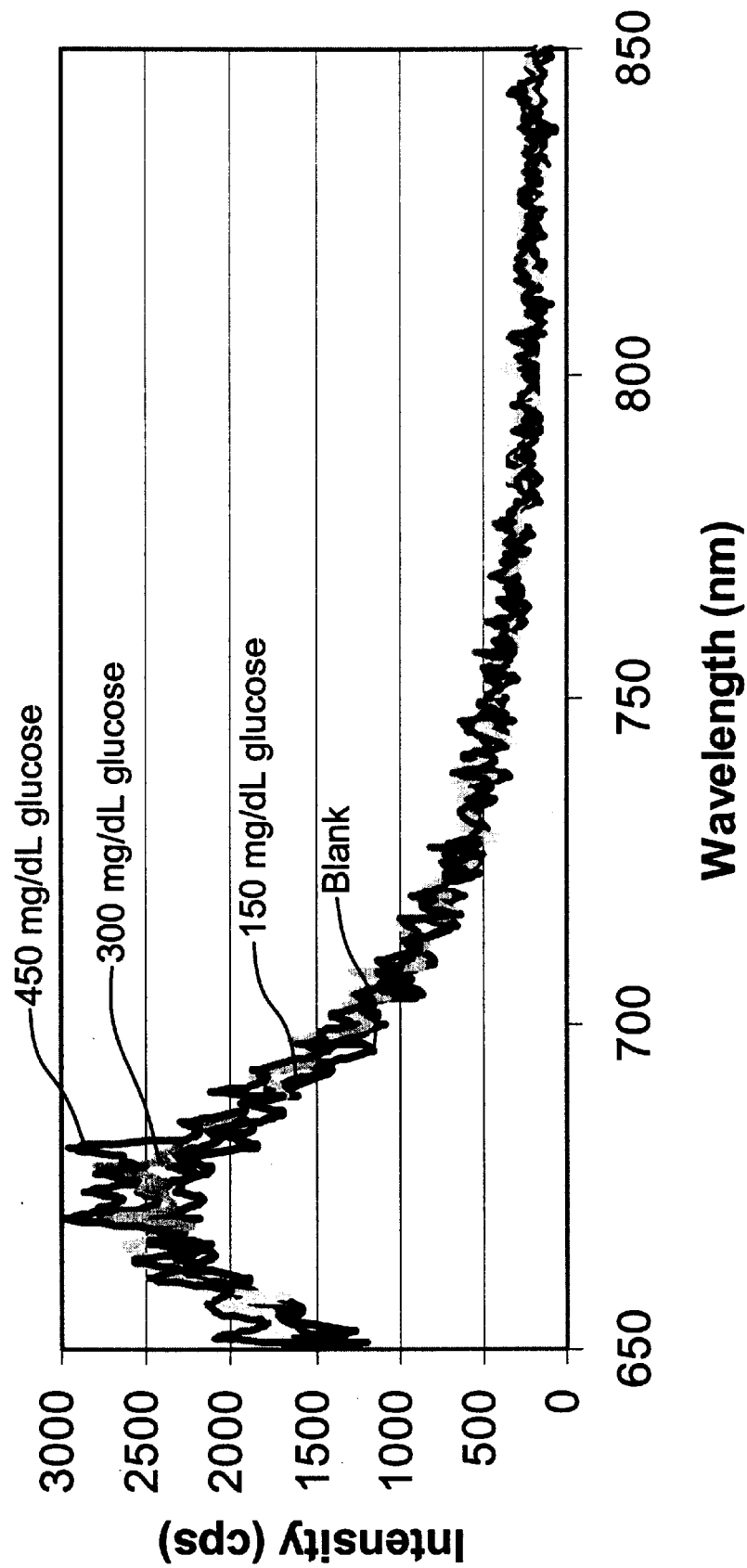
FIG. 28 provides a graph of experimental data from Example 6, specifically Nile blues' change in fluorescence intensity at 671 nm relative to glucose addition.
Figure 29:
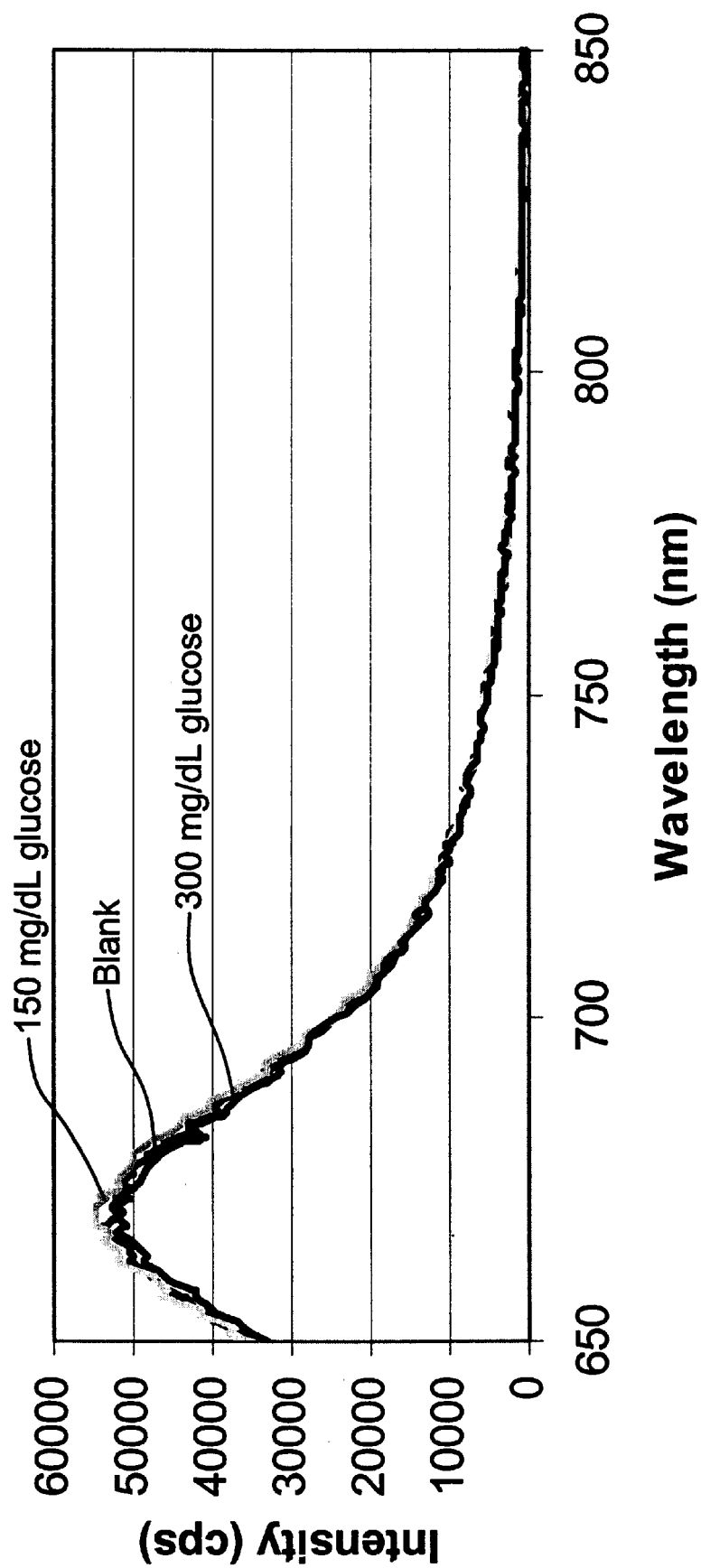
FIG. 29 provides a graph of experimental data from Example 7, specifically Nile blues' change in fluorescence intensity at 671 nm relative to glucose addition.
Figure 30:
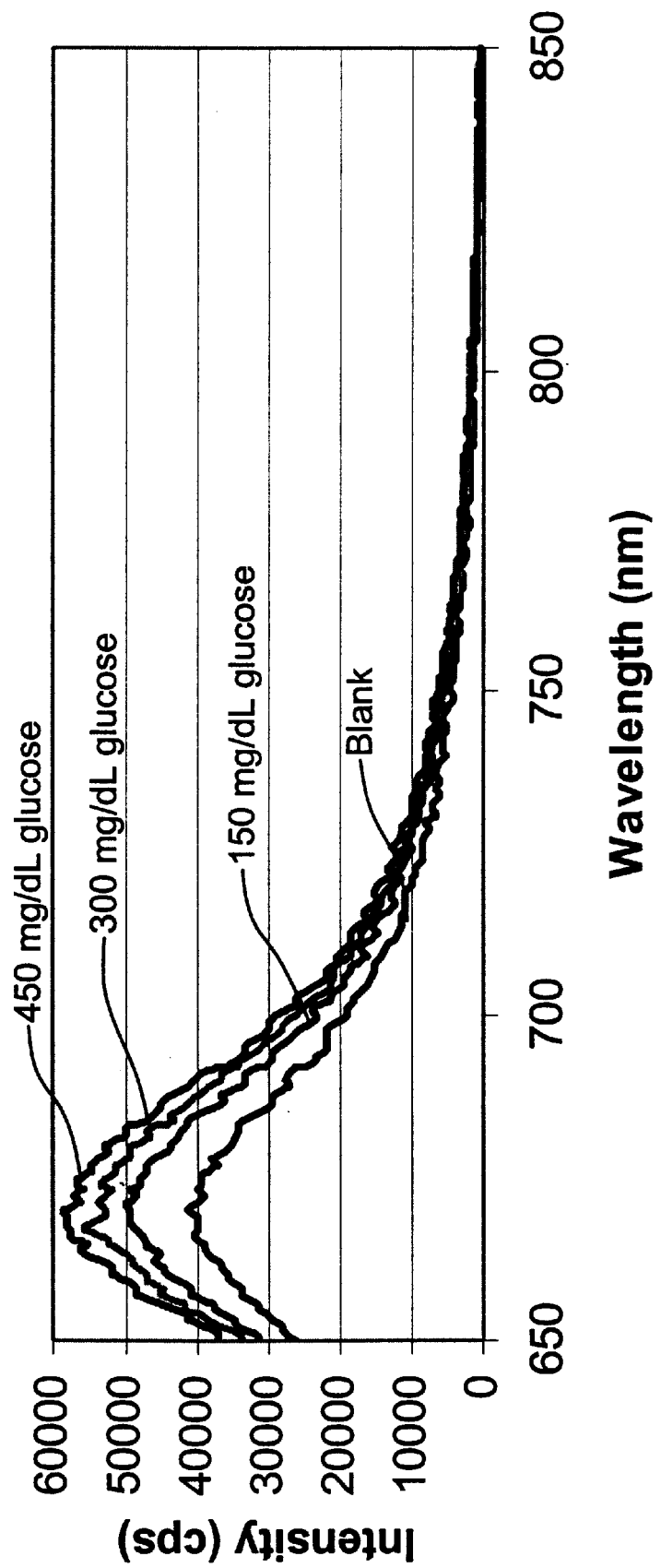
FIG. 30 provides a graph of experimental data from Example 9, specifically Nile blues' change in fluorescence intensity at 671 nm relative to glucose addition.
Figure 31A:
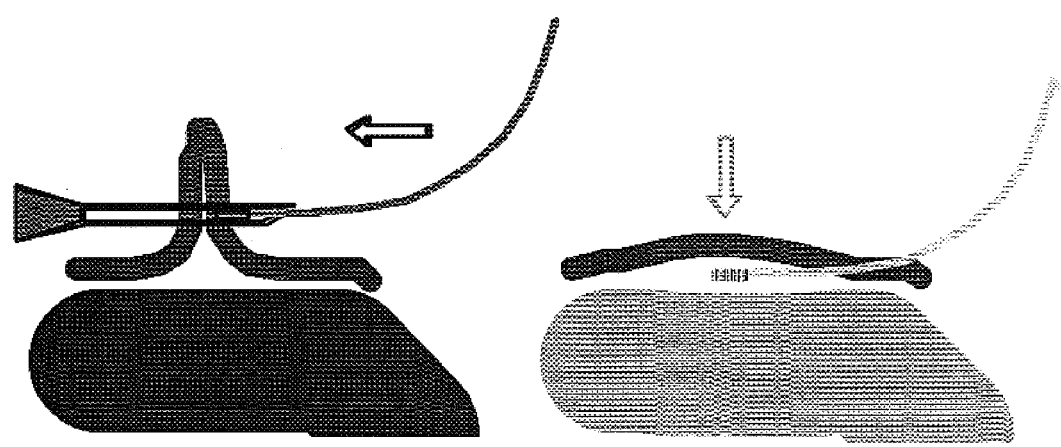
FIGS. 31A–31C respectively show sensor embodiments, a sensor implanted in vivo and information obtained from the sensor in response to various physiological states.
Figure 31B:
Figure 31C:
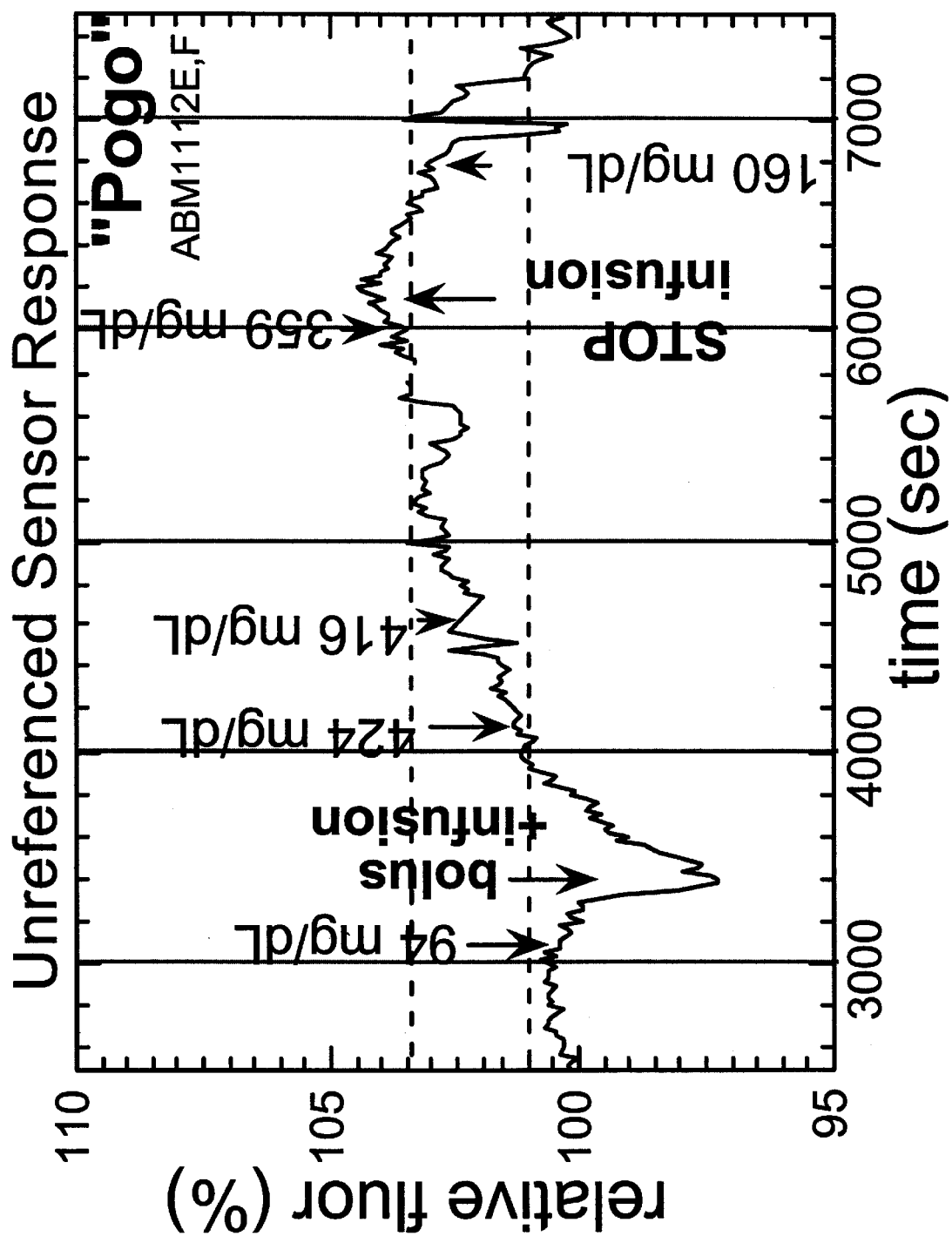
Figure 32A:
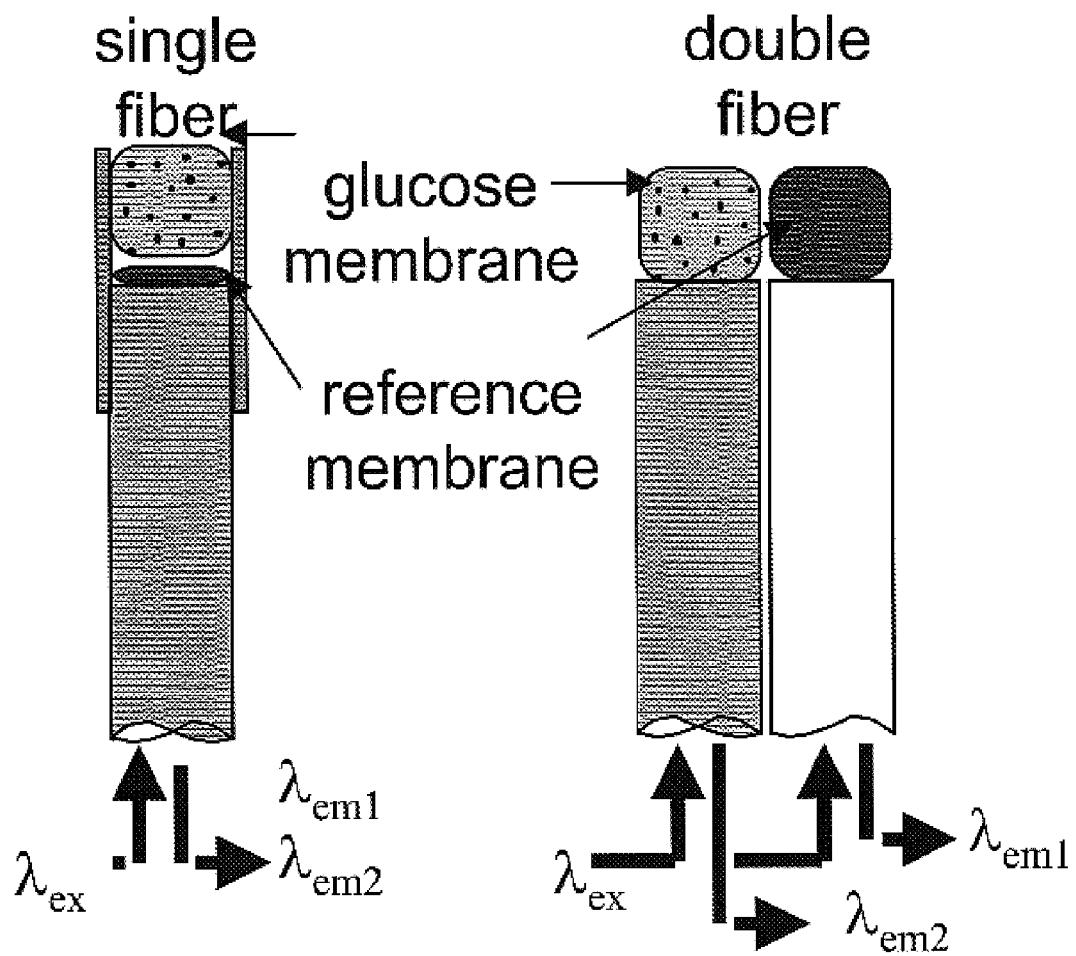
FIGS. 32A–32B respectively show sensor embodiments, information relating to fluorescence lifetime measurements of sensor data.
Figure 32B:
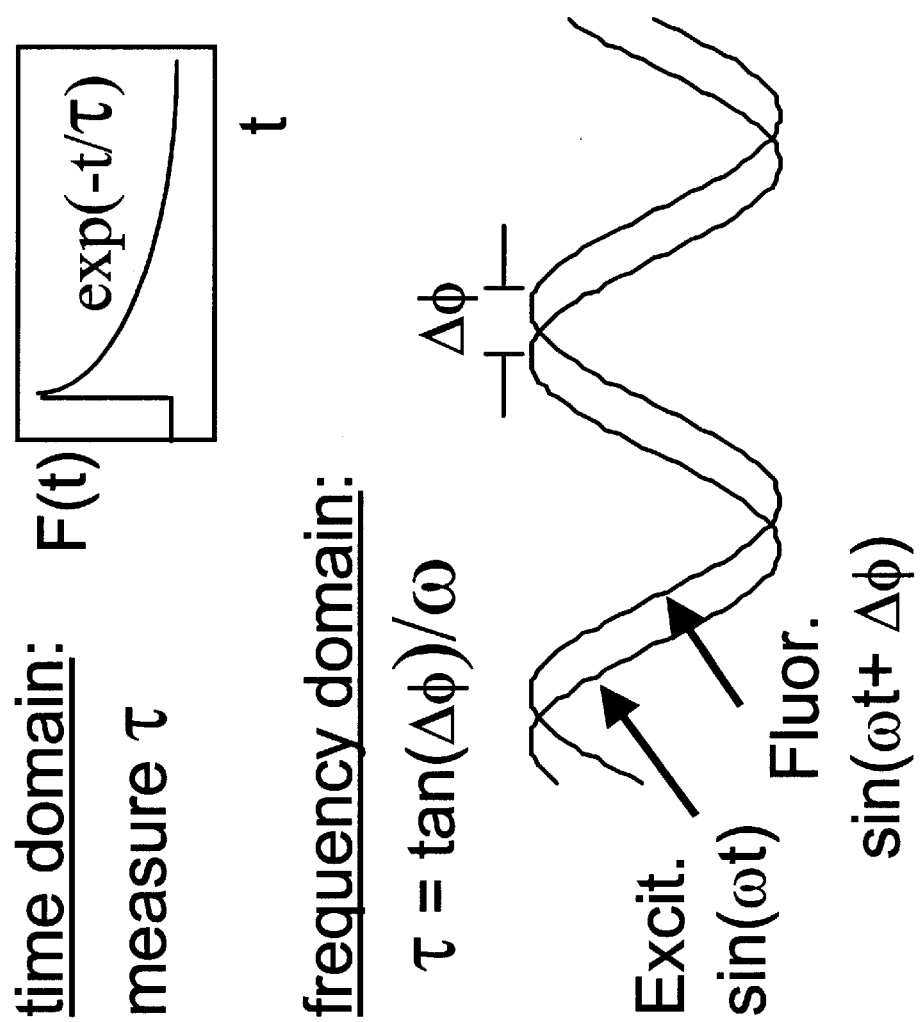
Figure 33A:
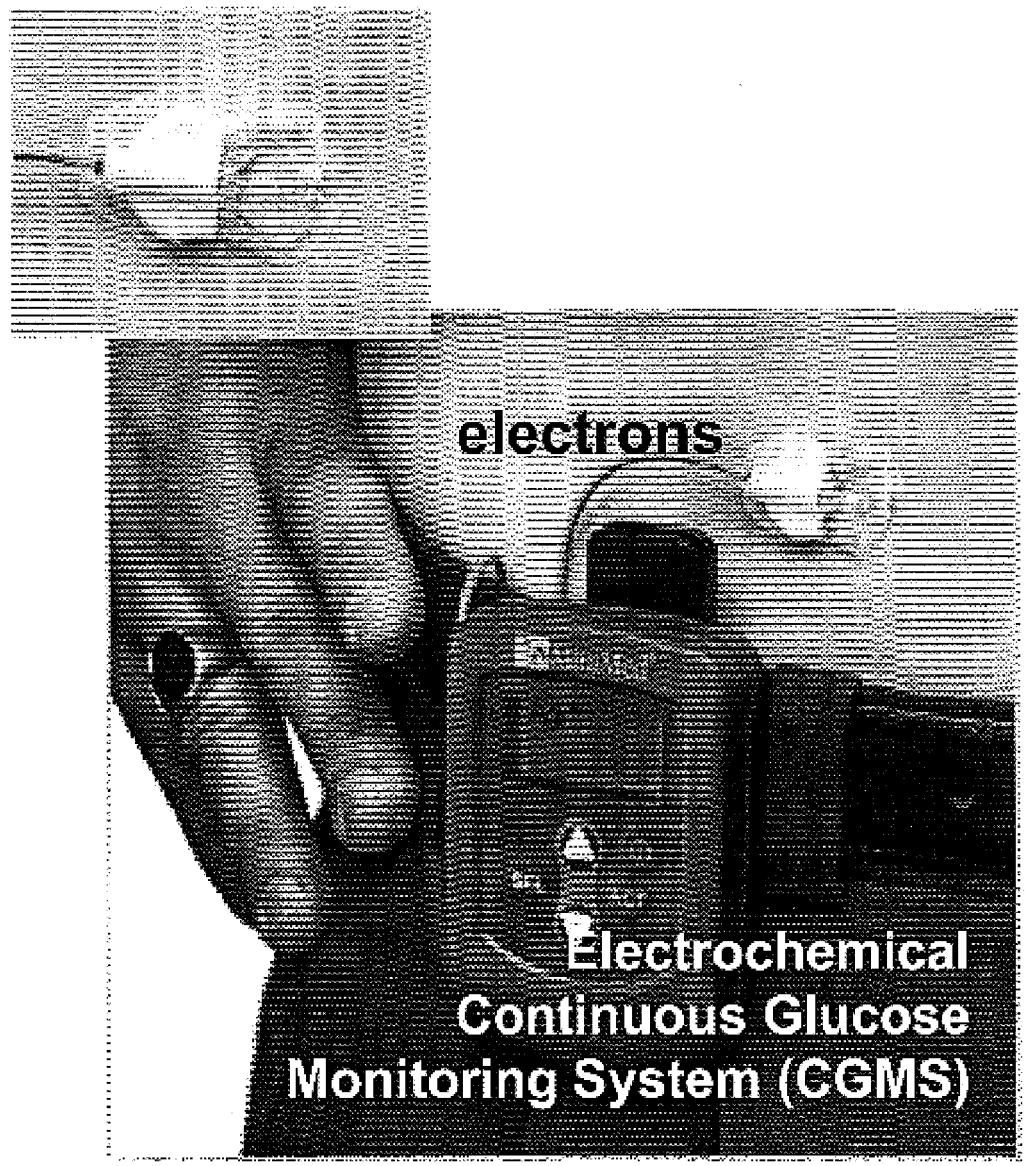
FIGS. 33A–33B show various sensor embodiments.
Figure 33B:
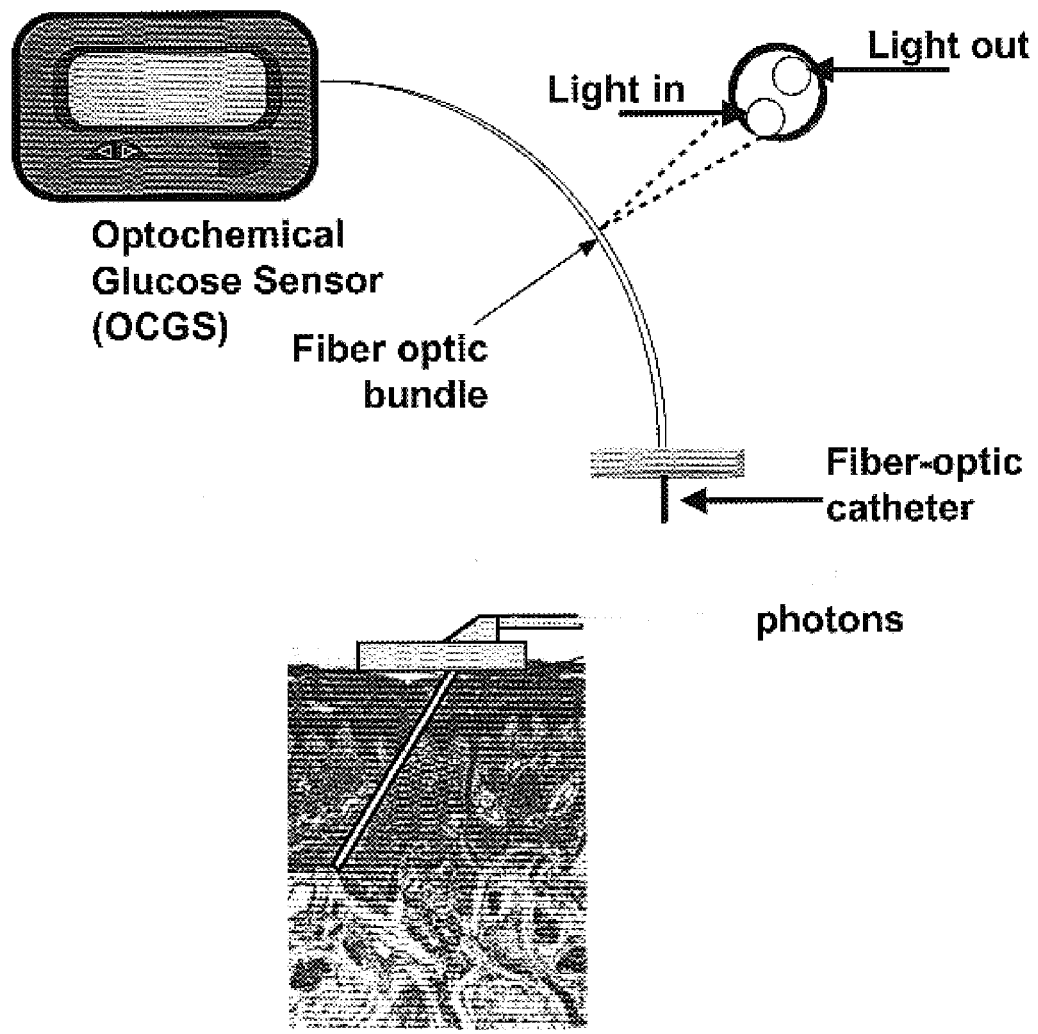

Illustrative embodiments of the present invention are provided in FIGS. 19–21. As can be seen, the basic scheme utilizes both a detector and source module which can be external to the skin. The source provides an excitation signal which interrogates a subcutaneous amplification system. The system then produces an amplified signal which is monitored by the external detector. In typical embodiments the amplification system contains an inmobilized chemical amplification component which may contain a fluorescent moiety providing a signal which is modulated by the local analyte concentration. A filter can also be incorporated into the system for the fluorescent photons (for those embodiments in which a fluorescent dye is used). The implanted amplification system is interrogated transdermally by a small instrument worn or placed over the implant. The small instrument contains a light source (e.g., a filtered LED) and a filtered detector (e.g., a photomultiplier tube, an unbiased silicon photodiode). The signal from the detector provides a continuous reading of the patient's analyte level which can also be used as input to, for example, an insulin pump or a visual reading for the patient. Alternative embodiments known in the general art such as the use of a fiber optic for interrogation of the amplification system can also be employed in such systems.

Figure 17:
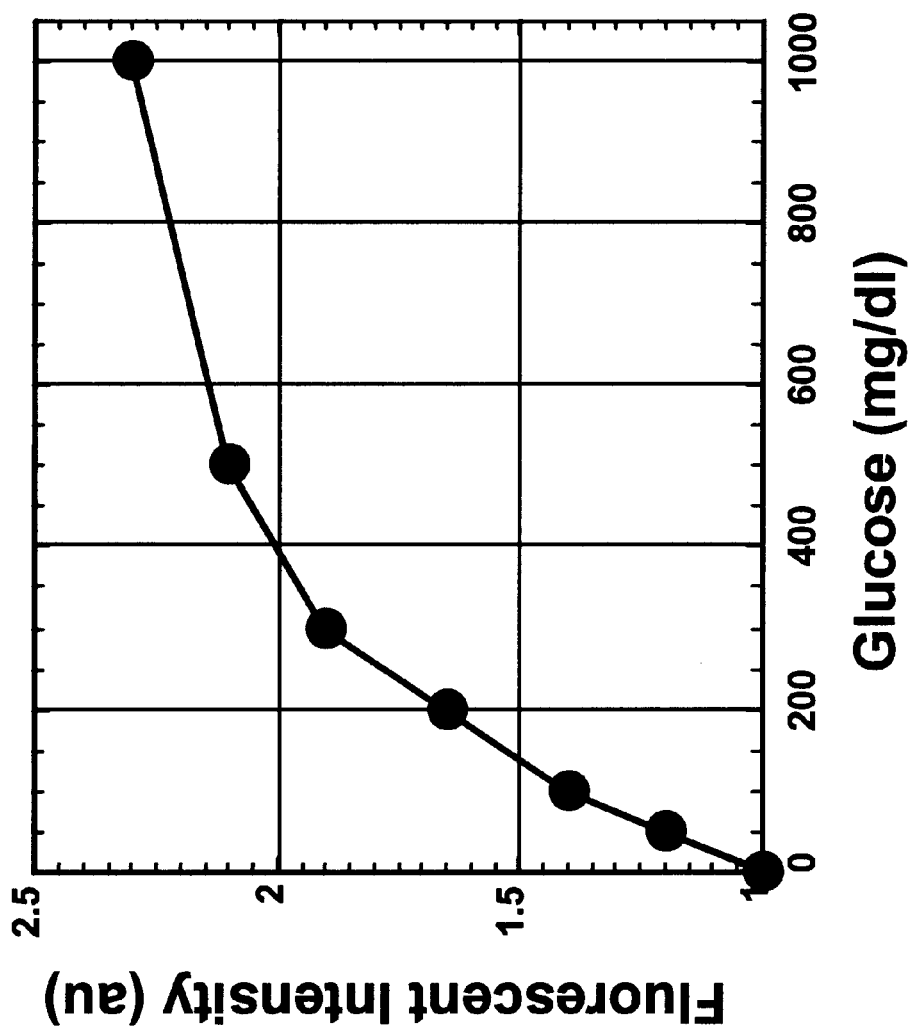
FIG. 17 is a graph showing the fluorescence of AB attached to PEG2 polymer in PBS after 8 days which demonstrates the high transduction of AB polymer in solution.

In an exemplary facet of the sensor systems described herein, FIG. 17 illustrates the glucose transduction of a fluorescent molecule attached to a typical hydrophilic linker, in this case AB coupled to a polyethylene glycol polymer. Methods for generating such molecules are known in the art, for example the following brief description of a typical synthesis of a water soluble PEG-AB system. Approximately 100 equivalents of a diisocyanate polyethylene glycol (PEG; molecular weight ~3400) is combined with hydroxypentyl anthracene boronate (one equivalent) in a solution of tetrahyrofuran containing a dibutyl-tin catalyst. The concentrations of reactants are adjusted so that statistically each PEG unit will be end capped with only one AB linked molecule. The solution is heated to reflux temperature and stirred overnight under a nitrogen atmosphere. The reaction is quenched (reacting the remainder of the isocyanate groups) by the addition of methanol at room temperature, stirred for four hours, and then evaporated to near dryness under a nitrogen gas stream. The polymer is taken to dryness under vacuum. Triturating with heptane removes the tin catalyst The solid obtained form the reaction is taken up in distilled water to form a stock solution, and added to aqueous PBS for glucose transduction experiments. Transduction of AB polymer system is found to be in the range of 18–65% increase in fluorescence at 200 mg/dl.

As illustrated above, the oxazine-based molecules in accordance with embodiments of the invention solve the problem of obtaining optimal optical transmission of fluorescence via implanted fluorescent reporter systems of in-vivo polyhydroxylate analyte concentrations. For example, embodiments of these oxazine-based biosensor molecules and systems exhibit wavelengths of fluorescence emission greater than about 650 nm, and accordingly, can be used to detect polyhydroxylate analytes, particularly glucose, in media with high opacities to visible light, such as human skin and tissue. These biosensor molecules and systems of the invention thus have the desired properties of long wavelengths of fluorescence emission, as well as exhibiting reasonably high quantum yields and high molar efficiencies. In addition, these biosensor molecules and systems generally exhibit excitation wavelengths greater than about 600 nm, and thus have the benefit of generally being excited at wavelengths that are above the ultraviolet range. Particular embodiments of the biosensor molecules of the invention have at least one maximum wavelength in their emission spectra that is greater than about 600 nm and have at least one wavelength in their emission spectra that is greater than about 650 nm. An exemplary oxazine-based biosensor molecule in accordance with embodiments of the invention utilizes Nile Blue as a fluorophore. This Nile Blue biosensor molecule generally has an excitation wavelength of about 625 nm and an emission wavelength of about 675 nm in an aqueous Phosphate Buffered Saline (PBS) solution. Particular embodiments of the invention, however, may emit in the near infrared (IR) region of the spectrum.

To use embodiments of the oxazine-based biosensor molecules of the present invention for polyhydroxylate analyte sensing in-vivo, these biosensor molecules are generally immobilized in a polymer matrix to form implantable biosensors that can be placed under the skin. It is preferable, therefore, that the implanted biosensor molecule be incorporated/immobilized into a polymer matrix to prevent the oxazine-based biosensor molecules from diffusing into bodily fluids and being carried into the body. In preferred embodiments, the matrix is permeable to the analyte of interest and be stable within the body. Still further, the matrix should be prepared from biocompatible materials, or alternatively, coated with a biocompatible polymer. As used herein, the term "biocompatible" refers to a property of materials or matrix which produce no detectable adverse conditions upon implantation into an animal. While some inflammation may occur upon initial introduction of the implantable amplification system into a subject, the inflammation will not persist and the implant will not be rendered inoperable by encapsulation (e.g., scar tissue).

A biocompatible matrix can include either a liquid substrate (e.g., a coated dialysis tube) or a solid substrate (e.g., polyurethane/polyureas, silicon-containing polymers, hydrogels, solgels and the like). Additionally, the matrix can include a biocompatible shell prepared from, for example, dialysis fibers, teflon cloth, resorbable polymers or islet encapsulation materials. A matrix can be in the form of a disk, cylinder, patch, microspheres or a refillable sack and, as noted, can further incorporate a biocompatible mesh that allows for fill tissue ingrowth with vascularization. While subdermal implantation is preferred, one skilled in the art would realize other implementation methods could be used. A key property of the matrix is its permeability to analytes and other reactants necessary for chemical amplification of a signal. For example, a glucose monitoring matrix must be permeable to glucose.

Immobilization of the biosensor molecules can involve entrapment by, encasement in, attachment to or the like, one or more polymer matrix materials. Further, attachment to a polymer matrix can involve covalent attachment or ionic attachment, such as a salt bridge. For in-vivo glucose sensing, embodiments of the oxazine-based biosensor molecules can be immobilized in a glucose permeable matrix to form an implantable oxazine-based biosensor than can be implanted cutaneously, subcutaneously, dermally, subdermally, or the like. For these implanted embodiments, the oxazine-based biosensor may be in the form of a small patch, a bead, a disc, or the like, which is implanted beneath the skin. These implants may be implanted subcutaneously or may be part of a transcutaneous implant, such as the embodiment illustrated in FIG. 20, where the implanted oxazine-based biosensor is placed at one end of a wire with an optical fiber. In either case, embodiments of the biosensor of the invention generally can be implanted about a few millimeters beneath the skin. Complete subcutaneous implants are generally placed about 1–2 mm beneath the skin. Fiber optic or transcutaneous implants, on the other hand are generally placed about 1–4 mm beneath the skin. Other embodiments may be implanted with the detection hardware and a transmitter (not shown). These embodiments may be implanted anywhere in the body where there is sufficient space and sufficient bodily fluids to obtain a measure of analyte concentration levels.

The polymer matrix used for immobilization can either be prepared from biocompatible materials or coated with biocompatible materials. Moreover, the polymer matrix may include a mixture of polymers or copolymers that maintain certain desired conditions of the internal biosensor milieu, such as pH and solubility of implantable biosensors and biosensor molecules. Preferably, at least the outer surfaces of the implantable biosensor should include, or be coated with, at least one biocompatible material, as these surfaces are to be in contact with human tissue and body fluids. As used herein, the term "biocompatible" refers to a property of a material or matrix that produce no substantial adverse effects upon implantation in the body. The biocompatible polymer matrix also must be permeable to the analyte of interest. For example, in the case of sensing glucose in-vivo, the biocompatible polymer matrix should be permeable to glucose and be stable within the body for the lifetime of the implant.

Figure 14:
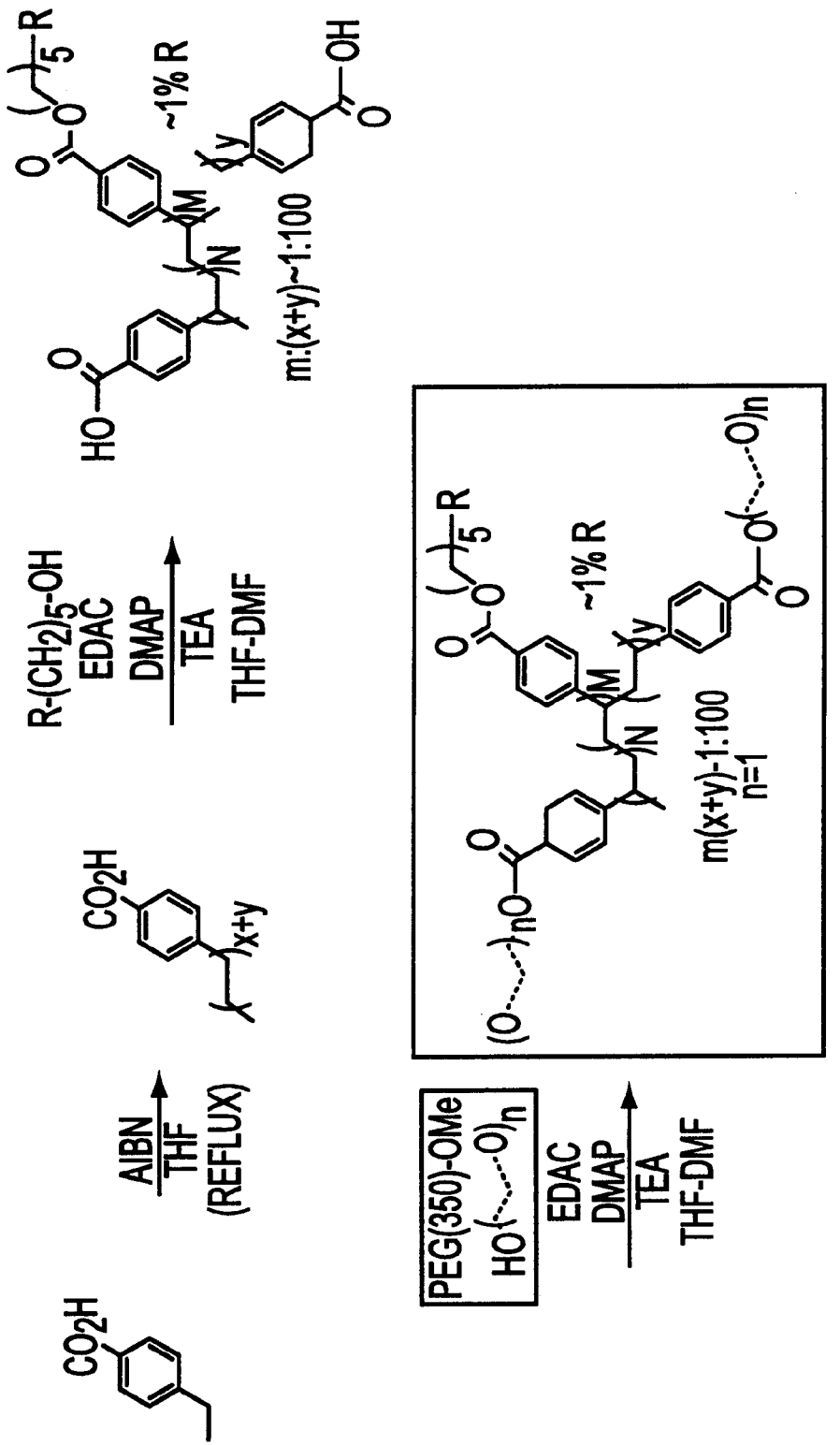
FIG. 14 depicts a reaction scheme for incorporating an oxazine-based biosensor molecule into a polycarboxystyrene polymer matrix, where R represents any oxazine-based biosensor molecule.

The polymer matrix can include either a liquid substrate (e.g., a dialysis tube that contains oxazine-based biosensor molecules in accordance with embodiments of the invention attached to a water-soluble polymer matrix) or a solid substrate such as oxazine-based biosensor molecules in accordance with embodiments of the invention attached to a water-insoluble polymer-matrix, such as polyurethanes, polystyrenes, polyacrylates, polyureas, silicon-containing polymers, pHEMA, hydrogels, solgels, copolymers thereof, mixtures thereof or the like. FIG. 14 depicts a reaction scheme for incorporating an oxazine-based biosensor molecule into a polycarboxystyrene polymer matrix, where R represents any oxazine-based biosensor molecule. Additionally the polymer matrix can include a biocompatible shell prepared from, for example, dialysis fibers, telfon cloth, resorbable polymers or islet encapsulation materials. Further, the polymer matrix that encompasses the oxazine-based biosensor molecules can be in any compact form, such as a small disc, cylinder, patch, microsphere, refillable sack, or the like, and can further incorporate a biocompatible mesh that allows for full tissue regrowth and vascularization.

Figure 15:
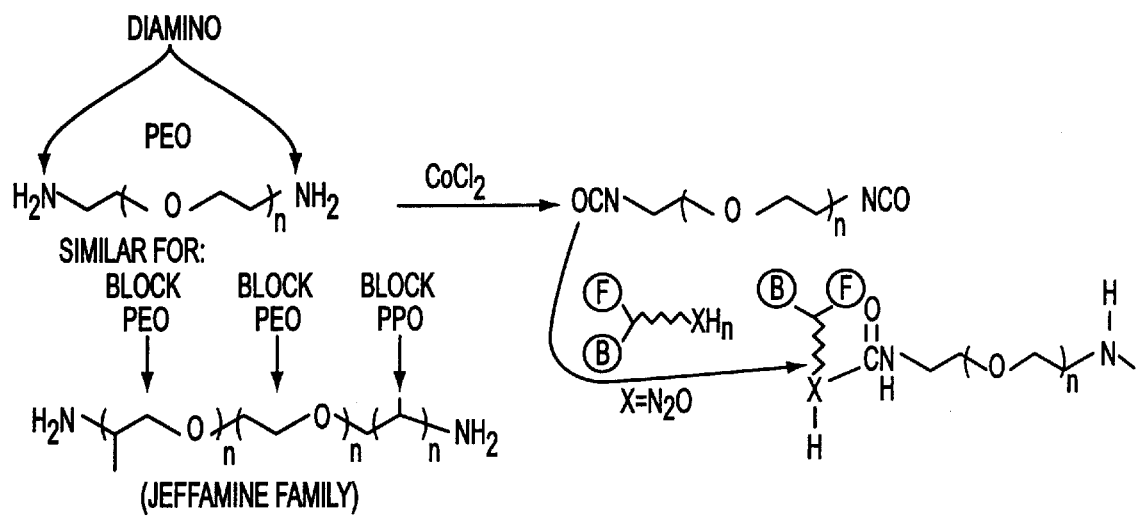
FIG. 15 depicts illustrative embodiments of oxazine-based biosensor molecules attached to water-soluble polymer matrices.
Figure 15:
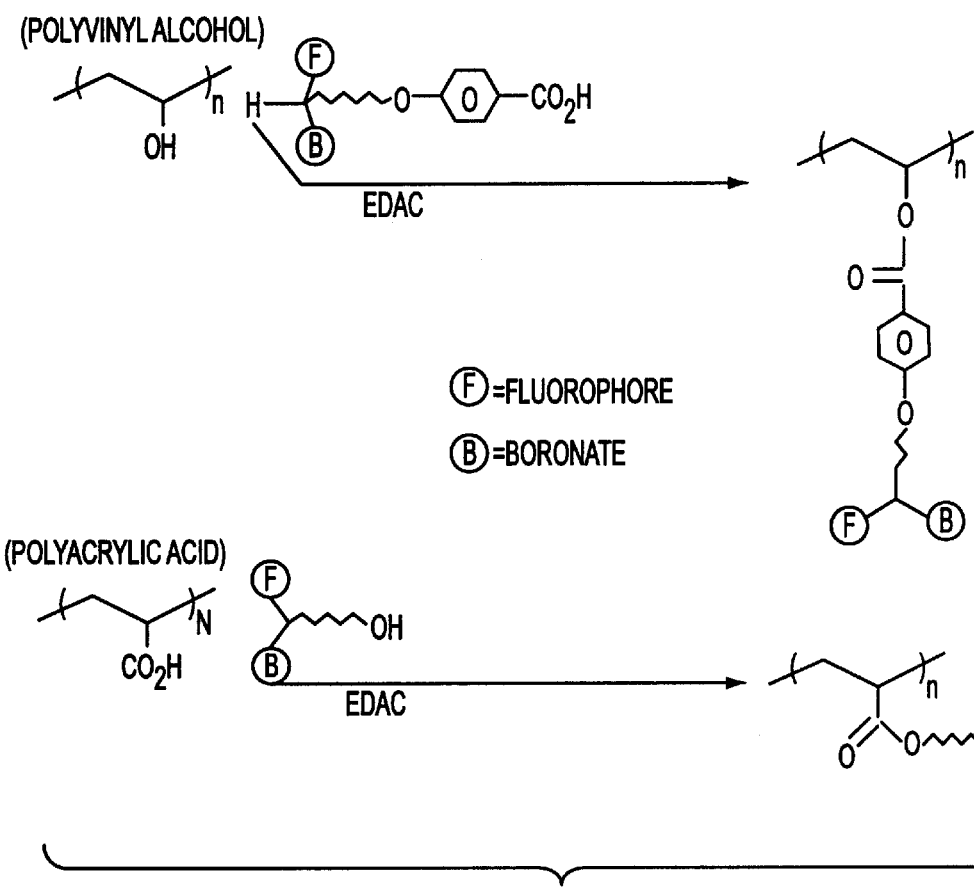

Particular embodiments of the implantable oxazine-based biosensor may include water-soluble polymers that are functionalized with the fluorescent biosensor molecules, such polymers include polyethylene glycol (amino-terminated), Jeffamine polymers (2-propyl amino terminated block-polypropylene oxide block-polyethylene oxide block-polypropylene oxide), poly(vinyl alcohol), poly(acrylic acid), linear pHEMA copolymers thereof or the like. Because these polymers are water-soluble, they can be placed inside a microporous container, shell or the like that is permeable to glucose, is suitable for implantation, i.e., the container, shell or the like should be biocompatible. Examples of such microporous polymeric materials are linear polyesters of carbonic acid, poly(vinylchloride), polyamides, polychloroethers, polyurethanes, polyimides, copolymers thereof, mixtures thereof or the like. Examples of some of these polymers functionalized with oxazine-based biosensor molecules are shown in FIG. 15. These water-soluble polymers possess some distinct advantages over other types of fluorescent biosensor molecule-functionalized polymers. These advantages include favorable solution behavior for improved polyhydroxylate analyte recognition and binding, i.e., improved kinetics, as well as reasonably straightforward chemistry for attachment of oxazine-based biosensor molecules.

Other implant embodiments of the oxazine-based biosensors of the invention can be formulated similar to a reusable implant embodiments described in WO 01/01851, published on Jan. 11, 2001, which includes a reusable analyte sensor site for use with the oxazine based biosensor in accordance with embodiments of the invention. WO 01/01851 is incorporated by reference. If a sealable port is included in embodiments of the implantable biosensors of the invention, the port may be useful for refilling the implant with fresh biosensor molecules, or biosensor molecules attached to a polymer matrix, without removing the implant.

Figure 16:
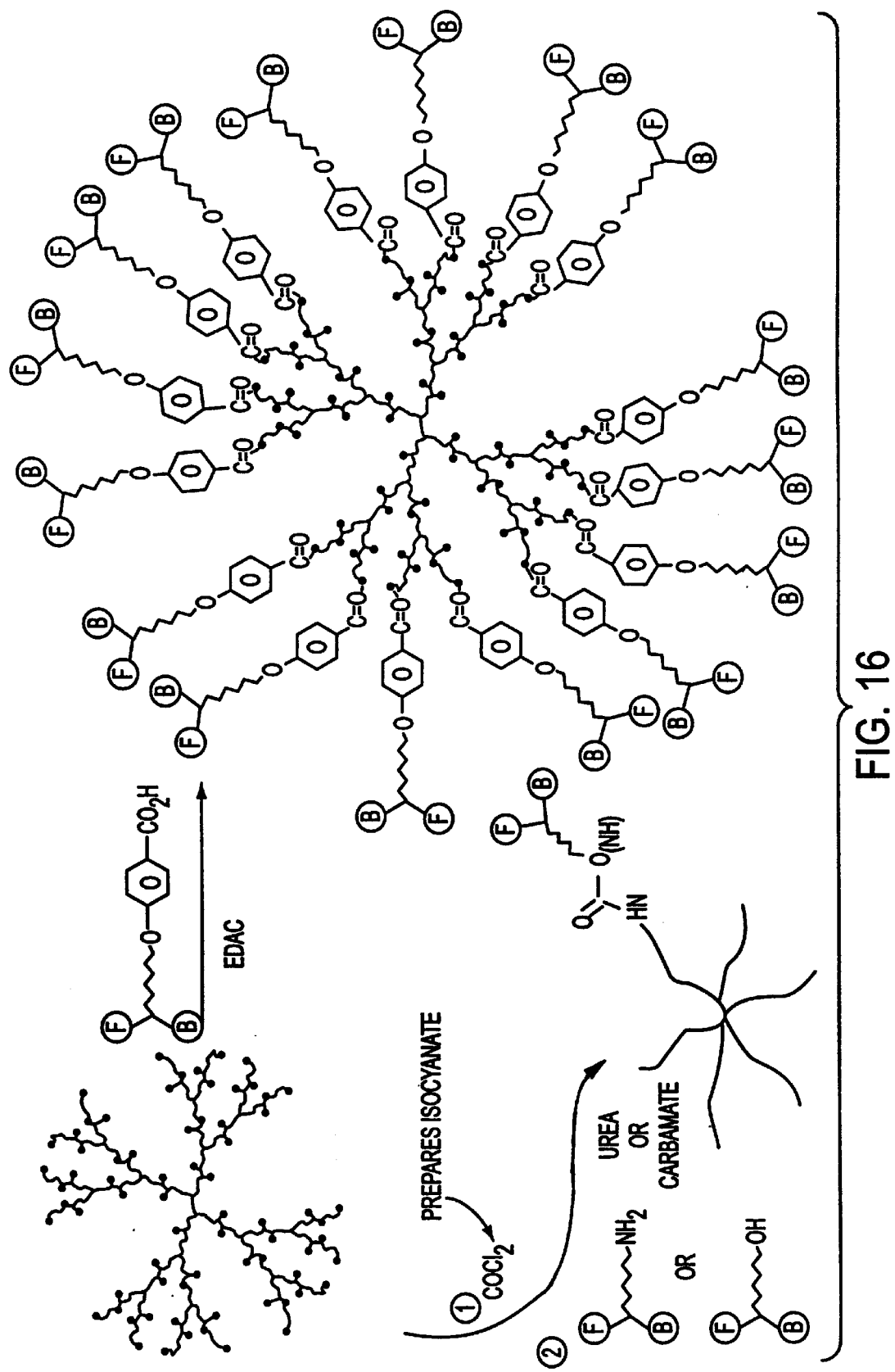
FIG. 16 depicts illustrative embodiments of oxazine-based biosensor molecules attached to multiple attachment-point polymers. For such embodiments, monotypic of polytypic receptors can be used.

Also included in particular embodiments of the invention are oxazine-based biosensor molecules attached to polymers with multiple attachment points, such as a relatively new class of polymers called star dendrimers. Several examples of multiple-attachment point, star dendrimers polymers functionalized with an oxazine-based biosensor molecule in accordance with embodiments of the invention are shown in FIG. 16. Polymers with multiple attachment points for functionalization with fluorescent biosensor molecules in accordance with embodiments of the invention possess some favorable properties. First, these polymers do not require encapsulation for them to be effective in analyte sensing. Further, some of these polymers possess appropriate characteristics for use as a biomaterial, i.e., mechanical strength, hydrophilicity, purity, and the like. Examples of the materials suitable for use with multiple-attachment point polymers are cross-linked poly(vinyl alcohol), cross-linked poly(acrylic acid), star dendrimers, copolymers thereof, mixtures thereof or the like.

The implantable oxazine-based biosensors in accordance with embodiments of the invention are suitable for long term use beneath the skin. Long term use can be about one month or less to about a year. For long-term implants, embodiments of the implantable, oxazine-based biosensor may further include one or more adhesion coatings, which preferably are biologically active materials that facilitate attachment of cells to the biocompatible matrix, such as extracellular matrix molecules (ECMs) including laminins, tenascins, collagens, netrins, semaphorings, thrombosphodins, fibronectins, vitronectins, proteoglycans, biologically active fragments thereof, mixtures thereof, or the like. These adhesion coatings are advantageous in facilitating diffusion limited reactions by shortening the diffusion distance from the host to the interior of the implants. Additionally, these adhesion coatings may include cell-cell adhesion molecules (CAMS), such as the cadherin superfamily, fibronectins, selectins, integrins, biologically active fragments thereof, mixtures thereof or the like, or immunoglobulin (Ig) superfamily molecules, such as intercellular cell adhesion molecule (ICAM), or the like. Long-term embodiments of the implantable, oxazine-based biosensor may also include an angiogenic coating, which aids in the development of new capillary blood vessels in a tissue resulting in improvement in oxygen and nutrient supply at the implantation site. Examples of angiogenic factors include vascular endothelial growth factor (VEGF), acidic fibroblast growth factor (AFGF), basic fibroblast growth factor (BFGF), transforming growth factor-beta, platelet-derived endothelial cell growth factor, angiogenin, tumor necrosis factor-alpha, bone morphogenic protein (BMP), biologically active fragments thereof, mixtures thereof, or the like.

Because of the long wavelength operating range of the oxazine-based biosensors in accordance with embodiments of the invention, these biosensors can be interrogated by applying excitation light through the skin and externally monitoring the intensity, or lifetime, of the emitted fluorescence, for example. The measurement of the emitted light thus allows the in-vivo concentration of a polyhydroxylate analyte, such as glucose, to be quantified. Other embodiments include oxazine-based biosensors optical systems where there is no direct transmission through the skin, as the light source is also implanted or light travels to subcutaneous space via a fiber optic to the oxazine-based biosensor molecules encompassed within the implanted biosensor. This later fiber optic embodiment is depicted in FIG. 21. Still other embodiments of the biosensor systems include configurations where both the light source and detector are implanted.

FIG. 19 shows a generalized schematic of a subdermally implanted optical biosensor system in accordance with embodiments of the present invention. The light source could be a lamp, an LED, a laser diode (pulsed or modulated), or the like. The detector could be a photodiode, a CCD detector, photomultiplier tube, or the like. Optionally, filters are used to filter the incident and/or emitted beams of light to obtain the desired wavelength. The source and detector are shown in FIG. 19 as positioned outside the body, although the source and/or detector can be implanted within the body. The oxazine-based biosensor molecules in accordance with embodiments of the invention are contained within, or attached to, a polymer matrix to form a biosensor, and the biosensor is implanted beneath the skin. Preferably, the outer surfaces that are in contact with human tissue and body fluids are biocompatible. The light source is then used to illuminate the implanted biosensor and the detector detects the a signal which is usually emitted fluorescent light, or emitted fluorescent light that can be related to the fluorescence lifetimes of the oxazine-based biosensor molecules. Other forms of a signal also can be detected, such as absorbance, reflectance or transmittance, when a change in the amount of light or spectral character of light that is detected and measured is modulated by the local analyte concentration. In the case of fluorescence, a ratio of intensity of excitation and emission can be used to further verify the glucose signal. In preferred embodiments of the invention, the ratio of fluorescence from the oxazine-based biosensor molecules to the fluorescence of a calibration fluorophore can be measured to improve the accuracy of the measurement of analyte concentration. This method can eliminate errors of light transmission through the skin, for example.

The invention provided herein addresses a number of issues in this art. For example, to improve transmission of the signal through the skin, the fluorescent compound should operate at longer wavelengths than about 450 nanometers. The transmission through a few millimeters of skin increases logarithmically with wavelength—from 0.1% at about 400 nm to almost 100% at 850 nm. Thus, the longer the wavelength, the greater the transmission through skin. An excitation and emission wavelength greater than about 600–650 nm is an enormous improvement over about 400–450 nm. Because of the significant increase in optical skin transmission at longer wavelengths, a practical glucose sensor can operate more efficiently, more accurately, and with a greater signal-to-noise ratio.

In addition, it is advantageous to match the peak excitation wavelength with an existing light source (such as an LED or diode laser). Furthermore, by operating at longer wavelengths, there is a reduction in the tissue autofluorescence background. Further progress in creating such compounds, however, entails the formidable task of synthetically assembling various combinations of fluorophores and glucose-recognizers into integrated molecules that have the desired fluorescent properties, such as operating at longer wavelengths (450–700 nm), while simultaneously retaining the requisite glucose transduction properties.

This invention addresses the optical transmission problem and provides exemplary fluorescent compounds that have been demonstrated to exhibit the needed photochemical behavior and operate in a wavelength range that makes a subcutaneous fluorescent glucose sensor practical.

The invention described herein has a number of embodiments. A preferred embodiment includes an implantable biosensor, the biosensor including the oxazine compounds described herein (e.g. Nile Blue) contained in a polymer matrix. Typically the polymer matrix is biocompatible, water-soluble and permeable to the glucose. In representative embodiments, the polymer matrix is polyethylene glycol (amino-terminated), polyethylene glycol (hydroxy terminated), Jeffamine polymers (2-propyl amino terminated block-polypropylene oxide block-polyethylene oxide block-polypropylene oxide), poly(vinyl alcohol), poly (acrylic acid), or mixtures of these polymers. A variety of other polymers are known in the art which can be used in the sensors in an analogous fashion, for example polycarboxystyrene. As is known in the art, the polymer matrix of these embodiments can be manipulated. In a illustrative example of such an architecture, the polymer matrix is a multiple attachment-point polymer made from compounds such as cross-linked poly(vinyl alcohol), cross-linked poly(acrylic acid), star dendrimers and mixtures of these polymers. In embodiments of the invention, the polymer matrix includes grafted polymers. Preferably the polymer matrix includes a blend of polymers selected to affect the pH and/or solubility of the environmental milieu surrounding the biosensor molecule.

In related embodiments of the invention, the biosensor is contained in a biocompatible, water-insoluble material that is permeable to glucose such as polyesters of carbonic acid, poly(vinylchloride), polyamides, polychloroethers, poly (urethanes), poly(imides) and mixtures of these materials. A variety of other water-insoluble materials are known in the art which can be used in the sensors in an analogous fashion.

A related embodiment of the invention is a fluorescent biosensor system for measuring levels of glucose which includes one of the fluorescent compounds described herein (e.g. Nile Blue) that is attached to, or contained within, a polymer matrix to form the biosensor of the biosensor system, an optical light source and a detector which detects a fluorescent signal, wherein the signal can be correlated to in-vivo levels of glucose. In preferred embodiments, the biosensor can be subcutaneously implanted in a person's body, for example by being injected subcutaneously beneath a person's skin. Alternatively the sensor can include an optical fiber for percutaneous implantation. In such embodiments, an implanted biosensor can be transdermally excited by an excitation signal from the light source and in response to the excitation signal can emit a fluorescent signal that is detectable by the detector. As is known in the art, such sensors can be manipulated or modified in a variety of ways. For example, in one embodiment, there is a biocompatible coating on the surface of the biosensor. In another embodiment, the sensor can include an adhesion coating, an angiogenic coating and mixtures thereof.

Other embodiments of the invention involve methods for manipulating the polymer matrix to affect the pH and/or solubility of the environmental milieu surrounding the biosensor molecule and/or system. An illustrative example of such a method includes a method of incorporating a sufficient amount of a hydrophilic polymer into a polymer matrix such that the solubility of the biosensor and/or system is enhanced. In a typical method, a hydrophilic polymer (preferably polyethylene glycol) is incorporated into the polymer matrix of an anthracene boronate biosensor in order to enhance the overall solubility of the sensor system. As is known in the art, such polymer matrices can be manipulated or modified in a variety of ways.

Another aspect of the invention are methods of quantifying the amount of polyhydroxylate analyte in-vivo, particularly glucose. These methods include interrogating an implanted oxazine-based biosensor, which includes oxazine-based biosensor molecules contained within or attached to a polymer matrix, with a light source to produce excited state biosensor molecules that yield an emission signal. This emission signal, which correlates to the amount of polyhydroxylate analyte in the body fluids surrounding the biosensor implant, is then detected by a detector. The amount of polyhydroxylate analyte surrounding the in-vivo implanted biosensor is then quantified from the emission signal. These methods preferably utilize biosensor molecules that have a maximal emission signal at about 600 nm or greater, more preferably at about 675 nm.

The invention described herein has a number of embodiments. A preferred embodiment includes an method of quantifying the amount of glucose, the method including interrogating a subcutaneously implantable biosensor which includes biosensor molecules described herein (e.g. Nile Blue) contained in or attached to a polymer matrix, with a light source to produce an excited state of the biosensor molecules that yield an emission signal that can be correlated to the amount of glucose in body fluids surrounding an implanted biosensor, wherein the biosensor molecules include an anilinic group and a fluorophore that includes an iminium ion, detecting the emission signal; and then quantifying the amount of glucose from the emission signal. As is known in the art, a variety of methods can be employed to qualify and quantify the fluorescent signal of the compounds of the present invention. In one embodiment of these methods, one can quantify the amount of glucose via lifetime measurements of the biosensor molecules.

Although the sensor molecules for sugars like glucose are of primary interest for biomedical applications, the present sensor/transducer scheme is useful more generally for the measurement of other cis-diols. For example, the present sensor molecules have utility in the measurement of ethylene glycol contamination in boiler waters, where ethylene gycol contamination is an indication of heat exchanger tube degradation as well as other uses in similar contexts (see e.g. U.S. Pat. No. 5,958,192). These sensor molecules, can be of use in industrial fermentation processes (e.g. beer and wine), or in any number of process points in the production of high fructose corn syrup such as. enzyme reactors and the like (see e.g. U.S. Pat. Nos. 5,593,868; 4,025,389; Ko et al., Biotechnol. Bioeng. 57(4): 430–437 (1998) and Mou et al., Biotechnol. Bioeng. 18(10): 1371–1392 (1976)). Moreover, sensor molecules described herein exhibit characteristics which them particularly suited for uses such as the monitoring of industrial fermentation processes. In addition, as these compounds have the ability to bind saccharides, they can also be used qualitatively as fluorescent probes for carbohydrate molecules such as those found in the cell surfaces of bacteria (see, e.g., Burnett et al., Biochem. Biophys. Res. Comm. 96(1): 157–162 (1980). Such probes are useful, for example, for identifying the presence of bacterial contamination in a number of environments.

EXAMPLES

1. Typical Method for Making an Oxazine-Based Boronate Molecule of the Invention The following example outlines typical synthetic steps for making particular embodiments of the oxazine-based boronate molecules of the invention.

Synthesis: Synthesis of 1 was accomplished by reacting Nile Blue A perchlorate with neopentylglycol-protected 2-bromomethyl phenyl boronic acid in refluxing acetonitrile overnight (Scheme A).

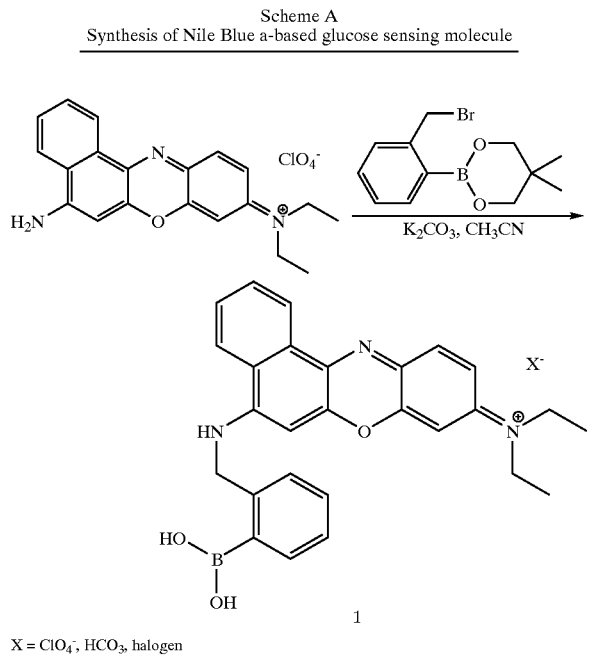

Results: After work-up, the reaction was concentrated to dryness. A sample of the blue residue (~1 mg), dissolved in DMSO (1 ml), was aliquoted (100 □ L) and dissolved in PBS (20 mL). A sample PBS solution (3 mL) contained in a cuvette and irradiated at 621 nm, gave rise to the appearance of a maximum emission peak at 671 nm. Successive additions of glucose (150 mg/dL), added to the cuvette, led to an increase in excitation intensity, at 671 nm, after each addition. Shown in Figure C are the results. The first addition of glucose gave rise to a 7.5% increase in fluorescence at 671 nm. After the second addition of glucose, the intensity rose 14.3% relative to the blank. Addition of the third aliquot of glucose gave an 18.8% rise in fluorescent intensity relative to the blank. This experiment was repeated on a separate batch of Nile Blue A boronate giving 23.4%, 37.8% and 47.4% increase in fluorescent intensity for the same glucose concentrations mentioned above. A control fluorescence experiment was performed containing Nile Blue A using the same conditions as mentioned above. Upon addition of glucose, the fluorescent intensity dropped relative to the blank, due to dilution of the sample, indicating that Nile Blue A is incapable of transducing glucose in DMSO/PBS solutions.

This data allows the functional development and use of a novel oxazine-based long wavelength glucose-transducing sensor whose fluorescence and water solubility characteristics make it an ideal candidate for subcutaneous glucose quantification. This sensor has superior excitation and emission wavelengths, relative to anthracene, and is capable of penetrating human tissue for accurate and reliable fluorescence detection. Additionally, its ability to transduce glucose in substantially aqueous systems provides another key distinction between this glucose sensor and other known glucose sensors.

2. Synthesis of Nile Blue Boronate Starting From the Perchlorate Salt

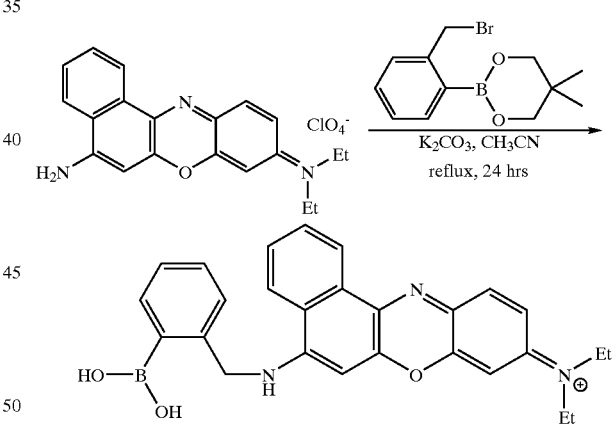

To a round bottom flask, equipped with a reflux condenser under $N_2$, containing Nile Blue perchlorate salt (42 mg, 0.1 mmol), boronate (28 mg, 0.1 mmoles) and $K_2CO_3$ (~1 g) was added $CH_3CN$ (25 mL). The reaction was heated at reflux for 24 hours after which the solvent evaporated and the reaction went to dryness. The sample of the reaction mixture (1 mg, 2.21 mole) was dissolved in DMSO (1 mL). An aliquot (100 µL) was dissolved in PBS (20 mL). A sample of this solution (3 mL) was placed into the fluorolog and fluorescent measurements were made (ex=621 nm, slits at 10 and 20) at various glucose concentrations (0 mg/dL, 150 mg/dL, 300 mg/dL and 450 mg/dL) with a sampling interval of 45 min. The fluorescent intensity increase was 0%, 10%, 16%, 18.5%, 16.5% at 0 mg/dL, 150 mg/dL, 300 mg/dL, 450 mg/dL and 600 mg/dL at 671 nm.

3. Synthesis of Nile Blue Boronate Using the Free Boronic Acid

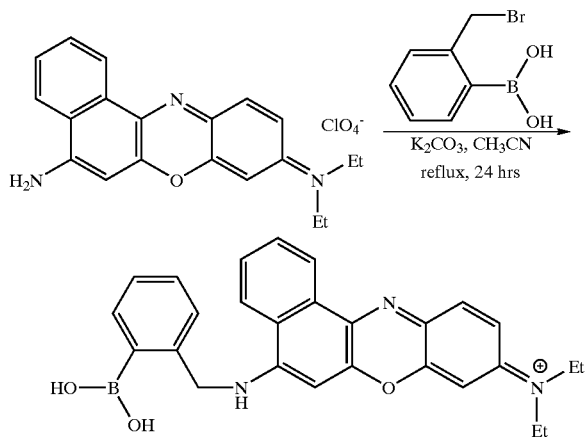

To a round bottom flask, equipped with a reflux condenser under N₂, containing Nile Blue perchlorate salt (42 mg, 0.1 mmol), boronate (22 mg, 0.1 mmoles) and K₂CO₃ (~1 g) was added CH₃CN (25 mL). The reaction was heated at reflux for 24 hours but the reaction did not go to dryness. The sample of the reaction mixture (1 mg, 2.21 mmol) was dissolved in DMSO (1 mL). An aliquot (100 μL) was dissolved in PBS (20 mL). A sample of this solution (3 mL) was placed into the fluorolog and fluorescent measurements were made (ex=621 nm, slits at 10 and 20) at various glucose concentrations (0 mg/dL, 150 mg/dL, 300 mg/dL and 450 mg/dL) with a sampling interval of 45 min. The fluorescent intensity increase was 0%, -2% and -6% at 0 mg/dL, 150 mg/dL and 300 mg/dL at 671 nm.

4. —Synthesis of Nile Blue Boronate Starting From the Perchlorate Salt

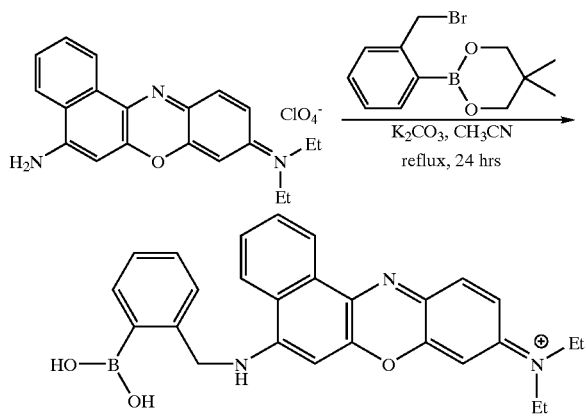

To a round bottom flask, equipped with a reflux condenser under N₂, containing Nile Blue perchlorate salt (42 mg, 0.1 mmol), boronate (28 mg, 0.1 mmoles) and K₂CO₃ (~1 g) was added CH₃CN (25 mL). The reaction was heated at reflux for 24 hours after which the solvent evaporated and the reaction went to dryness. The sample of the reaction mixture (1 mg, 2.21 mmol) was dissolved in DMSO (1 mL). An aliquot (100 μL) was dissolved in PBS (20 mL). A sample of this solution (3 mL) was placed into the fluorolog and fluorescent measurements were made (ex=621 nm, slits at 10 and 20) at various glucose concentrations (0 mg/dL, 150 mg/dL, 300 mg/dL and 450 mg/dL) with a sampling interval of 45 min. The fluorescent intensity increase was 0%, 7.0% and 9.5% at 0 mg/dL, 150 mg/dL, and 300 mg/dL at 671 nm.

5. Synthesis of Nile Blue Boronate Starting From the Perchlorate Salt in DMSO

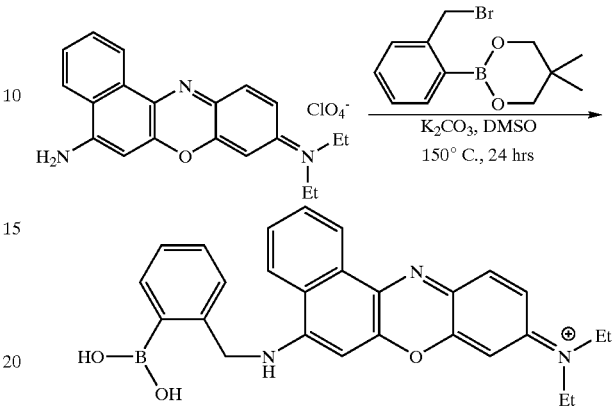

To a round bottom flask, equipped with a reflux condenser under N₂, containing Nile Blue petchlorate salt (42 mg, 0.1 mmol), boronate (28 mg, 0.1 mmoles) and K₂CO₃ (~1 g) was added DMSO (20 mL). The reaction was heated at 150° C. for 24 hours. The reaction was diluted with H₂O (200 mL) and passed through a C₁₈ cartridge. The aq. sample was concentrated to dryness. The sample of the reaction mixture (1 mg, 2.21 mmol) was dissolved in DMSO (1 mL). An aliquot (100 μL) was dissolved in PBS (20 mL). A sample of this solution (3 mL) was placed into the fluorolog and fluorescent measurements were made (ex=621 nm, slits at 10 and 20) at various glucose concentrations (0 mg/dL, 150 mg/dL, 300 mg/dL and 450 mg/dL) with a sampling interval of 45 min. The fluorescent intensity increase was 0%, 29.8%, 27.2% and 31.1% at 0 mg/dL, 150 mg/dL, and 300 mg/dL at 671 nm.

6. Synthesis of Nile Blue Boronate Starting From the Chloride Salt and Boroxin

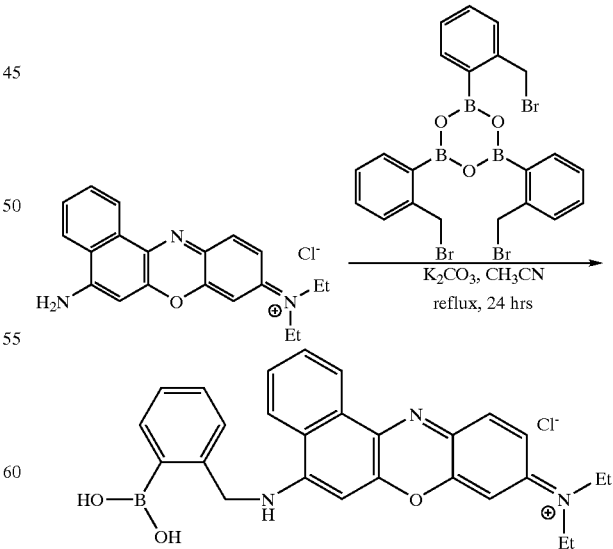

Boroxin was prepared via azeotropic removal of water with a Dean Stark trap in refluxing toluene for 2 hr. To a round bottom flask, equipped with a reflux condenser under $N_2$, containing Nile Blue chloride salt (89% pure, 660 mg, 1.67 mmol), boroxin (346 mg, 0.55 mmoles) and $K_2CO_3$ (~1.5 g) was added $CH_3CN$ (120 mL). The reaction was immersed in an oil bath at 140° C. for 24 hr. The reaction was cooled to RT and the solids were filtered off. The solid portion was washed with $H_2O$ until the washings were clear, colorless. The sample of the reaction mixture (20 mg) was dissolved in DMSO (1 mL). An aliquot (100 μL) was dissolved in PBS (20 mL). A sample of this solution (3 mL) was placed into the fluorolog and fluorescent measurements were made (ex=621 nm, slits at 10 and 20) at various glucose concentrations (0 mg/dL, 150 mg/dL, 300 mg/dL and 450 mg/dL) with a sampling interval of 45 min. The fluorescent intensity increase was 0%, 15.4%, 7.1% and 18.3% at 0 mg/dL, 150 mg/dL, 300 mg/dL and 450 mg/dL at 671 nm.

7. Synthesis of Nile Blue Boronate Starting From Chloride Salt

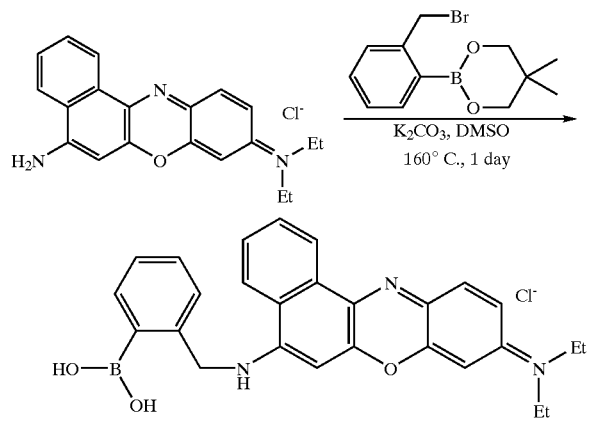

To a round bottom flask, equipped with a reflux condenser under $N_2$, containing Nile Blue (89% pure, 660 mg, 1.67 mmoles), boronate (471 mg, 1.67 mmoles) and $K_2CO_3$ (~2 g) was added DMSO (20 mL). The flask was immersed into an oil bath at 150° C. for 1 day. An aliquot (20 μL) was dissolved in PBS (20 mL). A sample of this solution (3 mL) was placed into the fluorolog and fluorescent measurements were made (ex=621 nm, slits at 10 and 20) at various glucose concentrations (0 mg/dL, 150 mg/dL, 300 mg/dL and 450 mg/dL) with a sampling interval of 45 min. The fluorescent intensity increase was 0%, 4.0%, and −7.4% at 0 mg/dL, 150 mg/dL, and 300 mg/dL at 671 nm.

8. Synthesis of Nile Blue Boronate Via Reductive Amination Starting From Chloride Salt

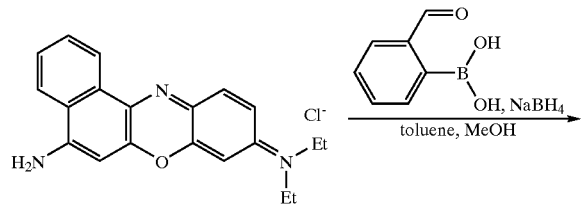

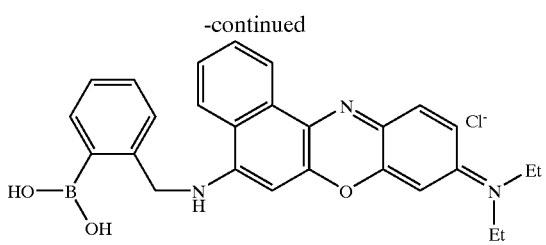

To a round bottom flask, equipped with a reflux condenser and Dean Stark trap under $N_2$, containing Nile Blue (89% pure, 558 mg, 1.67 mmoles) and boronate (251 mg, 1.67 mmoles) was added toluene (100 mL). The flask was immersed into an oil bath at 160° C. for 3 hr. The reaction was cooled to RT and concentrated to dryness. The reaction mixture was redissolved in MeOH (20 mL) and $NaBH_4$ was added to the reaction. After 1 hr, the reaction was concentrated to dryness. Redissolved reaction in AcOH (75 mL) and $H_2O$ (125 mL). An aliquot (50 μL) was dissolved in PBS (20 mL). A sample of this solution (3 mL) was placed into the fluorolog and fluorescent measurements were made (ex=621 nm, slits at 10 and 20) at various glucose concentrations (0 mg/dL, 150 mg/dL, 300 mg/dL and 450 mg/dL) with a sampling interval of 45 min. The fluorescent intensity increase was 0%, 0%, 0% and 0% at 0 mg/dL, 150 mg/dL, 300 mg/dL and 450 mg/dL.

9. Synthesis of Nile Blue Boronate

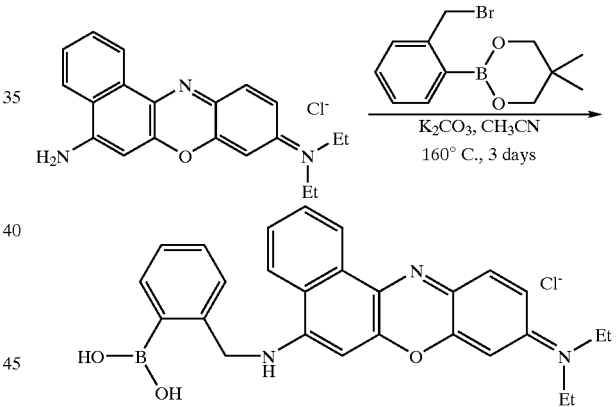

To a round bottom flask, equipped with a reflux condenser under $N_2$, containing Nile Blue (pre-washed with $Et_2O$ (5×'s), 89% pure, 1.32 g, 3.3 mmoles), boronate (692 mg, 2.45 mmoles) and $K_2CO_3$ (~2 g) was added $CH_3CN$ (100 mL). The flask was immersed into an oil bath at 160° C. for 3 days. The reaction was cooled to RT and the solids were filtered. The solids were washed with $CH_3CN$ (3×20 mL), $H_2O$ (3×50 mL), $CH_3CN$ (1×20 mL) and $Et_2O$ (3×20 mL) to afford 600 mg (54%) of a dark blue solid.

The product (1 mg, 2.21 mmol) was dissolved in DMSO (1 mL). An aliquot (100 μL) was dissolved in PBS (20 mL). A sample of this solution (3 mL) was placed into the fluorolog and fluorescent measurements were made (ex=621 nm, slits at 10 and 20) at various glucose concentrations (0 mg/dL, 150 mg/dL, 300 mg/dL and 450 mg/dL) with a sampling interval of 45 min. The fluorescent intensity increase was 0%, 25%, 35% and 40% at 0 mg/dL, 150 mg/dL, 300 mg/dL and 450 mg/dL at 671 nm.

10. Stepwise Synthesis of Nile Blue Boronate with Carboxylate Linker

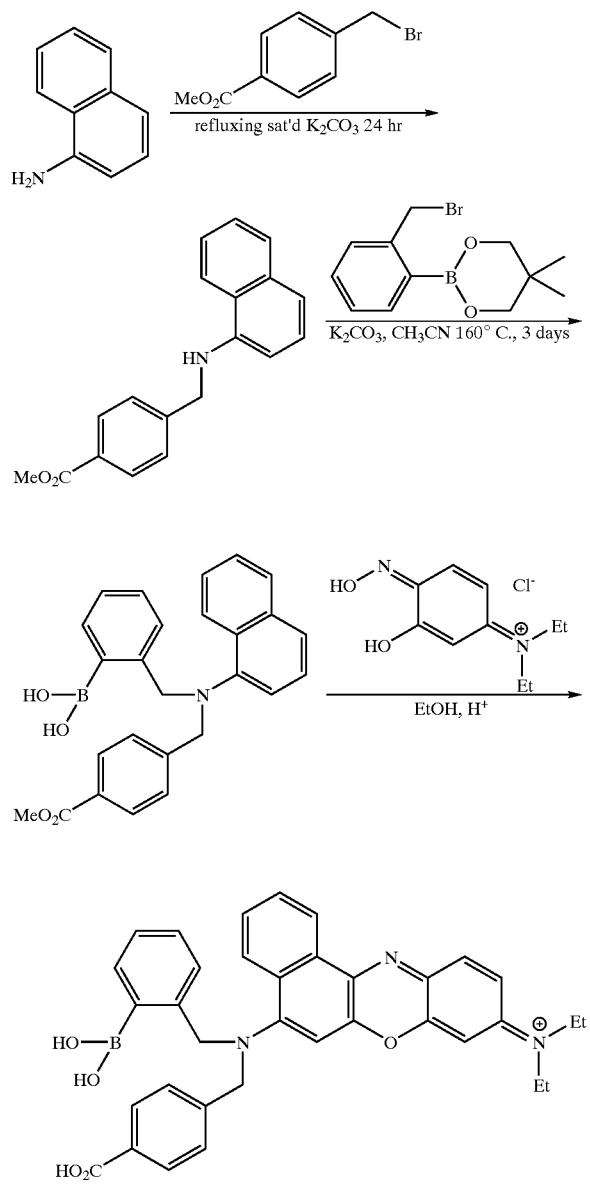

See, e.g., methods described in Crossley et al., *J. Am. Chem. Soc.* 1952, 74, 573–578 which is incorporated herein by reference.

11. Synthesis of 4-(Naphthalen-1-ylaminomethyl)-benzoic Acid Methyl Ester

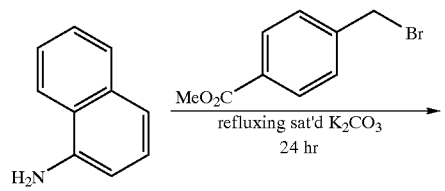

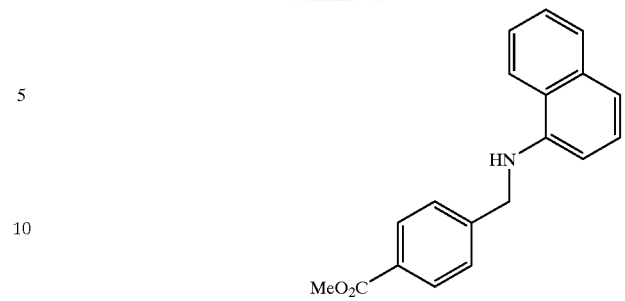

To a round bottom flask containing aminonaphthalene (1.43 g, 10 mmol) dissolved in sat'd $K_2CO_3$ (150 mL) was added aryl ester (2.29 g, 10 mmol). Refluxed overnight. The reaction was cooled to RT and extracted with $Et_2O$ (5×100 mL). The combined organic fractions were dried ($MgSO_4$), filtered and concentrated to dryness. The crude material was purified on silica gel using 40% $Et_2O$:Hex as the eluent to afford 350 mg of a light yellow solid.

12. Synthesis of 4-{[(2-benzylboronic acid)-naphthalen-1-yl-amino]-methyl}-benzoic Acid Methyl Ester

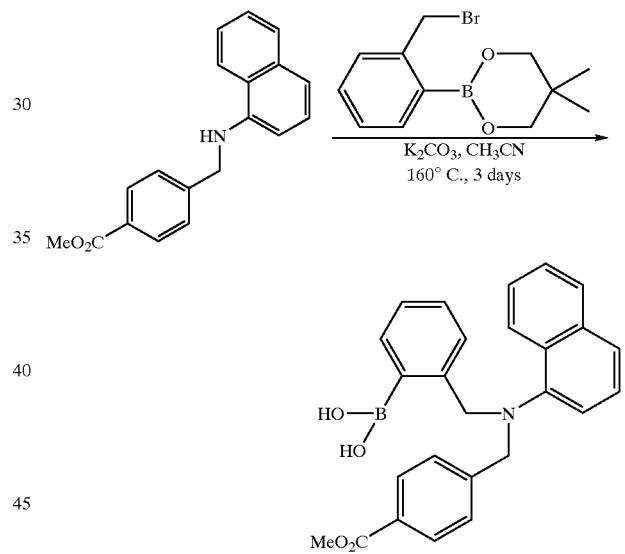

To a round bottom flask containing aminoester (350 mg, 1.2 mmol) dissolved in $CH_3CN$ was added $K_2CO_3$ (1.5 g) and boronate (339 mg, 1.2 mmol). Refluxed for 3 days. The reaction was cooled to RT and extracted with $Et_2O$ (5×100 mL). The combined organic fractions were dried $MgSO_4$), filtered and concentrated to dryness. The crude material was purified on silica gel using 40% $Et_2O$:Hex as the eluent to afford 350 mg of a light yellow solid.

13. Stepwise Synthesis of Nile Blue Boronate with Amino or Hydroxyl Linker

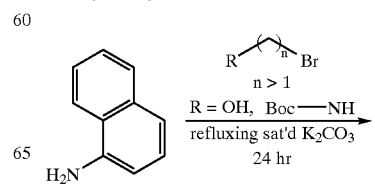

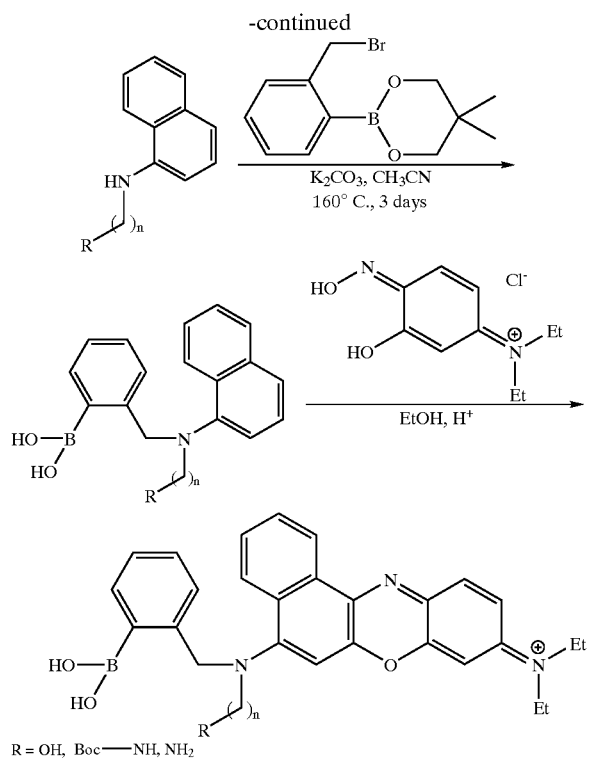

R = OH, Boc—NH, NH$_2$

Appendix B attached herein provides redundant color reproductions of the glucose transduction experiments disclosed in the examples.

Throughout the specification various patents, patent applications and other publications are referenced. The entire content of these patents, patent applications and other publications are incorporated herein by reference.

The foregoing written description is considered to be sufficient to enable one skilled in the art to practice the invention. Further, the present invention is not to be limited in scope by the examples presented herein. Indeed, various modifications to the present invention, in addition to those shown and described herein will become apparent to those skilled in the art from the foregoing description and fall within the scope of the appended claims.

What is claimed is:

1. A fluorescent compound comprising:
   a fluorophore including a charged moiety;
   an anilinic group in relation to the fluorophore;
   a boronate moiety capable of binding glucose;
   a linker moiety that links the fluorophore to the boronate binding moiety;
   wherein the compound exhibits an alteration in fluorescent properties when the boronate moiety is bound to glucose.

2. The compound of claim 1, wherein the compound emits a fluorescent signal in the visible to near infrared region of the spectrum that can be correlated to the presence of glucose in a substantially aqueous medium.

3. The compound of claim 1, wherein the compound has at least one maximum wavelength in an emission spectrum of the fluorophore that is between about 600 nm and about 800 nm.

4. The compound of claim 1, wherein the excitation wavelength for the fluorophore is greater than about 600 nm.

5. The compound of claim 1, wherein the compound is attached to a polymer matrix.

6. The compound of claim 5, wherein the polymer matrix includes polyethylene glycol.

7. The compound of claim 1, wherein the compound further includes one or more functional groups selected from the group consisting of at least an aliphatic, an aromatic, a haloalkane, an alcohol, an ether, an amine, an imine, an aldehyde, a ketone, an ester, a carboxylic acid, a sulfonic acid a cyano group, a phosphoric acid, and salts thereof.

8. The compound of claim 1, wherein the charged moiety is an minimum ion.

9. The compound of claim 1, wherein the fluorophore is Nile Blue.

10. An implantable biosensor, the biosensor comprising the biosensor compound of claim 1 contained in a polymer matrix.

11. The implantable biosensor of claim 10, wherein the polymer matrix is biocompatible, water-soluble and permeable to the glucose.

12. The implantable biosensor of claim 11, wherein the polymer matrix is selected from at least polyethylene glycol (amino-terminated), polyethylene glycol (hydroxy terminated), Jeffamine polymers (2-propyl amino terminated block-polypropylene oxide block-polyethylene oxide block-polypropylene oxide), poly(vinyl alcohol), poly (acrylic acid), and mixtures of these polymers.

13. The implantable biosensor of claim 10, wherein the biosensor is contained in a biocompatible, water-insoluble material that is permeable to glucose.

14. The biosensor of claim 13, wherein the water-insoluble material is selected from at least polyesters of carbonic acid, poly(vinylchloride), polyamides, polychloroethers, poly(urethanes), poly(imides) and mixtures of these materials.

15. The biosensor of claim 10, wherein the polymer matrix is a multiple attachment-point polymer.

16. The biosensor of claim 15, wherein the multiple attachment-point polymer is selected from at least cross-linked poly(vinyl alcohol), cross-linked poly(acrylic acid), star dendrimers and mixtures of these polymers.

17. The biosensor of claim 10, wherein the polymer matrix is polycarboxystyrene.

18. The biosensor of claim 16, wherein the polymer matrix includes a blend of polymers selected to affect the pH and/or solubility of the environmental milieu surrounding the biosensor molecule.

19. The biosensor of claim 16, wherein the polymer matrix includes grafted polymers.

20. A ditopic biosensor molecule, the biosensor molecule comprising:
    a first biosensor molecule of claim 1;
    a second biosensor molecule of claim 1; and
    a bridging linker element, wherein the bridging linker element forms a bridge between the first and the second biosensor molecules and wherein the first and second biosensor molecules are the same or different.

21. The ditopic biosensor molecule of claim 20, wherein the ditopic biosensor binds glucose below about 100 mg/dL of analyte and emits a detectable emission signal that correlates to the glucose binding below about 100 mg/dL.

22. The ditopic biosensor molecule of claim 21, wherein the ditopic sensor also binds glucose up to about 1000 mg/dL of analyte and emits a detectable emission signal that correlates with glucose binding up to about 1000 mg/dL of analyte.

23. The ditopic biosensor molecule of claim 20, wherein the ditopic biosensor emits light at about 600 nm or greater.

24. The ditopic biosensor molecule of claim 20, further comprising a functional group capable of forming a covalent linkage to a polymer matrix.

25. The ditopic biosensor molecule of claim 24, wherein the ditopic biosensor molecule is attached to a polymer matrix.

26. The ditopic biosensor molecule of claim 20, wherein one of the biosensor molecules includes a Nile Blue fluorophore.

27. The ditopic biosensor molecule of claim 20, wherein the ditopic molecule emits a fluorescent signal at about 600 nm or greater.

28. The ditopic biosensor molecule of claim 20, wherein the bridging linker element includes 2–10 carbons.

29. A compound having a formula comprising:

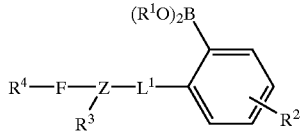

wherein:
F is a fluorophore including an iminium ion;
B is a boron atom;
$R^1$ is selected from the group consisting of hydrogen, aliphatic and aromatic functional groups, wherein the functional group $(R^1O)_2B$ is capable of binding glucose;
$R^2$, $R^3$ and $R^4$ are optional and independent functional groups selected from the groups consisting of hydrogen, aliphatic and aromatic functional groups, further functionalized aliphatic and aromatic groups, functional groups that alter the electronic properties of the group to which they are attached and functional groups that are capable of forming covalent linkages to a polymer matrix;
$L^1$ is an optional linking group having from zero to four atoms selected from the group consisting of nitrogen, carbon, oxygen, sulfur and phosphorous; and
Z is a heteroatom selected from the group consisting of nitrogen, phosphorous, sulfur, and oxygen; wherein the heteroatom is in an anilinic-type relationship to the fluorophore;
wherein the fluorescence of the compound increases in the presence of bound glucose.

30. The compound of claim 29, wherein Z is nitrogen.

31. The biosensor molecule of claim 29, wherein $R^3$ is a hydroxyl carbonyl, a carboxylic acid, carboxylate or an amine functional group.

32. The compound of claim 31, wherein the hydroxyl, carbonyl, a carboxylic acid, carboxylate or amine functional group includes an aliphatic linker with 2 or more carbon atoms.

33. The compound of claim 29, wherein the excitation wavelength for the fluorophore is greater than about 600 nm and wherein the compound is able to emit a fluorescent signal having a wavelength of greater than about 600 nm.

34. A fluorescent biosensor system for measuring levels of glucose, the biosensor system comprising:
the fluorescent compound of claim 29 attached to, or contained within, a polymer matrix to form the biosensor of the biosensor system;
an optical light source; and
a detector which detects a fluorescent signal, wherein the signal can be correlated to in-vivo levels of glucose.

35. The biosensor system of claim 34, wherein the biosensor can be subcutaneously implanted in a person's body.

36. The biosensor system of claim 35, wherein an implanted biosensor can be transdermally excited by an excitation signal from the light source and in response to the excitation signal can emit a fluorescent signal that is detectable by the detector.

37. The biosensor system of claim 34, wherein the biosensor can be injected subcutaneously beneath a person's skin.

38. The biosensor system of claim 34, further comprising an optical fiber for percutaneous implantation.

39. The biosensor system of claim 34, further comprising at least one biocompatible coating on the surface of the biosensor.

40. The biosensor of claim 39, further comprising an at least an adhesion coating, an angiogenic coating and mixtures thereof.

41. The biosensor system of claim 34, wherein the fluorescent compound includes a Nile Blue moiety.

42. A fluorescent compound of the general formula:

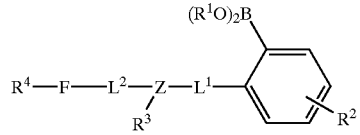

wherein:
F is a Nile Blue moiety;
B is a boron atom;
$R^1$ is selected from the group consisting of hydrogen, aliphatic and aromatic functional groups, wherein the functional group $(R^1O)_2B$ is capable of binding glucose;
$R^2$, $R^3$ and $R^4$ are optional and independent functional groups selected from the groups consisting of hydrogen, aliphatic and aromatic functional groups, further functionalized aliphatic and aromatic groups, functional groups that alter the electronic properties of the group to which they are attached and functional groups that are capable of forming covalent linkages to a polymer matrix;
$L^1$ and $L^2$ are optional linking groups having from zero to four atoms selected from the group consisting of nitrogen, carbon, oxygen, sulfur and phosphorous; and
Z is a heteroatom selected from the group consisting of nitrogen, phosphorous, sulfur, and oxygen wherein the heteroatom is in an anilinic-type relationship to the Nile Blue moiety.

43. A method of quantifying the amount of glucose, the method comprising:
interrogating a subcutaneously implantable biosensor which includes biosensor molecules contained in or attached to a polymer matrix, with a light source to produce an excited state of the biosensor molecules that yield an emission signal that can be correlated to the amount of glucose in body fluids surrounding an implanted biosensor, wherein the biosensor molecules include an anilinic group and a fluorophore that includes an iminium ion;
detecting the emission signal; and
quantifying the amount of glucose from the emission signal.

44. The method of claim 43, wherein the biosensor molecules have an emission signal at about 650 nm or greater.

45. The method of claim 43, wherein the biosensor molecules comprise a molecule of the formula:

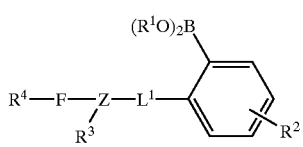

wherein:
F is the fluorophore including the iminium ion;
B is a boron atom;
$R^1$ is selected from the group consisting of hydrogen, aliphatic and aromatic functional groups, wherein the functional group $(R^1O)_2B$ is capable of binding polyhydroxylate analyte;
$R^2$, $R^3$ and $R^4$ are optional and independent functional groups selected from the groups consisting of hydrogen, aliphatic and aromatic functional groups, further functionalized aliphatic and aromatic groups, functional groups that alter the electronic properties of the group to which they are attached and functional groups that are capable of forming covalent linkages to a polymer matrix;
$L^1$ is an optional linking group having from zero to four atoms selected from the group consisting of nitrogen, carbon, oxygen, sulfur and phosphorous; and
Z is a heteroatom selected from the group consisting of nitrogen, phosphorous, sulfur, and oxygen, wherein the heteroatom is in an anilinic-type relationship to the fluorophore and wherein the fluorescence of the biosensor molecule increases in the presence of bound glucose.

46. The method of claim 43, wherein quantifying the amount of glucose involves lifetime measurements of the biosensor molecules.

\* \* \* \* \*

UNITED STATES PATENT AND TRADEMARK OFFICE
CERTIFICATE OF CORRECTION

PATENT NO. : 6,766,183 B2  
APPLICATION NO. : 10/033240  
DATED : July 20, 2004  
INVENTOR(S) : Walsh et al.

Page 1 of 1

It is certified that error appears in the above-identified patent and that said Letters Patent is hereby corrected as shown below:

On the title page, item 56,

Page 2  
OTHER PUBLICATIONS, line 49, "methylnaphrhalenes" should read --methylnaphthalenes--.

On the title page, item 56,

Page 3  
OTHER PUBLICATIONS, Column 1, line 10, "Guilbaulr" should read --Guilbault--, "Homovanillie" should read --Homovanillic--,  
Column 2, line 13 "Sandanvake" should read --Sandanayake--.

Column 32  
Line 10, "miniumum" should read --iminium--.  
Line 42, Line 46, "16" should read --10--.

Column 33  
Line 46, after "hydroxyl" insert a comma --,--.

Signed and Sealed this

Twenty-ninth Day of August, 2006

JON W. DUDAS  
*Director of the United States Patent and Trademark Office*